United States Patent
St. John et al.

(10) Patent No.: US 10,041,136 B2
(45) Date of Patent: Aug. 7, 2018

(54) GLYCOSYL HYDROLASE XYLANASES, COMPOSITIONS AND METHODS OF USE FOR EFFICIENT HYDROLYSIS AND PROCESSING OF XYLAN

(71) Applicant: The United States of America as Represented by the Secretary of Agriculture, Washington, DC (US)

(72) Inventors: Franz St. John, Madison, WI (US); Diane Dietrich, Madison, WI (US); Merritt E. Casey Crooks, Madison, WI (US)

( * ) Notice: Subject to any disclaimer, the term of this patent is extended or adjusted under 35 U.S.C. 154(b) by 0 days.

(21) Appl. No.: 14/795,296

(22) Filed: Jul. 9, 2015

(65) Prior Publication Data
US 2016/0040203 A1   Feb. 11, 2016

Related U.S. Application Data

(60) Provisional application No. 62/023,116, filed on Jul. 10, 2014.

(51) Int. Cl.
| | |
|---|---|
| C12N 9/24 | (2006.01) |
| C12P 19/14 | (2006.01) |
| C07H 21/04 | (2006.01) |
| C13K 13/00 | (2006.01) |

(52) U.S. Cl.
CPC .... C12Y 302/01008 (2013.01); C12N 9/2482 (2013.01); C12P 19/14 (2013.01); C13K 13/002 (2013.01)

(58) Field of Classification Search
None
See application file for complete search history.

(56) References Cited

PUBLICATIONS

Whisstock et al. Quaterly Reviews of Biophysics, 2003, "Prediction of protein function from protein sequence and structure", 36(3): 307-340.*
Witkowski et al. Conversion of a beta-ketoacyl synthase to a malonyl decarboxylase by replacement of the active-site cysteine with glutamine, Biochemistry. Sep. 7, 1999;38(36):11643-50.*
St John et al. A novel member of glycoside hydrolase family 30 subfamily 8 with altered substrate specificity, Acta Cryst. (2014), D70, 2950-2958.*
Harris et al. Stimulation of Lignocellulosic Biomass Hydrolysis by Proteins of Glycoside Hydrolase Family 61: Structure and Function of a Large, Enigmatic Family., Biochemistry 2010, 49, 3305-3316.*
Cantarel, Brandi L., et al. "The Carbohydrate-Active EnZymes database (CAZy): an expert resource for glycogenomics." Nucleic acids research 37.suppl 1 (2009): D233-D238.
StJohn, Franz J., Javier M. Gonzalez, and Edwin Pozharski. "Consolidation of glycosyl hydrolase family 30: a dual domain 4/7 hydrolase family consisting of two structurally distinct groups." FEBS letters 584.21 (2010): 4435-4441.
StJohn, Franz J., John D. Rice, and James F. Preston. "Characterization of XynC from *Bacillus subtilis* subsp. *subtilis* strain 168 and analysis of its role in depolymerization of glucuronoxylan." Journal of bacteriology 188.24 (2006): 8617-8626.
Hurlbert, Jason C., and James F. Preston. "Functional characterization of a novel xylanase from a corn strain of Erwinia chrysanthemi." Journal of bacteriology 183.6 (2001): 2093-2100.
StJohn, Franz J., et al. "Ligand bound structures of a glycosyl hydrolase family 30 glucuronoxylan xylanohydrolase." Journal of molecular biology 407.1 (2011): 92-109.
Urbanikova, L'ubica, et al. "Structural basis for substrate recognition by Erwinia chrysanthemi GH30 glucuronoxylanase." FEBS Journal 278.12 (2011): 2105-2116.
Welch, Mark, et al. "Design parameters to control synthetic gene expression in *Escherichia coli*." PloS one 4.9 (2009): e7002.
Laemmli, Ulrich K. "Cleavage of structural proteins during the assembly of the head of bacteriophage T4." nature 227.5259 (1970): 680-685.
Gasteiger, Elisabeth, et al. "Protein identification and analysis tools on the ExPASy server." The proteomics protocols handbook. Humana Press, 2005. 571-607.
Battye, T. Geoff G., et al. "iMOSFLM: a new graphical interface for diffraction-image processing with MOSFLM." Acta Crystallographica Section D: Biological Crystallography 67.4 (2011): 271-281.
McCoy, Airlie J. "Solving structures of protein complexes by molecular replacement with Phaser." Acta Crystallographica Section D: Biological Crystallography 63.1 (2007): 32-41.
Adams, Paul D., et al. "PHENIX: a comprehensive Python-based system for macromolecular structure solution." Acta Crystallographica Section D: Biological Crystallography 66.2 (2010): 213-221.
Emsley, Paul, et al. "Features and development of Coot." Acta Crystallographica Section D: Biological Crystallography 66.4 (2010): 486-501.
Delano, Warren Lyford. "The PyMOL molecular graphics system." (2002).
Dubois, Michel, et al. "Colorimetric method for determination of sugars and related substances." Analytical chemistry 28.3 (1956): 350-356.
Biely, P., et al. "Endo-β-1, 4-xylanase families: differences in catalytic properties." Journal of biotechnology 57.1 (1997): 151-166.
Blumenkrantz, Nelly, and Gustav Asboe-Hansen. "New method for quantitative determination of uronic acids." Analytical biochemistry 54 (1973): 484-489.
Nelson, Norton. "A photometric adaptation of the Somogyi method for the determination of glucose." J. biol. Chem 153.2 (1944): 375-380.

(Continued)

*Primary Examiner* — Iqbal H Chowdhury

(57) ABSTRACT

The invention provides a unique subset of GH30 subfamily 8 xylanases (GH30-8) with endo-β-1,4-xylanase activity, compositions comprising an effective amount of the GH30-8 xylanases, methods of synthesis and methods of use thereof.

9 Claims, 19 Drawing Sheets

(56) References Cited

PUBLICATIONS

Bounias, M. "N-(1-Naphthyl) ethylenediamine dihydrochloride as a new reagent for nanomole quantification of sugars on thin-layer plates by a mathematical calibration process." Analytical biochemistry 106.2 (1980): 291-295.
Katoh, Kazutaka, and Hiroyuki Toh. "Recent developments in the MAFFT multiple sequence alignment program." Briefings in bioinformatics 9.4 (2008): 286-298.
Gouet, Patrice, Xavier Robert, and Emmanuel Courcelle. "ESPript/ENDscript: extracting and rendering sequence and 3D information from atomic structures of proteins." Nucleic acids research 31.13 (2003): 3320-3323.
Shaikh, Fathima Aidha, and Stephen G. Withers. "Teaching old enzymes new tricks: engineering and evolution of glycosidases and glycosyl transferases for improved glycoside synthesis." Biochemistry and Cell Biology 86.2 (2008): 169-177.
Gallardo, Óscar, et al. "Characterization of a family GH5 xylanase with activity on neutral oligosaccharides and evaluation as a pulp bleaching aid." Applied and environmental microbiology 76.18 (2010): 6290-6294.
Vrsanska, M, Biely, P. and Kratky, Z. "Enzymes of the yeast lytic system produced by Arthrobacter GJM-1 bacterium and their role in the lysis of yeast cell walls." Journal of Basic Microbiology 17.6 (1977): 465-480.
Petersen, Thomas Nordahl, et al. "SignalP 4.0: discriminating signal peptides from transmembrane regions." Nature Methods 8.10 (2011): 785-786.
Evans, Philip. "Scaling and Assessment of Data Quality." Acta Crystallographica Section D62 (2006): 72-82.
Bateman, A., et al. "The Pfam Protein Families Database." Nucleic Acids Research 32 (2004): D138-D141.

\* cited by examiner

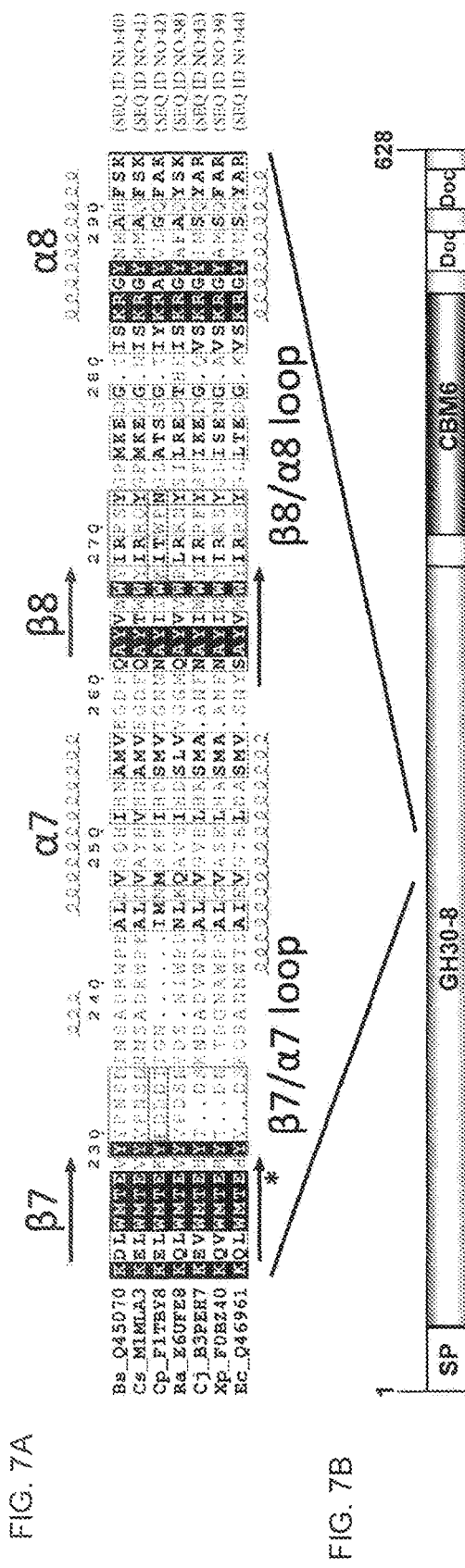
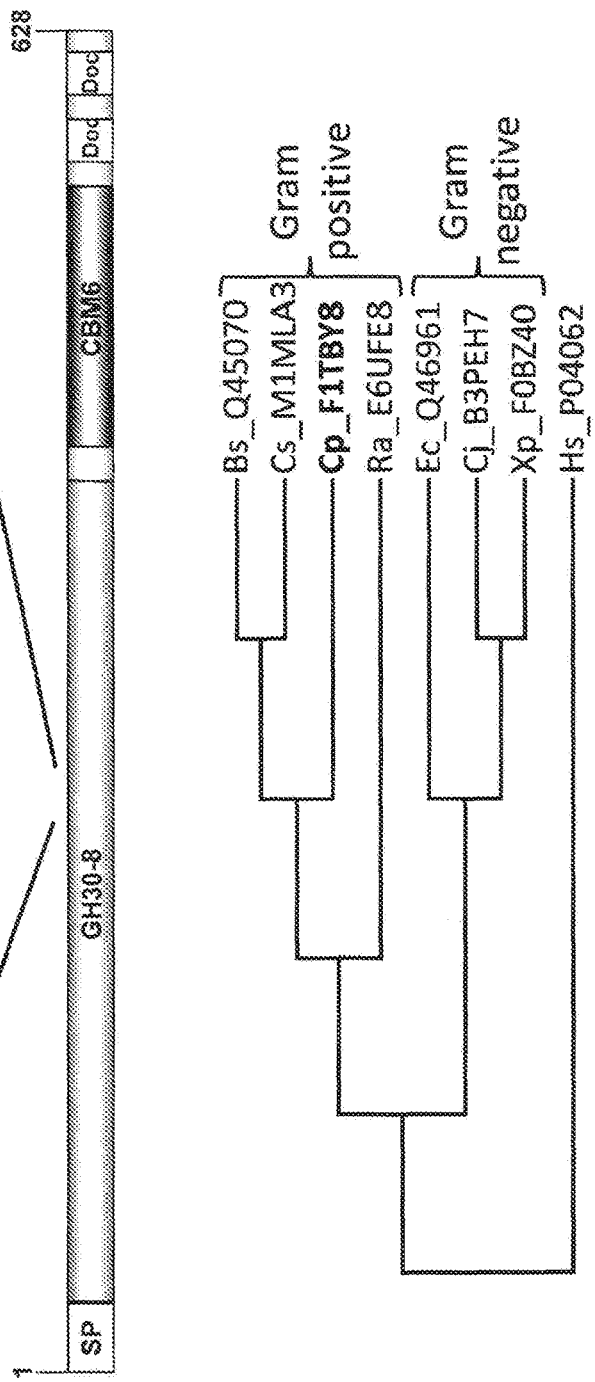
FIG. 7A
FIG. 7B
FIG. 7C

Figure 14

>Q97T12
MNIKLKRTLISLVAFSMTCLPFVGTGSSVKAASNDATINVAAKHQTIRGFGASSAWCGAL
SDTCMDTLYKNAGLDILRVRIAPNEGWNRGDYRAWADELSNAKKVRARGGIVFATPWTPP
ASMKTNNTTTGANKGSLKPSSYAAYAAYLKTFVKYMSDNGAPLYALSLQNEPDWAPDYDA
CTWTAQQFHDFLKQYGASLSSTIKIIMPESLGFNPAMSDPTLNDPTTAQYVSIIGGHLYG
SPIRDYPLARNKGKDIWMTEHYLEGNDPGTCVKLAKEIHDCMTIGNMNAYVYWWISGDQN
GLYNTRTNETYKKTYVMGQFSKFIGNGYSRVDATNSPQSNVYVSAYTGNNKVVIVAINQG
TYPVNQSFNVQNSTVSNVSSWVSSGTLNMAKTNSNISAANGRFNASLPAQSVTPFVADLN
STNPTTDPTTNPTFGSTVTLNNGWYYIKNINAQKYLQVASNTGKAGQNVELGSGSGAAGQ
KWYLTNTGDGYVTLKSALGNYMLDVSYGENKDGSNIQIFNAYSGDAQKFSVKASSKDGQY
FVSTKSSNGTKVLDDYNFGTADGTNVCQWTYGGNANQLWAFEPTNN

Figure 15

>F1TBY8
MFKNMKKTISKVLVSSIIMSALFMVSAPAGVSAASDVTVNLGSTKQEIRG
FGASSAWCGTISDYVMNSLYGDLGYSILRLRIEEGIGDAWKTGNFSKWSP
ELANAKKASAKGAIVFASPWNPPASMQENFSKSGDSSAQRLRYDKYTEYA
QYLNAYVKYMKDNGVDLYAISVQNEPDYAQDWTWWTPQEMLNFMKNNAGS
INCRVMAPESFQFLKNMSDPILNDATALDNMDVLGCHFYGTSVNNMAYPL
YQQKSAGKELWMTEKYFDDDTTGNIMNMSKEIHDSMVTGNMNAYIYWWIT
WPNGLATSSGTIYKRAYVLGQFAKFIRPGYKRVDATATPNTNVYVSAYTG
DNKAVIVAINTGTAAVSQKFNFQNGSASSVVSYVTDSSRNMAAGANIAVT
NGSFTAQLPAQSITTFVGNTAPVVVEPIDAFNKIEAENYYDQSGTQTEAN
SDGNGKNVGYIENEDYLVFKNVDFGSGAASFEASAGSATNGGNIELRLDS
LTGTLIGNCAVPGTGGWQTWTNATCNVSQVTGKHDVYLKFTGESGYLMNL
DWFKFNTKVIPVGKLGDINGDASIDSLDLMLIKKHLLGEAIENTALADLD
GSGAVDAIDLAQMKQYLLGIISAFPGKA

Figure 16

>E4T705
MTQKLIGYLSIACIVFTASCSKSENSPIYTPPPTVNDTVPSTTAGNAILNLTDEQQVIDG
FGGSTAWNGALSDAQADALFGNSDNSQMGLSICRLRIDPNKYWDQEKSNAQKANARGAKV
FASPWSPPVTMKTNNNVVQGALDPTKYADYALYLKSFGDYIKNAGVTLTAISIQNEPDWK
PDYESCSWTGEEIAKFAKENAPAVGYPLMIGESLNFNPTMADFTLNDEAACANVSYIGGH
LYGRDPFKYTNAIDKGKKIWMTEHYYDNANNNISVALSVAKEINACMNLNMNAYVWWWVL
PLNGSICNLINENKAMTKNGCALAQYSKWVRPGFKRVYITPEPYTGICMSAYKNGNKTVI
VIVNSCVVAIKQPITIQNGTITAFTPYETTATKNVAALSKIAVNNGTFSVNLKGQSITTL
VSE

Figure 17

>H1YFT8
MKKNLLGLLGLLAIMGSCSKNSIQQKASQEETLKGTAVIDGGTLYQAIDGIGFSSAWCCQ
LSTAKNNALYGTLGMSLLRVRIDQNSANWADETANSAAAHAAGVKVLGSEWSPPVAWTSN
GQSTGGYLLPQYYANYASYLNQAATNIGLDFVSFQNEPDISGAVLWTPAQILTFVKNNSA
TIGKPIVMPESFHFDDAYSDPVLNDADAVNKVTYVGGHIYGSGLNVHQNAINKGKHVWMT
EYYINGQTDITACMTIAKNISDCMNNQMSTYFWWWVNDNDTNVNLVTNSGTIFKNGYTIG
QFAKWVRPGKVRIAATYNPSSGVYLTAYRNGGIVLVAVNTSTSAVSQSFTLQNITGLSSF
NVTQTSSSQNMANLASVAVTGNAFTYTLPAQSVTTFHQY

Figure 18

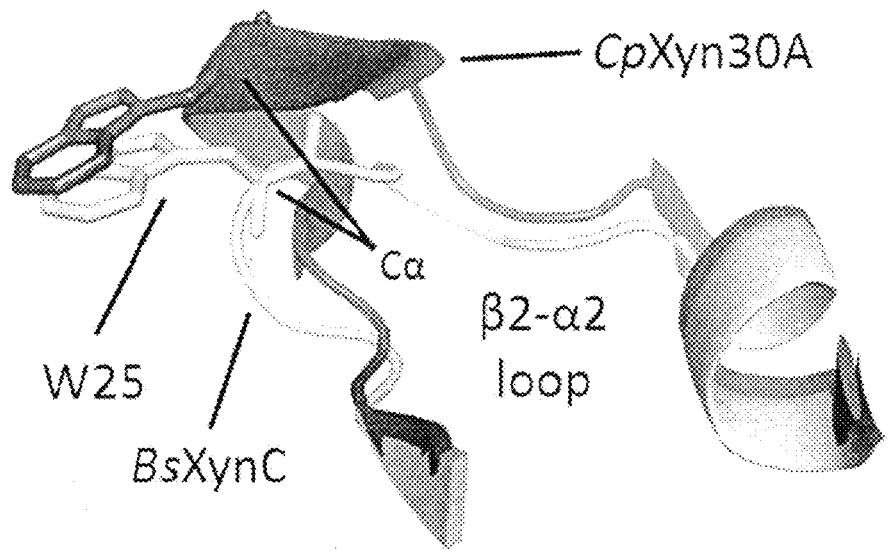

SEQUENCE LISTING

```
<160> NUMBER OF SEQ ID NOS: 80

<210> SEQ ID NO 1
<211> LENGTH: 586
<212> TYPE: PRT
<213> ORGANISM: Clostridium acetobutylicum
<220> FEATURE:
<221> NAME/KEY: 33-420Residues
<222> LOCATION: (33)..(420)

<400> SEQUENCE: 1

Met Asn Ile Lys Leu Lys Arg Thr Leu Ile Ser Leu Val Ala Phe Ser
1               5                   10                  15

Met Thr Cys Leu Pro Phe Val Gly Thr Gly Ser Ser Val Lys Ala Ala
            20                  25                  30

Ser Asn Asp Ala Thr Ile Asn Val Ala Ala Lys His Gln Thr Ile Arg
        35                  40                  45

Gly Phe Gly Ala Ser Ser Ala Trp Cys Gly Ala Leu Ser Asp Thr Cys
    50                  55                  60

Met Asp Thr Leu Tyr Lys Asn Ala Gly Leu Asp Ile Leu Arg Val Arg
65                  70                  75                  80

Ile Ala Pro Asn Glu Gly Trp Asn Arg Gly Asp Tyr Arg Ala Trp Ala
                85                  90                  95

Asp Glu Leu Ser Asn Ala Lys Lys Val Arg Ala Arg Gly Gly Ile Val
            100                 105                 110

Phe Ala Thr Pro Trp Thr Pro Pro Ala Ser Met Lys Thr Asn Asn Thr
        115                 120                 125

Thr Thr Gly Ala Asn Lys Gly Ser Leu Lys Pro Ser Ser Tyr Ala Ala
    130                 135                 140

Tyr Ala Ala Tyr Leu Lys Thr Phe Val Lys Tyr Met Ser Asp Asn Gly
145                 150                 155                 160
```

```
Ala Pro Leu Tyr Ala Leu Ser Leu Gln Asn Glu Pro Asp Trp Ala Pro
                165                 170                 175

Asp Tyr Asp Ala Cys Thr Trp Thr Ala Gln Gln Phe His Asp Phe Leu
            180                 185                 190

Lys Gln Tyr Gly Ala Ser Leu Ser Ser Thr Ile Lys Ile Ile Met Pro
        195                 200                 205

Glu Ser Leu Gly Phe Asn Pro Ala Met Ser Asp Pro Thr Leu Asn Asp
    210                 215                 220

Pro Thr Thr Ala Gln Tyr Val Ser Ile Ile Gly His Leu Tyr Gly
225                 230                 235                 240

Ser Pro Ile Arg Asp Tyr Pro Leu Ala Arg Asn Lys Gly Lys Asp Ile
                245                 250                 255

Trp Met Thr Glu His Tyr Leu Glu Gly Asn Asp Pro Gly Thr Cys Val
            260                 265                 270

Lys Leu Ala Lys Glu Ile His Asp Cys Met Thr Ile Gly Asn Met Asn
        275                 280                 285

Ala Tyr Val Tyr Trp Trp Ile Ser Gly Asp Gln Asn Gly Leu Tyr Asn
    290                 295                 300

Thr Arg Thr Asn Glu Thr Tyr Lys Lys Thr Tyr Val Met Gly Gln Phe
305                 310                 315                 320

Ser Lys Phe Ile Gly Asn Gly Tyr Ser Arg Val Asp Ala Thr Asn Ser
                325                 330                 335

Pro Gln Ser Asn Val Tyr Val Ser Ala Tyr Thr Gly Asn Asn Lys Val
            340                 345                 350

Val Ile Val Ala Ile Asn Gln Gly Thr Tyr Pro Val Asn Gln Ser Phe
        355                 360                 365

Asn Val Gln Asn Ser Thr Val Ser Asn Val Ser Ser Trp Val Ser Ser
    370                 375                 380

Gly Thr Leu Asn Met Ala Lys Thr Asn Ser Asn Ile Ser Ala Ala Asn
385                 390                 395                 400

Gly Arg Phe Asn Ala Ser Leu Pro Ala Gln Ser Val Thr Thr Phe Val
                405                 410                 415

Ala Asp Leu Asn Ser Thr Asn Pro Thr Thr Asp Pro Thr Thr Asn Pro
            420                 425                 430

Thr Pro Gly Ser Thr Val Thr Leu Asn Asn Gly Trp Tyr Tyr Ile Lys
        435                 440                 445

Asn Ile Asn Ala Gln Lys Tyr Leu Gln Val Ala Ser Asn Thr Gly Lys
    450                 455                 460

Ala Gly Gln Asn Val Glu Leu Gly Ser Gly Ser Ala Ala Gly Gln
465                 470                 475                 480

Lys Trp Tyr Leu Thr Asn Thr Gly Asp Gly Tyr Val Thr Leu Lys Ser
                485                 490                 495

Ala Leu Gly Asn Tyr Met Leu Asp Val Ser Tyr Gly Glu Asn Lys Asp
            500                 505                 510

Gly Ser Asn Ile Gln Ile Phe Asn Ala Tyr Ser Gly Asp Ala Gln Lys
        515                 520                 525

Phe Ser Val Lys Ala Ser Ser Lys Asp Gly Gln Tyr Phe Val Ser Thr
    530                 535                 540

Lys Ser Ser Asn Gly Thr Lys Val Leu Asp Asp Tyr Asn Phe Gly Thr
545                 550                 555                 560

Ala Asp Gly Thr Asn Val Cys Gln Trp Thr Tyr Gly Gly Asn Ala Asn
                565                 570                 575
```

```
              Gln Leu Trp Ala Phe Glu Pro Thr Asn Asn
                      580                 585

<210> SEQ ID NO 2
<211> LENGTH: 628
<212> TYPE: PRT
<213> ORGANISM: Clostridium papyrosolvens

<400> SEQUENCE: 2

Met Phe Lys Asn Met Lys Lys Thr Ile Ser Lys Val Leu Val Ser Ser
1               5                   10                  15

Ile Ile Met Ser Ala Leu Phe Met Val Ser Ala Pro Ala Gly Val Ser
                20                  25                  30

Ala Ala Ser Asp Val Thr Val Asn Leu Gly Ser Thr Lys Gln Glu Ile
            35                  40                  45

Arg Gly Phe Gly Ala Ser Ala Trp Cys Gly Thr Ile Ser Asp Tyr
    50                  55                  60

Val Met Asn Ser Leu Tyr Gly Asp Leu Gly Tyr Ser Ile Leu Arg Leu
65                  70                  75                  80

Arg Ile Glu Glu Gly Ile Gly Asp Ala Trp Lys Thr Gly Asn Phe Ser
                85                  90                  95

Lys Trp Ser Pro Glu Leu Ala Asn Ala Lys Lys Ala Ser Ala Lys Gly
            100                 105                 110

Ala Ile Val Phe Ala Ser Pro Trp Asn Pro Pro Ala Ser Met Gln Glu
        115                 120                 125

Asn Phe Ser Lys Ser Gly Asp Ser Ser Ala Gln Arg Leu Arg Tyr Asp
130                 135                 140

Lys Tyr Thr Glu Tyr Ala Gln Tyr Leu Asn Ala Tyr Val Lys Tyr Met
145                 150                 155                 160

Lys Asp Asn Gly Val Asp Leu Tyr Ala Ile Ser Val Gln Asn Glu Pro
                165                 170                 175

Asp Tyr Ala Gln Asp Trp Thr Trp Trp Thr Pro Gln Glu Met Leu Asn
            180                 185                 190

Phe Met Lys Asn Asn Ala Gly Ser Ile Asn Cys Arg Val Met Ala Pro
        195                 200                 205

Glu Ser Phe Gln Phe Leu Lys Asn Met Ser Asp Pro Ile Leu Asn Asp
210                 215                 220

Ala Thr Ala Leu Asp Asn Met Asp Val Leu Gly Cys His Phe Tyr Gly
225                 230                 235                 240

Thr Ser Val Asn Asn Met Ala Tyr Pro Leu Tyr Gln Gln Lys Ser Ala
                245                 250                 255

Gly Lys Glu Leu Trp Met Thr Glu Lys Tyr Phe Asp Asp Thr Thr
            260                 265                 270

Gly Asn Ile Met Asn Met Ser Lys Glu Ile His Asp Ser Met Val Thr
        275                 280                 285

Gly Asn Met Asn Ala Tyr Ile Tyr Trp Trp Ile Thr Trp Pro Asn Gly
    290                 295                 300

Leu Ala Thr Ser Ser Gly Thr Ile Tyr Lys Arg Ala Tyr Val Leu Gly
305                 310                 315                 320

Gln Phe Ala Lys Phe Ile Arg Pro Gly Tyr Lys Arg Val Asp Ala Thr
                325                 330                 335

Ala Thr Pro Asn Thr Asn Val Tyr Val Ser Ala Tyr Thr Gly Asp Asn
            340                 345                 350

Lys Ala Val Ile Val Ala Ile Asn Thr Gly Thr Ala Ala Val Ser Gln
        355                 360                 365
```

```
Lys Phe Asn Phe Gln Asn Gly Ser Ala Ser Val Ser Tyr Val
    370                 375                 380

Thr Asp Ser Ser Arg Asn Met Ala Ala Gly Ala Asn Ile Ala Val Thr
385                 390                 395                 400

Asn Gly Ser Phe Thr Ala Gln Leu Pro Ala Gln Ser Ile Thr Thr Phe
            405                 410                 415

Val Gly Asn Thr Ala Pro Val Val Glu Pro Ile Asp Ala Phe Asn
            420                 425                 430

Lys Ile Glu Ala Glu Asn Tyr Tyr Asp Gln Ser Gly Thr Gln Thr Glu
        435                 440                 445

Ala Asn Ser Asp Gly Asn Gly Lys Asn Val Gly Tyr Ile Glu Asn Glu
    450                 455                 460

Asp Tyr Leu Val Phe Lys Asn Val Asp Phe Gly Ser Gly Ala Ala Ser
465                 470                 475                 480

Phe Glu Ala Ser Ala Gly Ser Ala Thr Asn Gly Gly Asn Ile Glu Leu
            485                 490                 495

Arg Leu Asp Ser Leu Thr Gly Thr Leu Ile Gly Asn Cys Ala Val Pro
        500                 505                 510

Gly Thr Gly Gly Trp Gln Thr Trp Thr Asn Ala Thr Cys Asn Val Ser
    515                 520                 525

Gln Val Thr Gly Lys His Asp Val Tyr Leu Lys Phe Thr Gly Glu Ser
530                 535                 540

Gly Tyr Leu Met Asn Leu Asp Trp Phe Lys Phe Asn Thr Lys Val Ile
545                 550                 555                 560

Pro Val Gly Lys Leu Gly Asp Ile Asn Gly Asp Ala Ser Ile Asp Ser
            565                 570                 575

Leu Asp Leu Met Leu Ile Lys Lys His Leu Leu Gly Glu Ala Ile Glu
        580                 585                 590

Asn Thr Ala Leu Ala Asp Leu Asp Gly Ser Gly Ala Val Asp Ala Ile
    595                 600                 605

Asp Leu Ala Gln Met Lys Gln Tyr Leu Leu Gly Ile Ile Ser Ala Phe
610                 615                 620

Pro Gly Lys Ala
625

<210> SEQ ID NO 3
<211> LENGTH: 423
<212> TYPE: PRT
<213> ORGANISM: Paludibacter propionicigenes

<400> SEQUENCE: 3

Met Thr Gln Lys Leu Ile Gly Tyr Leu Ser Ile Ala Cys Ile Val Phe
1               5                   10                  15

Thr Ala Ser Cys Ser Lys Ser Glu Asn Ser Pro Ile Tyr Thr Pro Pro
            20                  25                  30

Pro Thr Val Asn Asp Thr Val Pro Ser Thr Thr Ala Gly Asn Ala Ile
            35                  40                  45

Leu Asn Leu Thr Asp Glu Gln Gln Val Ile Asp Gly Phe Gly Gly Ser
        50                  55                  60

Thr Ala Trp Asn Gly Ala Leu Ser Asp Ala Gln Ala Asp Ala Leu Phe
65                  70                  75                  80

Gly Asn Ser Asp Asn Ser Gln Met Gly Leu Ser Ile Cys Arg Leu Arg
                85                  90                  95

Ile Asp Pro Asn Lys Tyr Trp Asp Gln Glu Lys Ser Asn Ala Gln Lys
```

```
            100                 105                 110
Ala Asn Ala Arg Gly Ala Lys Val Phe Ala Ser Pro Trp Ser Pro Pro
            115                 120                 125

Val Thr Met Lys Thr Asn Asn Val Val Gln Gly Ala Leu Asp Pro
            130                 135             140

Thr Lys Tyr Ala Asp Tyr Ala Leu Tyr Leu Lys Ser Phe Gly Asp Tyr
145                 150                 155                 160

Ile Lys Asn Ala Gly Val Thr Leu Thr Ala Ile Ser Ile Gln Asn Glu
                165                 170                 175

Pro Asp Trp Lys Pro Asp Tyr Glu Ser Cys Ser Trp Thr Gly Glu Glu
            180                 185                 190

Ile Ala Lys Phe Ala Lys Glu Asn Ala Pro Ala Val Gly Tyr Pro Leu
            195                 200                 205

Met Ile Gly Glu Ser Leu Asn Phe Asn Pro Thr Met Ala Asp Pro Thr
            210                 215                 220

Leu Asn Asp Glu Ala Ala Cys Ala Asn Val Ser Tyr Ile Gly Gly His
225                 230                 235                 240

Leu Tyr Gly Arg Asp Pro Phe Lys Tyr Thr Asn Ala Ile Asp Lys Gly
                245                 250                 255

Lys Lys Ile Trp Met Thr Glu His Tyr Tyr Asp Asn Ala Asn Asn Asn
            260                 265                 270

Ile Ser Val Ala Leu Ser Val Ala Lys Glu Ile Asn Ala Cys Met Asn
            275                 280                 285

Leu Asn Met Asn Ala Tyr Val Trp Trp Trp Val Leu Pro Leu Asn Gly
            290                 295                 300

Ser Ile Cys Asn Leu Ile Asn Glu Asn Lys Ala Met Thr Lys Asn Gly
305                 310                 315                 320

Cys Ala Leu Ala Gln Tyr Ser Lys Trp Val Arg Pro Gly Phe Lys Arg
                325                 330                 335

Val Tyr Ile Thr Pro Glu Pro Tyr Thr Gly Ile Cys Met Ser Ala Tyr
            340                 345                 350

Lys Asn Gly Asn Lys Thr Val Ile Val Ile Val Asn Ser Cys Val Val
            355                 360                 365

Ala Ile Lys Gln Pro Ile Thr Ile Gln Asn Gly Thr Ile Thr Ala Phe
            370                 375                 380

Thr Pro Tyr Glu Thr Thr Ala Thr Lys Asn Val Ala Ala Leu Ser Lys
385                 390                 395                 400

Ile Ala Val Asn Asn Gly Thr Phe Ser Val Asn Leu Lys Gly Gln Ser
                405                 410                 415

Ile Thr Thr Leu Val Ser Glu
            420

<210> SEQ ID NO 4
<211> LENGTH: 399
<212> TYPE: PRT
<213> ORGANISM: Mucilaginibacter paludis

<400> SEQUENCE: 4

Met Lys Lys Asn Leu Leu Gly Leu Leu Gly Leu Leu Ala Ile Met Gly
1               5                   10                  15

Ser Cys Ser Lys Asn Ser Ile Gln Gln Lys Ala Ser Gln Glu Glu Thr
                20                  25                  30

Leu Lys Gly Thr Ala Val Ile Asp Gly Gly Thr Leu Tyr Gln Ala Ile
            35                  40                  45
```

Asp Gly Ile Gly Phe Ser Ser Ala Trp Cys Gly Gln Leu Ser Thr Ala
            50                  55                  60

Lys Asn Asn Ala Leu Tyr Gly Thr Leu Gly Met Ser Leu Leu Arg Val
 65                  70                  75                  80

Arg Ile Asp Gln Asn Ser Ala Asn Trp Ala Asp Glu Thr Ala Asn Ser
                85                  90                  95

Ala Ala Ala His Ala Ala Gly Val Lys Val Leu Gly Ser Glu Trp Ser
            100                 105                 110

Pro Pro Val Ala Trp Thr Ser Asn Gly Gln Ser Thr Gly Gly Tyr Leu
            115                 120                 125

Leu Pro Gln Tyr Tyr Ala Asn Tyr Ala Ser Tyr Leu Asn Gln Ala Ala
130                 135                 140

Thr Asn Ile Gly Leu Asp Phe Val Ser Phe Gln Asn Glu Pro Asp Ile
145                 150                 155                 160

Ser Gly Ala Val Leu Trp Thr Pro Ala Gln Ile Leu Thr Phe Val Lys
                165                 170                 175

Asn Asn Ser Ala Thr Ile Gly Lys Pro Ile Val Met Pro Glu Ser Phe
            180                 185                 190

His Phe Asp Asp Ala Tyr Ser Asp Pro Val Leu Asn Asp Ala Asp Ala
            195                 200                 205

Val Asn Lys Val Thr Tyr Val Gly His Ile Tyr Gly Ser Gly Leu
210                 215                 220

Asn Val His Gln Asn Ala Ile Asn Lys Gly Lys His Val Trp Met Thr
225                 230                 235                 240

Glu Tyr Tyr Ile Asn Gly Gln Thr Asp Ile Thr Ala Cys Met Thr Ile
                245                 250                 255

Ala Lys Asn Ile Ser Asp Cys Met Asn Asn Gln Met Ser Thr Tyr Phe
            260                 265                 270

Trp Trp Trp Val Asn Asp Asn Asp Thr Asn Val Asn Leu Val Thr Asn
            275                 280                 285

Ser Gly Thr Ile Phe Lys Asn Gly Tyr Thr Ile Gly Gln Phe Ala Lys
290                 295                 300

Trp Val Arg Pro Gly Lys Val Arg Ile Ala Ala Thr Tyr Asn Pro Ser
305                 310                 315                 320

Ser Gly Val Tyr Leu Thr Ala Tyr Arg Asn Gly Gly Ile Val Leu Val
                325                 330                 335

Ala Val Asn Thr Ser Thr Ser Ala Val Ser Gln Ser Phe Thr Leu Gln
            340                 345                 350

Asn Ile Thr Gly Leu Ser Ser Phe Asn Val Thr Gln Thr Ser Ser Ser
            355                 360                 365

Gln Asn Met Ala Asn Leu Ala Ser Val Ala Val Thr Gly Asn Ala Phe
370                 375                 380

Thr Tyr Thr Leu Pro Ala Gln Ser Val Thr Thr Phe His Gln Tyr
385                 390                 395

<210> SEQ ID NO 5
<211> LENGTH: 389
<212> TYPE: PRT
<213> ORGANISM: Bacillus subtilis

<400> SEQUENCE: 5

Ala Ala Ser Asp Val Thr Val Asn Val Ser Ala Glu Lys Gln Val Ile
1               5                   10                  15

Arg Gly Phe Gly Gly Met Asn His Pro Ala Trp Ala Gly Asp Leu Thr
            20                  25                  30

Ala Ala Gln Arg Glu Thr Ala Phe Gly Asn Gly Gln Asn Gln Leu Gly
        35                  40                  45

Phe Ser Ile Leu Arg Ile His Val Asp Glu Asn Arg Asn Asn Trp Tyr
 50                  55                  60

Lys Glu Val Glu Thr Ala Lys Ser Ala Val Lys His Gly Ala Ile Val
 65                  70                  75                  80

Phe Ala Ser Pro Trp Asn Pro Pro Ser Asp Met Val Glu Thr Phe Asn
                 85                  90                  95

Arg Asn Gly Asp Thr Ser Ala Lys Arg Leu Lys Tyr Asn Lys Tyr Ala
             100                 105                 110

Ala Tyr Ala Gln His Leu Asn Asp Phe Val Thr Phe Met Lys Asn Asn
         115                 120                 125

Gly Val Asn Leu Tyr Ala Ile Ser Val Gln Asn Glu Pro Asp Tyr Ala
     130                 135                 140

His Glu Trp Thr Trp Thr Pro Gln Glu Ile Leu Arg Phe Met Arg
145                 150                 155                 160

Glu Asn Ala Gly Ser Ile Asn Ala Arg Val Ile Ala Pro Glu Ser Phe
                165                 170                 175

Gln Tyr Leu Lys Asn Leu Ser Asp Pro Ile Leu Asn Asp Pro Gln Ala
            180                 185                 190

Leu Ala Asn Met Asp Ile Leu Gly Thr His Leu Tyr Gly Thr Gln Val
        195                 200                 205

Ser Gln Phe Pro Tyr Pro Leu Phe Lys Gln Lys Gly Ala Gly Lys Asp
    210                 215                 220

Leu Trp Met Thr Glu Val Tyr Tyr Pro Asn Ser Asp Thr Asn Ser Ala
225                 230                 235                 240

Asp Arg Trp Pro Glu Ala Leu Asp Val Ser Gln His Ile His Asn Ala
                245                 250                 255

Met Val Glu Gly Asp Phe Gln Ala Tyr Val Trp Trp Tyr Ile Arg Arg
            260                 265                 270

Ser Tyr Gly Pro Met Lys Glu Asp Gly Thr Ile Ser Lys Arg Gly Tyr
        275                 280                 285

Asn Met Ala His Phe Ser Lys Phe Val Arg Pro Gly Tyr Val Arg Ile
    290                 295                 300

Asp Ala Thr Lys Asn Pro Asn Ala Asn Val Tyr Val Ser Ala Tyr Lys
305                 310                 315                 320

Gly Asp Asn Lys Val Val Ile Val Ala Ile Asn Lys Ser Asn Thr Gly
                325                 330                 335

Val Asn Gln Asn Phe Val Leu Gln Asn Gly Ser Ala Ser Asn Val Ser
            340                 345                 350

Arg Trp Ile Thr Ser Ser Ser Asn Leu Gln Pro Gly Thr Asn Leu
        355                 360                 365

Thr Val Ser Gly Asn His Phe Trp Ala His Leu Pro Ala Gln Ser Val
    370                 375                 380

Thr Thr Phe Val Val
385

<210> SEQ ID NO 6
<211> LENGTH: 384
<212> TYPE: PRT
<213> ORGANISM: Serratia sp. E-15

<400> SEQUENCE: 6

His Ala Ser Thr Val Asn Ile Asn Thr Asp Val Gly Tyr Gln Val Val

```
1               5                   10                  15
Arg Gly Phe Gly Gly Met Asn Gly Pro Gly Trp Ile Asn Asp Leu Thr
                20                  25                  30

Thr Ala Gln Val Asn Thr Ala Phe Gly Asn Asp Ser Gly Gln Met Gly
        35                  40                  45

Leu Ser Ile Met Arg Met Arg Ile Asp Pro Asp Ser Ser His Trp Asn
            50                  55                  60

Leu Gln Val Ala Ser Ala Ser Lys Ala Tyr Ala Leu Gly Ala Thr Leu
65                  70                  75                  80

Met Ala Thr Pro Trp Ser Pro Pro Ala Tyr Met Lys Ser Asn Asn Ser
                85                  90                  95

Leu Ile Asn Gly Gly Thr Leu Leu Pro Ser Tyr Tyr Ser Tyr Thr
                100                 105                 110

Thr His Leu Leu Asn Phe Ala Ser Tyr Met Lys Thr Asn Gly Ala Pro
            115                 120                 125

Leu Tyr Ala Ile Ser Ile Gln Asn Glu Pro Asp Trp Gln Pro Ala Tyr
130                 135                 140

Glu Ser Cys Glu Trp Ser Gly Asp Asp Phe Lys Asn Tyr Ile Lys Ser
145                 150                 155                 160

Gln Gly Ser Arg Phe Gly Ser Leu Asn Val Ile Ala Glu Ser Leu
                165                 170                 175

Asn Phe Asn His Ser Leu Thr Asp Pro Val Leu Asn Asp Ser Thr Ala
            180                 185                 190

Ser Gln Tyr Val Ser Ile Ile Gly Gly His Leu Tyr Gly Thr Thr Pro
                195                 200                 205

Thr Ala Tyr Pro Leu Ala Arg Asn Ala Gly Lys Gln Val Trp Met Thr
    210                 215                 220

Glu His Leu Ile Asp Glu Lys Gln Ser Gly Asn Asp Trp Thr Ser Ala
225                 230                 235                 240

Leu Asn Val Ala Asn Glu Leu His Asn Ser Met Val Ala Asn Phe Asn
                245                 250                 255

Ala Tyr Val Trp Trp Tyr Ile Arg Arg Ser Tyr Gly Leu Met Thr Glu
            260                 265                 270

Asp Gly Asn Ile Ser Lys Arg Gly Tyr Val Met Ser Gln Tyr Ala Lys
        275                 280                 285

Phe Val Arg Pro Gly Phe Gln Arg Ile Gln Ala Thr Glu Asn Pro Gln
    290                 295                 300

Ser Asn Val His Leu Thr Ala Tyr Lys Gly Ala Ser Asn Asp Lys Leu
305                 310                 315                 320

Val Ile Val Ala Val Asn Thr Asn Asp Ser Asn Gln Ser Leu Thr Leu
                325                 330                 335

Asn Ile Thr Asn Ser Asn Val Ser Ala Leu Lys Lys Tyr Ser Thr Ser
            340                 345                 350

Ala Thr Leu Asn Val Gly Tyr Gly Gly Asn Thr Pro Leu Ser Ser Gly
        355                 360                 365

Lys Ala Thr Leu Trp Leu Asn Pro Lys Ser Val Thr Phe Val Ser
    370                 375                 380
```

<210> SEQ ID NO 7
<211> LENGTH: 382
<212> TYPE: PRT
<213> ORGANISM: Cystobacter fuscus

<400> SEQUENCE: 7

```
Ser Ala Gln Asp Ile Val Ile Asp Pro Ser Lys Thr His Gln Val Ile
  1               5                  10                  15
Arg Gly Phe Gly Gly Met Asn Gly Pro Gly Trp Ile Asp Leu Thr
             20                  25                  30
Pro Ala Gln Ile Asp Leu Ala Phe Gly Ser Asp Val Gly Gln Leu Gly
             35                  40                  45
Leu Ser Ile Met Arg Met Arg Ile Asp Pro Ser Asn Ser Arg Trp Asn
 50                  55                  60
Leu Gln Val Pro Ser Ala Arg Ala Arg Ala Lys Gly Val Leu Leu
 65                  70                  75                  80
Leu Gly Ser Pro Trp Thr Pro Ala Tyr Met Lys Ser Asn Asn Asn
                 85                  90                  95
Leu Asn Asn Gly Gly Lys Leu Leu Pro Gln Tyr Tyr Glu Ala Tyr Ala
                100                 105                 110
Thr His Leu Leu Gly Phe Ala Ser Tyr Met Ala Asn Asn Ala Ser
         115                 120                 125
Leu Tyr Ala Ile Ser Leu Gln Asn Glu Pro Asp Trp His Pro Asp Tyr
        130                 135                 140
Glu Ser Ala Asp Trp Ser Gly Thr Asp Phe Val Asn Phe Leu Asn Ala
145                 150                 155                 160
Gln Gly Ala Arg Phe Gly Thr Leu Lys Val Leu Ala Ser Glu Ser Leu
                165                 170                 175
Asn Phe Asn Pro Ala Val Thr Asp Pro Ile Leu Asn Ser Ala Thr Ala
                180                 185                 190
Ser Gln His Val Asp Ile Val Gly Gly His Leu Tyr Gly Val Gln Pro
        195                 200                 205
Lys Asp Tyr Pro Leu Ala Arg Ser Lys Gly Lys Glu Leu Trp Met Thr
210                 215                 220
Glu His Tyr Thr Asp Asn Thr Asp Gly Asn Val Trp Pro Ser Ala Leu
225                 230                 235                 240
Glu Val Gly Ser Glu Leu His Lys Ser Met Val Ala Asn Tyr Ser Gly
                245                 250                 255
Tyr Ile Trp Trp Tyr Ile Arg Arg Ser Tyr Gly Leu Ile Ser Glu Asn
                260                 265                 270
Gly Ser Val Ser Lys Arg Gly Tyr Val Met Ser Gln Phe Ala Arg Phe
        275                 280                 285
Val Arg Pro Gly Ser Val Arg Ile Gly Thr Thr Glu Lys Pro Tyr Ser
        290                 295                 300
Asp Val Tyr Ala Thr Ala Tyr Ala Thr Pro Asp Gly Lys Ile Val Leu
305                 310                 315                 320
Val Val Val Asn Thr Thr Gln His Arg Val Leu Asn Val Ser Val
                325                 330                 335
Pro Ser Gly Arg Val Ala Arg Phe Thr Lys Tyr Gly Thr Ser Ser Ser
                340                 345                 350
Leu Asn Val Gly Tyr Gly Gly Tyr Gln Ala Gln Asn Gly Lys Ala
        355                 360                 365
Ser Phe Tyr Val Asp Pro Gln Ser Ile Ala Thr Phe Val Gly
        370                 375                 380

<210> SEQ ID NO 8
<211> LENGTH: 382
<212> TYPE: PRT
<213> ORGANISM: Xanthomonas campestris

<400> SEQUENCE: 8
```

```
Ala Ala Gln Thr Val Thr Val Asn Pro Asn Gln Thr Tyr Gln Thr Val
1               5                   10                  15

Arg Gly Phe Gly Met Asn Gly Ala Gly Trp Ile Asn Asn Leu Thr
            20                  25                  30

Pro Ala Gln Val Asp Leu Ala Tyr Gly Ser Gly Asn Gly Gln Ile Gly
            35                  40                  45

Leu Ser Ile Leu Arg Met Arg Ile Asp Pro Ser Ser Ser Gly Trp Ser
50                  55                  60

Leu Gln Val Pro Thr Ala Ala Arg Val Arg Ala Leu Gly Gly Ile Leu
65                  70                  75                  80

Phe Ala Thr Pro Trp Ser Pro Pro Ala Tyr Met Lys Ser Asn Lys Ser
                85                  90                  95

Leu Val Lys Gly Gly Lys Leu Leu Ser Thr Ser Tyr Ala Ala Tyr Thr
            100                 105                 110

Thr His Leu Leu Asp Phe Ala Asn Tyr Leu Ser Ala Arg Asn Ala Pro
            115                 120                 125

Leu Tyr Ala Ile Ser Leu Gln Asn Glu Pro Asp Trp His Pro Asp Tyr
130                 135                 140

Glu Ser Ala Asp Trp Asn Gly Ser Asp Phe Val Asn Tyr Leu Asn Ala
145                 150                 155                 160

Glu Gly Gly Lys Phe Gly Ala Leu Lys Val Ile Val Gly Glu Ser Val
                165                 170                 175

Gly Phe Thr Phe Ser Ile Thr Asp Pro Val Leu Asn Asn Ala Lys Ala
            180                 185                 190

Ser Gln Ala Thr Ser Ile Val Ala Gly His Leu Tyr Gly Ala Gln Pro
            195                 200                 205

Lys Asp Tyr Ala Leu Ala Arg Ser Lys Gly Lys Gln Val Trp Met Thr
210                 215                 220

Glu His Tyr Thr Asp Thr Ser Asp Gly Asn Ala Trp Pro Ser Ala Leu
225                 230                 235                 240

Gly Val Ala Ser Glu Leu His Gln Ser Met Val Ala Asn Tyr Asn Ala
                245                 250                 255

Tyr Ile Trp Trp Tyr Ile Arg Arg Ser Tyr Gly Leu Ile Ser Glu Gly
            260                 265                 270

Gly Ser Val Ser Lys Arg Gly Tyr Val Met Ser Gln Phe Ala Arg Phe
            275                 280                 285

Val Arg Pro Gly Ser Val Arg Ile Gly Ala Thr Glu His Pro Tyr Ala
290                 295                 300

Asp Val Ser Thr Thr Ala Tyr Arg Thr Pro Asp Asn Lys Ile Val Val
305                 310                 315                 320

Val Ala Val Asn Thr Gly Thr Ala His Gln Arg Leu Asp Leu Thr Val
                325                 330                 335

Pro Ala Gly Ala Ala Thr Gln Phe Val Lys Tyr Thr Thr Ser Ser Ser
            340                 345                 350

Leu Asn Ala Gly Tyr Ala Gly Ala Tyr Thr Val Ser Gly Gly Lys Thr
            355                 360                 365

Ser Leu Tyr Ile Asp Pro Gln Ser Ile Ala Thr Leu Val Gly
            370                 375                 380

<210> SEQ ID NO 9
<211> LENGTH: 384
<212> TYPE: PRT
<213> ORGANISM: Cellvibrio japonicus
```

<400> SEQUENCE: 9

```
Leu Ala Gln Thr Ile Asn Val Asn Ala Ala Thr Glu Tyr Gln Thr Ile
1               5                   10                  15

Arg Gly Phe Gly Gly Met Asn Gly Val Gly Trp Ile Asn Asp Leu Thr
            20                  25                  30

Thr Ser Gln Leu Glu Thr Ala Phe Gly Ser Asp Gln Gly Gln Leu Gly
        35                  40                  45

Leu Ser Ile Met Arg Met Arg Ile Asp Pro Asn Ser Ala Asn Trp Arg
    50                  55                  60

Leu Gln Val Pro Ala Ala Val Arg Ala Arg Gln Leu Gly Ala Ile Leu
65                  70                  75                  80

Leu Ala Ser Pro Trp Ser Pro Pro Ala His Met Lys Ser Asn Lys Ser
                85                  90                  95

Leu Ile Asn Gly Gly Lys Leu Leu Pro Glu Tyr Tyr Gly Asp Tyr Ala
            100                 105                 110

Thr His Leu Leu Gly Phe Ala Asp His Met Ser Arg Asn Gly Ala Pro
        115                 120                 125

Leu His Ala Ile Ser Leu Gln Asn Glu Pro Asp Trp His Pro Asp Tyr
    130                 135                 140

Glu Ser Cys Asp Trp Asn Gly Asn Asp Phe Val Asn Phe Leu Asn Ala
145                 150                 155                 160

Gln Gly Ser Arg Phe Gly Ala Asp Leu Gln Val Ala Val Gly Glu Ala
                165                 170                 175

Val Gly Phe Thr Lys Arg Phe Thr Asp Pro Val Leu Asn Ser Pro Thr
            180                 185                 190

Ala Val Gln His Ala Asp Ile Ile Ala Gly His Leu Tyr Gly Ala Val
        195                 200                 205

Pro Gln Asp Tyr Pro Leu Ala Arg Ser Lys Gly Lys Glu Val Trp Met
    210                 215                 220

Thr Glu His Tyr Thr Asp Ser Lys Asn Asp Ala Asp Val Trp Pro Leu
225                 230                 235                 240

Ala Leu Asp Val Gly Val Glu Leu His Arg Ser Met Ala Ala Asn Phe
                245                 250                 255

Asn Ala Tyr Ile Trp Trp Tyr Ile Arg Arg Phe Tyr Ser Phe Ile Lys
            260                 265                 270

Glu Asp Gly Gln Val Ser Lys Arg Gly Tyr Ile Met Ser Gln Tyr Ala
        275                 280                 285

Arg Phe Val Arg Pro Gly Phe Lys Arg Ile Gly Ala Thr Glu Asn Pro
    290                 295                 300

Tyr Ser Asp Val Met Val Thr Ala Tyr Lys Gly Pro Asp Asn Lys Ile
305                 310                 315                 320

Val Met Val Val Asn Asn Gly Asn Ala Ser Arg Asn Leu Asn Val
                325                 330                 335

Asn Leu Gln Asn Ala Thr Val Ala Ser Phe Val Lys Tyr Ser Thr Ser
            340                 345                 350

Asp Thr Leu Asn Val Ser Tyr Gly Gly Ala Tyr Arg Met Thr Asn Gly
        355                 360                 365

Ala Thr Ser Phe Trp Val Glu Pro Lys Ser Ile Ala Thr Phe Val Ser
    370                 375                 380

<210> SEQ ID NO 10
<211> LENGTH: 392
<212> TYPE: PRT
<213> ORGANISM: Clostridium thermocellum
```

<400> SEQUENCE: 10

Ala Ala Glu Thr Ala Thr Ile Asn Leu Ser Ala Glu Lys Gln Val Ile
1               5                   10                  15

Arg Gly Phe Gly Gly Met Asn His Pro Val Trp Ile Ser Asp Leu Thr
            20                  25                  30

Pro Gln Gln Arg Asp Thr Ala Phe Gly Asn Gly Glu Gly Gln Leu Gly
                35                  40                  45

Phe Thr Ile Leu Arg Ile His Val Asp Glu Asn Arg Asn Asn Trp Ser
            50                  55                  60

Lys Glu Val Ala Thr Ala Arg Arg Ala Ile Glu Leu Gly Ala Ile Val
65                  70                  75                  80

Phe Ala Ser Pro Trp Asn Pro Pro Ser Asn Met Val Glu Thr Phe Thr
                85                  90                  95

Arg Asn Gly Val Pro Asn Gln Lys Arg Leu Arg Tyr Asp Lys Tyr Gly
            100                 105                 110

Asp Tyr Val Gln His Leu Asn Asp Phe Val Ala Tyr Met Lys Ser Asn
            115                 120                 125

Gly Val Asp Leu Tyr Ala Ile Ser Val Gln Asn Glu Pro Asp Tyr Ala
130                 135                 140

His Glu Trp Thr Trp Trp Ala Pro Gln Glu Met Leu Arg Phe Met Arg
145                 150                 155                 160

Asp Tyr Ala Gly Gln Ile Asn Cys Arg Val Met Ala Pro Glu Ser Phe
                165                 170                 175

Gln Tyr Leu Lys Asn Met Ser Asp Pro Ile Leu Asn Asp Pro Gln Ala
            180                 185                 190

Leu Ala Asn Leu Asp Ile Leu Gly Ala His Phe Tyr Gly Thr Thr Val
            195                 200                 205

Asn Asn Met Pro Tyr Pro Leu Phe Glu Gln Lys Gly Ala Gly Lys Glu
            210                 215                 220

Leu Trp Met Thr Glu Val Tyr Val Pro Asn Ser Asp Ser Asn Ser Ala
225                 230                 235                 240

Asp Arg Trp Pro Glu Ala Leu Glu Val Ala His Asn Met His Asn Ala
                245                 250                 255

Leu Val Glu Gly Asn Phe Gln Ala Tyr Val Trp Trp Tyr Ile Arg Arg
            260                 265                 270

Ser Tyr Gly Pro Met Lys Glu Asp Gly Thr Ile Ser Lys Arg Gly Tyr
            275                 280                 285

Met Met Ala His Tyr Ser Lys Phe Val Arg Pro Gly Tyr Val Arg Val
            290                 295                 300

Asp Ala Thr Lys Asn Pro Thr Tyr Asn Val Tyr Leu Ser Ala Tyr Lys
305                 310                 315                 320

Asn Lys Lys Asp Asn Ser Val Val Ala Val Val Ile Asn Lys Ser Thr
                325                 330                 335

Glu Ala Lys Thr Ile Asn Ile Ser Val Pro Gly Thr Ser Ile Arg Lys
            340                 345                 350

Trp Glu Arg Tyr Val Thr Thr Gly Ser Lys Asn Leu Arg Lys Glu Ser
            355                 360                 365

Asp Ile Asn Ala Ser Gly Thr Thr Phe Gln Val Thr Leu Glu Pro Gln
            370                 375                 380

Ser Val Thr Thr Phe Val Gly Gly
385                 390

```
<210> SEQ ID NO 11
<211> LENGTH: 390
<212> TYPE: PRT
<213> ORGANISM: Clostridium saccharoperbutylacetonicum

<400> SEQUENCE: 11
```

| Ala | Ala | Ser | Asn | Val | Ser | Ile | Asn | Leu | Ser | Glu | Lys | Gln | Val | Val |
|---|---|---|---|---|---|---|---|---|---|---|---|---|---|---|
| 1 | | | | 5 | | | | | 10 | | | | | 15 |

Arg Gly Phe Gly Gly Met Asn Leu Pro Ala Trp Ala Gly Asp Leu Thr
                20                25              30

Ala Gly Gln Arg Glu Thr Ala Phe Gly Asn Gly Glu Asn Gln Leu Gly
        35                40              45

Leu Ser Val Leu Arg Ile Tyr Val Asp Asp Asn Lys Asn Asn Trp Tyr
 50                55              60

Lys Glu Leu Pro Thr Ala Lys Lys Ala Ile Glu His Gly Ala Ile Val
65              70              75              80

Phe Ala Thr Pro Trp Asn Pro Pro Ser Asp Met Thr Glu Thr Phe Asn
                85              90              95

Arg Asn Gly Asp Thr Ser Ala Lys Arg Leu Lys Tyr Asp Lys Tyr Ala
        100              105            110

Ala Tyr Ala Gln His Leu Asn Asp Phe Val Ser Tyr Met Lys Asn Asn
              115            120            125

Gly Val Asn Leu Tyr Ala Ile Ser Ile Gln Asn Glu Pro Asp Tyr Gly
      130              135            140

Lys Glu Trp Thr Trp Thr Pro Gln Glu Val Leu Lys Phe Met Lys
145             150             155            160

Glu Asn Ala Gly Thr Ile Asn Cys Lys Val Met Ser Pro Glu Ser Phe
              165            170            175

Ser Tyr Gln Lys Asn Met Tyr Asn Pro Ile Leu Asn Asp Ser Gln Ala
        180              185            190

Leu Ala Asn Met Asp Ile Leu Gly Thr His Thr Tyr Gly Thr Lys Val
              195            200            205

Ser Asp Phe Ala Tyr Pro Leu Phe Lys Gln Lys Gly Ala Gly Lys Glu
      210            215            220

Leu Trp Met Thr Glu Val Tyr Val Pro Asn Ser Asp Ala Asn Ser Ala
225              230              235            240

Asp Arg Trp Pro Glu Ala Leu Asp Val Ala Glu His Ile Asn Asn Ala
              245            250            255

Met Val Glu Gly Asp Phe Gln Ser Tyr Val Trp Trp Tyr Ile Arg Arg
        260              265            270

Ser Tyr Gly Phe Ile Lys Glu Asp Gly Asn Val Ser Lys Arg Gly Tyr
      275            280            285

Met Met Ala His Phe Ser Lys Phe Val Arg Pro Gly Tyr Val Arg Val
      290            295            300

Asp Ala Thr Lys Asn Pro Thr Asn Val Tyr Val Ser Ala Tyr Lys
305             310            315            320

Gly Asn Asn Lys Val Val Ile Val Val Ile Asn Lys Gly Thr Ser Glu
              325            330            335

Val Lys Gln Ser Phe Asn Val Ser Asn Ser Lys Val Ser Ser Val Ser
        340              345            350

Ser Trp Gln Thr Thr Ala Thr Ala Asn Leu Ala Lys Ser Ala Ser Ser
              355            360            365

Ile Asn Val Ser Asn Gly Ser Phe Thr Ala Thr Leu Pro Ala Gln Ser
      370            375            380

Val Thr Thr Phe Val Gly
385                 390

<210> SEQ ID NO 12
<211> LENGTH: 399
<212> TYPE: PRT
<213> ORGANISM: Ruminococcus sp.

<400> SEQUENCE: 12

Ala Ala Thr Val Cys Lys Ile Asp Pro Thr Ile Gln Tyr Gln Thr Ile
1               5                   10                  15

Arg Gly Phe Gly Gly Ile Asn His Pro Glu Trp Thr Gly Lys Asp Leu
            20                  25                  30

Thr Glu Glu Gln Arg Gln Thr Ala Phe Gly Asn Gly Glu Asp Glu Leu
        35                  40                  45

Gly Leu Thr Val Leu Arg Val Phe Val Asn Pro Asp Gln Ser Gln Trp
    50                  55                  60

Asn Lys Ala Leu Pro Thr Ala Gln Phe Ala Thr Lys Met Gly Val Thr
65                  70                  75                  80

Val Phe Ala Ser Pro Trp Glu Pro Pro Ala Asn Leu Ala Glu Ser Gly
                85                  90                  95

Gly Ser Asn Gly Lys Leu His Leu Pro Lys Ser Asn Tyr Ala Ala Tyr
            100                 105                 110

Ala Lys His Leu Asn Asp Phe Gly Thr Tyr Met Lys Ser Asn Gly Val
        115                 120                 125

Asp Leu Tyr Ala Val Ser Val Gln Asn Glu Pro Asp Tyr Ala Ser Glu
    130                 135                 140

Trp Thr Tyr Trp Ser Thr Asp Glu Thr Thr Asp Phe Ile Ala Asn Tyr
145                 150                 155                 160

Gly Asp Gln Ile Thr Ser Thr Arg Leu Met Ser Pro Glu Ser Phe Gln
                165                 170                 175

Tyr Ala Pro Glu Asn Ala Ser Trp Val Ala Asp Gly Gly Lys Thr Phe
            180                 185                 190

Tyr Arg Lys Ile Leu Asn Asn Ser Lys Ala Met Glu Asn Cys Asp Leu
        195                 200                 205

Phe Gly Thr His Phe Tyr Gly Thr Gln Arg Ala Trp Met Asp Phe Pro
    210                 215                 220

Asp Leu Glu Asn Ser Gly Lys Glu Ile Trp Met Thr Glu Val Tyr Val
225                 230                 235                 240

Pro Asn Ser Glu Gln Asp Ser Ala Asn Arg Tyr Pro Glu Ala Leu Gln
                245                 250                 255

Val Ser Glu Asn Ile His Asn Ala Met Val Val Gly Asn Met Ser Ala
            260                 265                 270

Tyr Thr Trp Trp Tyr Ile Arg His Tyr Gly Leu Met Thr Glu Asp
        275                 280                 285

Gly Lys Ile Ser Lys Arg Gly Tyr Cys Met Ala Gln Tyr Ser Lys Tyr
    290                 295                 300

Val Arg Pro Gly Asp Val Arg Ile Asp Ala Thr Glu Gln Pro Ala Asp
305                 310                 315                 320

Asn Val Tyr Val Ser Ala Tyr Lys Gly Asp Asp Asn Gln Val Thr Ile
                325                 330                 335

Val Ala Ile Asn Lys Gly Thr Glu Ser Tyr Ser Gln Gln Phe Ala Val
            340                 345                 350

Asp Ala Asp Ala Gln Ile Thr Glu Val Asp Arg Tyr Arg Thr Ser Ala
        355                 360                 365

Ser Glu Asn Leu Ala Lys Thr Gly Asn Met Glu His Asp Ser Ser Ser
    370                 375                 380

Phe Trp Ala Gln Leu Pro Ala Glu Ser Val Ser Thr Phe Val Val
385                 390                 395

<210> SEQ ID NO 13
<211> LENGTH: 390
<212> TYPE: PRT
<213> ORGANISM: Paenibacillus sp.

<400> SEQUENCE: 13

Ala Ala Ser Asp Ala Asn Ile Asn Leu Ser Ser Glu Lys Gln Leu Ile
1               5                   10                  15

Lys Gly Phe Gly Gly Ile Asn Leu Pro Ala Trp Ile Gly Asp Leu Thr
            20                  25                  30

Pro Ala Gln Arg Glu Thr Ala Phe Gly Asn Asp Gln Asn Gln Leu Gly
        35                  40                  45

Phe Ser Ile Leu Arg Ile Tyr Val Asp Pro Asp Ser Asn Asn Trp Tyr
    50                  55                  60

Arg Glu Val Ala Thr Ala Lys Arg Ala Ile Glu Lys Gly Ala Ile Val
65                  70                  75                  80

Phe Ala Ser Pro Trp Asn Pro Pro Ser Ser Met Val Glu Thr Phe Asn
                85                  90                  95

Arg Asn Gly Asp Thr Asn Ala Lys Arg Leu Lys Tyr Asp Lys Tyr Thr
            100                 105                 110

Ala Tyr Ala Gln His Leu Asn Asp Phe Val Thr Tyr Met Lys Asn Asn
        115                 120                 125

Gly Val Asp Leu Tyr Ala Ile Ser Val Gln Asn Glu Pro Asp Tyr Ala
    130                 135                 140

His Asp Trp Thr Trp Thr Pro Gln Glu Ile Leu Arg Phe Met Lys
145                 150                 155                 160

Glu Asn Ala Gly Ser Ile Gln Gly Thr Lys Val Met Ala Pro Glu Ser
                165                 170                 175

Phe Gln Tyr Leu Lys Asn Ile Ser Asp Pro Ile Leu Asn Asp Pro Gln
            180                 185                 190

Ala Leu Ala Asn Met Asp Ile Leu Gly Ala His Thr Tyr Gly Thr Gln
        195                 200                 205

Ile Ser Asn Phe Ala Tyr Pro Leu Phe Lys Gln Lys Gly Ala Gly Lys
    210                 215                 220

Glu Leu Trp Met Thr Glu Val Tyr Val Pro Asn Ser Asp Asn Asn Ser
225                 230                 235                 240

Ala Asp Arg Trp Pro Glu Ala Leu Asp Val Ser Tyr His Met His Asn
                245                 250                 255

Ala Met Val Glu Gly Asp Phe Gln Ala Tyr Val Trp Trp Tyr Ile Arg
            260                 265                 270

Arg Gln Tyr Gly Pro Met Lys Glu Asp Gly Thr Ile Ser Lys Arg Gly
        275                 280                 285

Tyr Asn Met Ala His Phe Ser Lys Phe Val Arg Pro Gly Tyr Leu Arg
    290                 295                 300

Val Asp Ala Thr Lys Asn Pro Asp Thr Asn Thr Phe Val Ser Ala Tyr
305                 310                 315                 320

Lys Gly Asp Asn Lys Val Val Val Ala Ile Asn Arg Gly Thr Ser
                325                 330                 335

Ala Thr Ser Gln Lys Phe Val Leu Gln Asn Gly Asn Ala Ser Thr Val

```
            340              345              350
Ser Ser Trp Ile Thr Asp Ser Ser Arg Asn Leu Ala Ser Gly Thr Ser
        355              360              365

Leu Asn Val Ser Asn Gly Ala Phe Thr Ala Gln Leu Pro Pro Gln Ser
    370              375              380

Val Thr Thr Phe Val Ala
385             390

<210> SEQ ID NO 14
<211> LENGTH: 389
<212> TYPE: PRT
<213> ORGANISM: Streptomyces bingchenggensis

<400> SEQUENCE: 14

Ala Ala Ala Thr Val Ile Val Asp Pro Ser Ala Val Arg Gln Thr Ile
1               5                   10                  15

Arg Gly Phe Gly Gly Met Asn His Thr Val Trp Ile Ser Asp Leu Thr
            20                  25                  30

Pro Ala Gln Arg Asp Thr Ala Phe Gly Asn Gly Glu Gly Gln Leu Gly
        35                  40                  45

Phe Ser Val Leu Arg Ile Pro Val His Glu Asn Arg Ala Asp Trp Ser
    50                  55                  60

Arg Glu Val Ala Thr Ala Lys Arg Ala Ile Glu Tyr Gly Ala Ala Val
65                  70                  75                  80

Ile Ala Ser Pro Trp Asn Pro Pro Ala Gln Met Val Glu Thr Phe Val
                85                  90                  95

His Gly Asp Gln Ser Asn Ala Lys Arg Leu Arg Tyr Asp Met Tyr Gly
            100                 105                 110

Ala Tyr Ala Gln His Leu Asn Asp Phe Cys Arg Phe Met Lys Asp Asn
        115                 120                 125

Gly Val Ser Leu Tyr Ala Ile Ser Val Gln Asn Glu Pro Asp Tyr Ala
    130                 135                 140

His Asp Trp Thr Trp Trp Thr Pro Thr Glu Met Ile Arg Phe Leu Arg
145                 150                 155                 160

Glu Asn Ala Gly Ser Ile Glu Ile Lys Val Ile Ala Pro Glu Ser Phe
                165                 170                 175

Gln Tyr Val Lys Ser Phe Ser Asp Pro Ile Leu Asn Asp Pro Thr Ala
            180                 185                 190

Leu Ala Asn Leu Asp Ile Leu Gly Ala His Leu Tyr Gly Thr Pro Tyr
        195                 200                 205

Gln Asn Phe Pro Tyr Pro Leu Phe Lys Glu Lys Gly Arg Gly Lys Glu
    210                 215                 220

Leu Trp Met Thr Glu Val Tyr Tyr Pro Asn Ser Ser Asp Ser Ala Asp
225                 230                 235                 240

Leu Trp Pro Gln Ala Leu Asp Val Ala Glu His Ile His His Ala Leu
                245                 250                 255

Val Asp Ala Glu Phe Gln Ala Tyr Val Trp Trp Tyr Ile Arg Arg Ser
            260                 265                 270

Tyr Gly Pro Met Arg Glu Asp Gly Arg Ile Ser Lys Arg Gly Ala Thr
        275                 280                 285

Met Ala His Phe Ser Lys Phe Val Arg Pro Gly Tyr Val Arg Ile Asp
    290                 295                 300

Ala Thr Ser Asn Pro Gln Ser Asn Leu Tyr Val Leu Ala Tyr Lys Gly
305                 310                 315                 320
```

```
Gly Asp Ser Lys Val Val Ile Ala Ile Asn Lys Gly Thr Ser Ser
            325                 330                 335

Val Ser Gln Pro Phe Thr Leu Val Asn Asn Thr Ser Ser Val Ser
        340                 345                 350

Ser Trp Leu Thr Asp Ala Ser Arg Asn Leu Ala Ser Leu Gly Ala Met
        355                 360                 365

Ser Val Ser Asn Gly Ser Phe Thr Gly Gln Leu Pro Ala Arg Ser Val
    370                 375                 380

Thr Thr Phe Val Thr
385

<210> SEQ ID NO 15
<211> LENGTH: 389
<212> TYPE: PRT
<213> ORGANISM: Clostridium saccharoperbutylacetonicum

<400> SEQUENCE: 15

Ala Glu Ser Asn Thr Thr Ile Asn Leu Ser Gly Glu Lys Gln Val Ile
1               5                   10                  15

Arg Gly Phe Gly Gly Ile Asn His Pro Ala Trp Ala Gly Asp Leu Thr
            20                  25                  30

Ala Ala Gln Arg Glu Thr Ala Phe Gly Asn Gly Asp Asn Gln Leu Gly
        35                  40                  45

Phe Ser Ile Leu Arg Ile Tyr Val Asp Asp Asn Lys Asn Asn Trp Tyr
    50                  55                  60

Lys Glu Leu Glu Thr Ala Lys Lys Ala Ile Glu His Gly Ala Ile Val
65                  70                  75                  80

Phe Ala Ser Pro Trp Asn Pro Pro Ser Glu Met Thr Glu Thr Phe Asn
                85                  90                  95

Arg Asn Gly Asp Thr Lys Ala Lys Arg Leu Arg Tyr Asp Lys Tyr Ala
            100                 105                 110

Glu Tyr Ala Gln His Leu Asn Asp Phe Val Ser Tyr Met Lys Asn Asn
        115                 120                 125

Gly Val Ser Leu Tyr Ala Ile Ser Val Gln Asn Glu Pro Asp Tyr Gly
    130                 135                 140

Lys Asp Trp Thr Trp Trp Thr Pro Glu Glu Ile Leu Arg Phe Met Lys
145                 150                 155                 160

Glu Asn Ala Gly Ser Ile Asn Cys Lys Val Met Ser Pro Glu Ser Phe
                165                 170                 175

Ser Tyr Gln Lys Lys Met Tyr Asp Pro Ile Leu Asn Asp Ser Lys Ala
            180                 185                 190

Leu Ala Asn Met Asp Val Leu Gly Thr His Thr Tyr Gly Thr Gln Val
        195                 200                 205

Lys Asp Phe Pro Tyr Pro Leu Phe Lys Gln Lys Gly Ala Gly Lys Glu
    210                 215                 220

Leu Trp Met Thr Glu Val Tyr Val Pro Asn Ser Asp Asn Asn Ser Ala
225                 230                 235                 240

Asp Arg Trp Pro Glu Ala Leu Asp Val Ala Tyr His Val His Asn Ala
                245                 250                 255

Met Val Glu Gly Asp Phe Gln Ala Tyr Thr Trp Trp Tyr Ile Arg Arg
            260                 265                 270

Gln Tyr Gly Pro Met Lys Glu Asp Gly Asn Ile Ser Lys Arg Gly Tyr
        275                 280                 285

Met Met Ala Gln Phe Ser Lys Phe Val Arg Pro Gly Tyr Val Arg Val
    290                 295                 300
```

```
Asp Ala Thr Lys Asn Pro Ile Ser Asn Ile Tyr Val Ser Ala Tyr Lys
305                 310                 315                 320

Gly Asp Asn Lys Val Val Ile Val Ala Ile Asn Lys Gly Thr Ser Gln
                325                 330                 335

Val Ser Gln Ser Phe Asn Ile Gln Asn Gly Ser Ala Ser Lys Val Ser
            340                 345                 350

Ser Trp Val Thr Thr Gly Ser Gln Asn Ile Ala Lys Ser Ala Asp Ile
        355                 360                 365

Asn Val Val Asn Gly Asn Phe Thr Ala Ser Leu Pro Ala Gln Ser Val
    370                 375                 380

Thr Thr Phe Val Gly
385

<210> SEQ ID NO 16
<211> LENGTH: 389
<212> TYPE: PRT
<213> ORGANISM: Geobacillus sp.

<400> SEQUENCE: 16

Ala Ala Ser Asp Ala Val Val Asn Val Ser Ser Glu Lys Gln Val Ile
1               5                   10                  15

Arg Gly Phe Gly Gly Ile Asn His Pro Ala Trp Ile Gly Asp Leu Thr
            20                  25                  30

Ala Ala Gln Arg Glu Thr Ala Phe Gly Asn Gly Asn Asn Gln Leu Gly
        35                  40                  45

Phe Ser Ile Leu Arg Ile Tyr Val His Glu Asp Arg Asn Gln Trp Tyr
50                  55                  60

Arg Glu Leu Asp Thr Ala Lys Arg Ala Ile Ala Leu Gly Ala Ile Val
65                  70                  75                  80

Phe Ala Ser Pro Trp Asn Pro Pro Ala Asp Met Val Glu Thr Phe Asn
                85                  90                  95

Arg Asn Gly Asp Thr Ser Ala Lys Arg Leu Arg Tyr Asp Lys Tyr Ala
            100                 105                 110

Ala Tyr Ala Gln His Leu Asn Asp Phe Val Thr Tyr Met Arg Asn Asn
        115                 120                 125

Gly Val Asn Leu Tyr Ala Ile Ser Val Gln Asn Glu Pro Asp Tyr Ala
130                 135                 140

His Asp Trp Thr Trp Trp Thr Pro Gln Glu Met Leu Arg Phe Met Lys
145                 150                 155                 160

Glu Asn Ala Gly Ser Ile Asn Ser Arg Val Ile Ala Pro Glu Ser Phe
                165                 170                 175

Gln Tyr Leu Lys Asn Met Ser Asp Pro Ile Leu Asn Asp Pro Gln Ala
            180                 185                 190

Leu Ala Asn Met Asp Ile Leu Gly Ala His Leu Tyr Gly Thr Gln Val
        195                 200                 205

Ser Asn Phe Ala Tyr Pro Leu Phe Lys Gln Lys Gly Ala Gly Lys Asp
        210                 215                 220

Leu Trp Met Thr Glu Val Tyr Tyr Pro Asn Ser Asp Asn Ser Ala
225                 230                 235                 240

Asp Arg Trp Pro Glu Ala Leu Asp Val Ser Tyr His Ile His Asn Ala
                245                 250                 255

Met Val Glu Gly Asp Phe Gln Ala Tyr Val Trp Trp Tyr Ile Arg Arg
            260                 265                 270

Ser Tyr Gly Pro Met Lys Glu Asp Gly Thr Ile Ser Asn Arg Gly Tyr
```

```
                275                 280                 285
Asn Met Ala His Phe Ser Arg Phe Val Arg Pro Gly Tyr Val Arg Val
    290                 295                 300
Asp Ala Ser Lys Asn Pro Glu Thr Asn Val Tyr Val Ser Ala Tyr Lys
305                 310                 315                 320
Gly Asp Asn Lys Ile Val Ile Val Ala Ile Asn Arg Asn Asn Ser Gly
                325                 330                 335
Val Asn Gln Asn Phe Val Leu Gln Asn Gly Ser Val Ser Gln Val Ser
            340                 345                 350
Arg Trp Ile Thr Ser Ser Ser Asn Leu Gln Pro Gly Thr Ser Leu
                355                 360                 365
Asn Val Thr Gly Ser Asn Phe Trp Ala His Leu Pro Ala Gln Ser Val
        370                 375                 380
Thr Thr Phe Val Gly
385

<210> SEQ ID NO 17
<211> LENGTH: 388
<212> TYPE: PRT
<213> ORGANISM: Clostridium papyrosolvens

<400> SEQUENCE: 17

Ala Ala Ser Asp Val Thr Val Asn Leu Ser Ser Glu Lys Gln Val Ile
1               5                   10                  15
Arg Gly Phe Gly Gly Met Asn Tyr Pro Ala Trp Gln Gly Ser Asp Leu
            20                  25                  30
Thr Ala Asp Gln Arg Gln Thr Ala Phe Gly Asn Gly Asn Gly Gln Leu
        35                  40                  45
Gly Phe Ser Ile Leu Arg Ile His Val Asp Pro Asp Lys Thr Thr Trp
    50                  55                  60
Ser Lys Glu Val Asp Thr Ala Lys Ala Ala Ile Lys Asn Gly Ala Ile
65                  70                  75                  80
Val Phe Ala Ser Pro Trp Asn Pro Pro Ser Asp Met Val Gln Thr Val
                85                  90                  95
Asn Gly Gln Lys His Val Ile Pro Ala Lys Tyr Gly Ala Tyr Ala Gln
            100                 105                 110
His Leu Asn Asp Phe Val Ala Tyr Met Lys Glu Asn Gly Val Asp Leu
        115                 120                 125
Tyr Ala Ile Ser Ile Gln Asn Glu Pro Asp Tyr Ala Asn Glu Trp Thr
    130                 135                 140
Trp Trp Thr Pro Gln Glu Met Leu Thr Phe Met Lys Asp Tyr Ala Gly
145                 150                 155                 160
Thr Ile Asn Cys Arg Val Ile Ala Pro Glu Ser Phe Gln Tyr Ile Lys
                165                 170                 175
Ser Met Ser Asp Pro Ile Leu Asn Asp Pro Gln Ala Leu Ala Asn Met
            180                 185                 190
Asp Ile Leu Gly Ala His Leu Tyr Gly Thr Gln Val Ser Asn Phe Pro
        195                 200                 205
Tyr Pro Leu Phe Lys Gln Lys Gly Ala Gly Lys Asp Leu Trp Met Thr
    210                 215                 220
Glu Val Tyr Tyr Pro Asn Ser Glu Ala Asn Ser Ala Asp Arg Trp Pro
225                 230                 235                 240
Glu Ala Leu Glu Val Ala Asn His Met His Asn Ala Met Val Glu Ala
                245                 250                 255
```

```
Glu Phe Gln Thr Tyr Val Trp Trp Phe Ile Arg Arg Gln Tyr Gly Pro
            260                 265                 270

Met Lys Glu Asp Gly Thr Met Ser Lys Arg Gly Ala Met Met Ser Gln
    275                 280                 285

Phe Ser Lys Phe Val Arg Pro Gly Tyr Thr Arg Val Asp Ala Thr Lys
    290                 295                 300

Asn Pro Asp Thr Asn Val Phe Val Ser Ser Tyr Lys Gly Asp Asn Lys
305                 310                 315                 320

Val Val Ile Val Ala Ile Asn Lys Gly Thr Ser Ala Ile Ser Gln Lys
                325                 330                 335

Phe Ile Met Gln Asn Gly Ala Ser Ala Ser Ala Thr Lys Val Ala Thr
            340                 345                 350

Trp Ile Thr Asp Ser Ser Lys Asn Val Ala Ala Gly Ser Asp Ile Asn
            355                 360                 365

Val Ser Ala Gly Thr Phe Thr Ala Gln Leu Pro Ala Gln Ser Val Thr
    370                 375                 380

Thr Phe Val Ala
385

<210> SEQ ID NO 18
<211> LENGTH: 390
<212> TYPE: PRT
<213> ORGANISM: Micromonospora lupini str.

<400> SEQUENCE: 18

Ser Ala Ala Ala Ala Ser Ile Asn Leu Ser Ala Gln Arg Gln Thr Ile
1               5                   10                  15

Arg Gly Phe Gly Ala Met Ala His Ala Ala Trp Ile Gly Asp Leu Thr
            20                  25                  30

Ala Ala Gln Arg Glu Thr Ala Phe Gly Thr Gly Glu Gly Arg Leu Gly
        35                  40                  45

Phe Ser Leu Leu Arg Ile Pro Val Asn Glu Asn Gln Ala Asp Trp Ser
    50                  55                  60

Ala Asp Leu Ala Thr Ala Gln Arg Ala Ala Glu Leu Gly Val Thr Val
65                  70                  75                  80

Phe Ala Ser Pro Trp Asn Pro Pro Ala Ser Met Ile Glu Thr Phe Thr
                85                  90                  95

Arg Gly Gly Gln Thr Asn Ala Lys Arg Leu Arg Tyr Ser Ser Tyr Gly
            100                 105                 110

Ala Tyr Ala Gln His Leu Asn Ser Phe Thr Thr His Leu Arg Asn Asn
        115                 120                 125

Gly Val Asn Leu Tyr Ala Ile Ser Val Gln Asn Glu Pro Asp Tyr Ala
    130                 135                 140

Thr Glu Trp Thr Trp Trp Thr Ser Thr Glu Met Val Arg Phe Leu Arg
145                 150                 155                 160

Glu Asn Ala Gly Ser Ile Ser Thr Arg Val Ile Ala Pro Glu Ser Phe
                165                 170                 175

Gln Tyr Val Lys Ser Met Ser Asp Pro Ile Leu Asn Asp Ser Thr Ala
            180                 185                 190

Leu Ala Asn Val Asp Ile Ile Gly Ala His Leu Tyr Gly Thr Ser Tyr
        195                 200                 205

Ser Asn Phe Pro Tyr Pro Leu Phe Lys Gln Lys Gly Ala Gly Lys Glu
    210                 215                 220

Leu Trp Met Thr Glu Val Tyr Tyr Pro Asn Ser Asn Thr Asn Ser Gly
225                 230                 235                 240
```

```
Asp Ala Trp Pro Glu Ala Leu Asp Val Gly Glu His Ile His His Ala
                245                 250                 255

Met Val Asp Ala Glu Phe Gln Ala Tyr Val Trp Trp Tyr Leu Arg Arg
            260                 265                 270

Ser Tyr Gly Pro Met Arg Glu Asp Gly Gln Ile Ser Lys Arg Gly Ala
        275                 280                 285

Met Met Ala His Phe Ala Arg Phe Val Arg Pro Gly Tyr Val Arg Val
    290                 295                 300

Asp Ala Thr Ala Asn Pro Ala Ser Asn Val Tyr Val Ser Ala Tyr Arg
305                 310                 315                 320

Gly Gly Asp Thr Val Val Ile Val Ala Val Asn Lys Asn Thr Ser Ser
                325                 330                 335

Val Ser Gln Gln Phe Thr Leu Ser Asn Thr Ser Ala Ser Gly Ser Val
            340                 345                 350

Ser Asn Trp Leu Thr Asp Gly Ser Arg Asn Val Ala Pro Gln Gly Ala
        355                 360                 365

Leu Thr Met Ser Asn Gly Ser Leu Thr Val Thr Leu Pro Ala Arg Ser
    370                 375                 380

Val Met Thr Phe Val Ala
385                 390

<210> SEQ ID NO 19
<211> LENGTH: 388
<212> TYPE: PRT
<213> ORGANISM: Bacillus xiamenensis

<400> SEQUENCE: 19

Ala Ala Ser Asp Ala Asn Ile Asn Ile Asn Ala Glu Arg Gln Leu Ile
1               5                   10                  15

Arg Gly Phe Gly Gly Met Asn His Pro Ala Trp Ile Gly Asp Leu Thr
            20                  25                  30

Ala Pro Gln Arg Glu Thr Ala Phe Gly Asn Gly Gln Asn Gln Leu Gly
        35                  40                  45

Phe Ser Ile Leu Arg Ile Tyr Val Asp Glu Asn Arg Asn Asn Trp Ser
    50                  55                  60

Arg Glu Val Ala Thr Ala Lys Arg Ala Ile Glu His Gly Ala Leu Val
65                  70                  75                  80

Ile Ala Ser Pro Trp Asn Pro Pro Ser Ser Met Val Glu Thr Phe Ile
                85                  90                  95

Arg Asn Gly Ser Pro Ala Lys Arg Leu Lys Tyr Asp Gln Tyr Ala Ala
            100                 105                 110

Tyr Ala Gln His Leu Asn Asp Phe Val Thr Tyr Met Lys Asn Asn Gly
        115                 120                 125

Val Asn Leu Tyr Gly Ile Ser Val Gln Asn Glu Pro Asp Tyr Ala His
    130                 135                 140

Asp Trp Thr Trp Trp Thr Pro Gln Glu Ile Leu Arg Phe Met Arg Glu
145                 150                 155                 160

Asn Ala Gly Ser Ile Asn Ala Arg Val Ile Ala Pro Glu Ser Phe Gln
                165                 170                 175

Tyr Leu Lys Asn Ile Ser Asp Pro Ile Leu Asn Asp Pro Gln Ala Leu
            180                 185                 190

Arg Asn Met Asp Ile Leu Gly Ala His Leu Tyr Gly Thr Gln Ile Ser
        195                 200                 205

Gln Leu Pro Tyr Pro Leu Phe Lys Gln Lys Gly Ala Gly Lys Glu Leu
```

```
                    210                 215                 220
Trp Met Thr Glu Val Tyr Tyr Pro Asn Ser Asn Ser Asn Ser Ala Asp
225                 230                 235                 240

Arg Trp Pro Glu Ala Leu Gly Val Ser Glu His Ile His His Ser Met
                245                 250                 255

Val Glu Gly Asp Phe Gln Ala Tyr Val Trp Trp Tyr Ile Arg Arg Ser
                260                 265                 270

Tyr Gly Pro Met Lys Glu Asp Gly Met Ile Ser Lys Arg Gly Tyr Asn
                275                 280                 285

Met Ala His Phe Ser Lys Phe Val Arg Pro Gly Tyr Val Arg Ile Asp
                290                 295                 300

Ala Thr Lys Ser Pro Glu Ser Asn Val Phe Val Ser Ala Tyr Lys Gly
305                 310                 315                 320

Asn Asn Gln Val Val Ile Val Ala Ile Asn Lys Asn Asn Ala Gly Val
                325                 330                 335

Asn Gln His Phe Val Val Gln Asn Gly Ser Val Ser Gln Ala Ser Arg
                340                 345                 350

Trp Val Thr Ser Ala Ser Ser Asn Leu Gln Pro Gly Thr Asp Ile Thr
                355                 360                 365

Ile Ser Gly Asn Gln Phe Trp Ala His Leu Pro Ala Gln Ser Val Thr
                370                 375                 380

Thr Phe Val Ile
385

<210> SEQ ID NO 20
<211> LENGTH: 389
<212> TYPE: PRT
<213> ORGANISM: Bacillus atrophaeus

<400> SEQUENCE: 20

Ala Ala Ser Asp Val Thr Val Asn Leu Ser Ala Glu Lys Gln Val Ile
1               5                   10                  15

Arg Gly Phe Gly Gly Met Asn His Pro Ala Trp Ile Gly Asp Leu Thr
                20                  25                  30

Ala Ala Gln Arg Glu Thr Ala Phe Gly Asn Gly Gln Asn Gln Leu Gly
                35                  40                  45

Phe Ser Ile Leu Arg Ile His Ile Asp Glu Asn Arg Asn Asn Trp Tyr
                50                  55                  60

Arg Glu Val Glu Thr Ala Lys Ser Ala Ile Lys His Gly Ala Ile Val
65                  70                  75                  80

Phe Ala Ser Pro Trp Asn Pro Pro Ser Asn Met Val Glu Thr Phe Asn
                85                  90                  95

His Asn Gly Asp Ala Ser Ala Lys Arg Leu Arg Tyr Ala Lys Tyr Ala
                100                 105                 110

Ala Tyr Ala Gln His Leu Asn Asp Phe Val Thr Tyr Met Lys Asn Asn
                115                 120                 125

Gly Val Asn Leu Tyr Ala Ile Ser Val Gln Asn Glu Pro Asp Tyr Ala
                130                 135                 140

His Glu Trp Thr Trp Trp Thr Pro Gln Glu Ile Leu Arg Phe Met Arg
145                 150                 155                 160

Glu Asn Ala Gly Ser Ile Asn Ala Arg Val Ile Ala Pro Glu Ser Phe
                165                 170                 175

Gln Tyr Leu Lys Asn Ile Ser Asp Pro Ile Leu Asn Asp Pro Gln Ala
                180                 185                 190
```

-continued

```
Leu Arg Asn Met Asp Ile Leu Gly Thr His Leu Tyr Gly Thr Gln Val
            195                 200                 205

Ser Gln Phe Pro Tyr Pro Leu Phe Lys Gln Lys Gly Ala Gly Lys Glu
    210                 215                 220

Leu Trp Met Thr Glu Val Tyr Tyr Pro Asn Ser Asp Asn Asn Ser Ala
225                 230                 235                 240

Asp Arg Trp Pro Glu Ala Leu Gly Val Ser Glu His Ile His His Ser
                245                 250                 255

Met Val Glu Gly Asp Phe Gln Thr Tyr Val Trp Tyr Ile Arg Arg
            260                 265                 270

Ser Tyr Gly Pro Met Lys Glu Asp Gly Lys Ile Ser Lys Arg Gly Tyr
    275                 280                 285

Asn Met Ala His Phe Ser Lys Phe Val Arg Pro Gly Tyr Ile Arg Val
            290                 295                 300

Asp Ala Thr Lys Asn Pro Asn Ala Asn Val Tyr Val Ser Ala Tyr Lys
305                 310                 315                 320

Gly Asp Asn Lys Val Val Ile Val Ala Ile Asn Lys Ser Asn Thr Gly
                325                 330                 335

Val Asn Gln Asn Phe Val Leu Gln Asn Gly Ser Ala Ser Gln Val Ser
            340                 345                 350

Arg Trp Ile Thr Ser Gly Ser Ser Asn Leu Gln Pro Gly Thr Asn Leu
        355                 360                 365

Asn Val Thr Asp Asn His Phe Trp Ala His Leu Pro Ala Gln Ser Val
    370                 375                 380

Thr Thr Phe Val Val
385

<210> SEQ ID NO 21
<211> LENGTH: 387
<212> TYPE: PRT
<213> ORGANISM: Bacillus stratosphericus

<400> SEQUENCE: 21

Ala Ala Asp Ala Asn Ile Asn Leu Asn Ala Glu Arg Gln Val Ile Arg
1               5                   10                  15

Gly Phe Gly Gly Met Asn His Pro Ala Trp Ile Gly Asp Leu Thr Ala
            20                  25                  30

Pro Gln Arg Glu Thr Ala Phe Gly Asn Gly Gln Asn Gln Leu Gly Phe
        35                  40                  45

Ser Ile Leu Arg Ile Tyr Val Asp Glu Asn Arg Asn Asn Trp Ser Arg
    50                  55                  60

Glu Val Ala Thr Ala Lys Arg Ala Ile Glu His Gly Ala Leu Val Ile
65                  70                  75                  80

Ala Ser Pro Trp Asn Pro Pro Ser Ser Met Val Glu Thr Phe Asn Arg
                85                  90                  95

Asn Gly Ser Pro Ala Lys Arg Leu Lys Tyr Asn Gln Tyr Ala Ala Tyr
            100                 105                 110

Ala Gln His Leu Asn Asp Phe Val Thr Tyr Met Lys Asn Asn Gly Val
        115                 120                 125

Asn Leu Tyr Ala Ile Ser Val Gln Asn Glu Pro Asp Tyr Ala His Glu
    130                 135                 140

Trp Thr Trp Trp Thr Pro Gln Glu Ile Leu Arg Phe Met Arg Glu Asn
145                 150                 155                 160

Ala Gly Ser Ile Asn Ala Arg Val Ile Ala Pro Glu Ser Phe Gln Tyr
                165                 170                 175
```

Leu Lys Asn Ile Ser Asp Pro Ile Leu Asn Asp Pro Gln Ala Leu Arg
            180                 185                 190

Asn Met Asp Ile Leu Gly Ala His Leu Tyr Gly Thr Gln Ile Ser Gln
            195                 200                 205

Leu Pro Tyr Pro Leu Phe Lys Gln Lys Gly Ala Gly Lys Glu Leu Trp
            210                 215                 220

Met Thr Glu Val Tyr Tyr Pro Asn Ser Asp Asn Ser Ala Asp Arg
225                 230                 235                 240

Trp Pro Glu Ala Leu Gly Val Ser Glu His Ile His His Ser Met Val
            245                 250                 255

Glu Gly Asp Phe Gln Ala Tyr Val Trp Trp Tyr Ile Arg Arg Ser Tyr
            260                 265                 270

Gly Pro Met Lys Glu Asp Gly Met Ile Ser Lys Arg Gly Tyr Asn Met
            275                 280                 285

Ala His Phe Ser Lys Phe Val Arg Pro Gly Tyr Val Arg Ile Asp Ala
            290                 295                 300

Thr Lys Ser Pro Glu Pro Asn Val Phe Val Ser Ala Tyr Lys Gly Asn
305                 310                 315                 320

Asn Gln Val Val Ile Val Ala Ile Asn Lys Asn Asn Ala Gly Val Asn
            325                 330                 335

Gln His Phe Val Val Gln Asn Gly Ser Val Ser Gln Ala Ser Arg Trp
            340                 345                 350

Val Thr Ser Gly Ser Ser Asn Leu Gln Pro Gly Thr Asp Leu Asn Ile
            355                 360                 365

Ser Gly Asn Gln Phe Trp Ala His Leu Pro Ala Gln Ser Val Thr Thr
            370                 375                 380

Phe Val Val
385

<210> SEQ ID NO 22
<211> LENGTH: 388
<212> TYPE: PRT
<213> ORGANISM: Bacillus pumilus

<400> SEQUENCE: 22

Ala Ala Ser Asp Ala Asn Ile Asn Val Asn Ala Glu Arg Gln Met Ile
1               5                   10                  15

Arg Gly Phe Gly Gly Met Asn His Pro Ala Trp Ile Gly Asp Leu Thr
            20                  25                  30

Gly Pro Gln Arg Glu Thr Ala Phe Gly Asn Gly Gln Asn Gln Leu Gly
            35                  40                  45

Phe Ser Ile Leu Arg Ile Tyr Val Asp Glu Asn Arg Asn Asn Trp His
            50                  55                  60

Arg Glu Val Ala Thr Ala Lys Arg Ala Ile Glu His Gly Ala Leu Val
65              70                  75                  80

Ile Ala Ser Pro Trp Asn Pro Ser His Met Val Glu Thr Phe Asn
            85                  90                  95

Arg Asn Gly Ala Ser Ala Lys Arg Leu Arg Tyr Asn Gln Tyr Ala Ala
            100                 105                 110

Tyr Ala Gln His Leu Asn Asp Phe Val Thr Tyr Met Lys Asn Asn Gly
            115                 120                 125

Val Asn Leu Tyr Ala Ile Ser Val Gln Asn Glu Pro Asp Tyr Ala His
            130                 135                 140

Glu Trp Thr Trp Trp Thr Pro Gln Glu Ile Leu Arg Phe Met Arg Glu

```
                145                 150                 155                 160
Asn Ala Gly Ser Ile Asn Ala Arg Val Ile Ala Pro Glu Ser Phe Gln
                165                 170                 175

Tyr Leu Lys Asn Ile Ser Asp Pro Ile Leu Asn Asp Ser Gln Ala Leu
                180                 185                 190

Arg Asn Met Asp Ile Leu Gly Ala His Leu Tyr Gly Thr Gln Ile Ser
                195                 200                 205

Gln Leu Pro Tyr Pro Leu Phe Lys Gln Lys Gly Gly Lys Glu Leu
210                 215                 220

Trp Met Thr Glu Val Tyr Tyr Pro Asn Ser Asp Asn Ser Ala Asp
225                 230                 235                 240

Arg Trp Pro Glu Ala Leu Gly Val Ser Glu His Ile His Ser Met
                245                 250                 255

Val Glu Gly Asp Phe Gln Ala Tyr Val Trp Trp Tyr Ile Arg Arg Ser
                260                 265                 270

Tyr Gly Pro Met Lys Glu Asp Gly Met Ile Ser Lys Arg Gly Tyr Asn
                275                 280                 285

Met Ala His Phe Ser Lys Phe Val Arg Pro Gly Phe Val Arg Val Asp
                290                 295                 300

Ala Thr Lys Ser Pro Glu Pro Asn Val Phe Val Ser Ala Tyr Lys Gly
305                 310                 315                 320

Asn Asn Gln Val Val Ile Val Ala Ile Asn Lys Asn Asn Ala Gly Val
                325                 330                 335

Asn Gln His Phe Val Met Gln Asn Gly Thr Ala Ser Lys Ala Ser Arg
                340                 345                 350

Trp Val Thr Ser Ser Asn Ser Asn Leu Gln Pro Gly Thr Asp Leu Asn
                355                 360                 365

Ile Ser Gly Asn Gln Phe Trp Ala His Leu Pro Ala Gln Ser Val Thr
                370                 375                 380

Thr Phe Val Val
385

<210> SEQ ID NO 23
<211> LENGTH: 388
<212> TYPE: PRT
<213> ORGANISM: Bacillus pumilus

<400> SEQUENCE: 23

Ala Ala Ser Asp Ala Asn Ile Asn Val Asn Ala Glu Arg Gln Val Ile
1               5                   10                  15

Arg Gly Phe Gly Gly Met Asn His Pro Ala Trp Ile Gly Asp Leu Thr
                20                  25                  30

Gly Pro Gln Arg Asp Thr Ala Phe Gly Asn Gly Gln Asn Gln Leu Gly
                35                  40                  45

Phe Ser Ile Leu Arg Ile Tyr Val Asp Glu Asn Arg Asn Asn Trp His
                50                  55                  60

Arg Glu Val Ala Thr Ala Lys Arg Ala Ile Glu His Gly Ala Leu Val
65                  70                  75                  80

Ile Ala Ser Pro Trp Asn Pro Pro Ser His Met Val Glu Thr Phe Asn
                85                  90                  95

Arg Asn Gly Ala Ser Ala Lys Arg Leu Arg Tyr Asn Gln Tyr Ala Ala
                100                 105                 110

Tyr Ala Gln His Leu Asn Asp Phe Val Thr Tyr Met Lys Asn Asn Gly
                115                 120                 125
```

Val Asn Leu Tyr Ala Ile Ser Val Gln Asn Glu Pro Asp Tyr Ala His
130                 135                 140

Glu Trp Thr Trp Thr Pro Gln Glu Ile Leu Arg Phe Met Arg Glu
145                 150                 155                 160

Asn Ala Gly Ser Ile Asn Ala Arg Val Ile Ala Pro Glu Ser Phe Gln
            165                 170                 175

Tyr Leu Lys Asn Ile Ser Asp Pro Ile Leu Asn Asp Pro Gln Ala Leu
            180                 185                 190

Arg Asn Met Asp Ile Leu Gly Ala His Leu Tyr Gly Thr Gln Ile Ser
            195                 200                 205

Gln Leu Pro Tyr Pro Leu Phe Lys Gln Lys Gly Gly Lys Glu Leu
210                 215                 220

Trp Met Thr Glu Val Tyr Pro Asn Ser Asp Asn Ser Ala Asp
225                 230                 235                 240

Arg Trp Pro Glu Ala Leu Gly Val Ser Glu His Ile His Ser Met
            245                 250                 255

Val Glu Gly Asp Phe Gln Ala Tyr Val Trp Trp Tyr Ile Arg Arg Ser
            260                 265                 270

Tyr Gly Pro Met Lys Glu Asp Gly Met Ile Ser Lys Arg Gly Tyr Asn
            275                 280                 285

Met Ala His Phe Ser Lys Phe Val Arg Pro Gly Tyr Val Arg Ile Asp
290                 295                 300

Ala Thr Lys Ser Pro Glu Pro Asn Val Phe Val Ser Ala Tyr Lys Gly
305                 310                 315                 320

Asn Asn Gln Val Val Ile Val Ala Ile Asn Lys Asn Asn Thr Gly Val
                325                 330                 335

Asn Gln His Phe Val Met Gln Asn Gly Thr Ala Ser Gln Ala Ser Arg
            340                 345                 350

Trp Ile Thr Ser Ser Asn Ser Asn Leu Gln Pro Gly Thr Asp Leu Asn
            355                 360                 365

Ile Ser Gly Asn Gln Phe Trp Ala His Leu Pro Ala Gln Ser Val Thr
            370                 375                 380

Thr Phe Val Val
385

<210> SEQ ID NO 24
<211> LENGTH: 389
<212> TYPE: PRT
<213> ORGANISM: Bacillus licheniformis

<400> SEQUENCE: 24

Ala Ala Ser Asp Ala Thr Val Arg Leu Ser Ala Glu Lys Gln Val Ile
1               5                   10                  15

Arg Gly Phe Gly Gly Met Asn His Pro Ala Trp Ile Gly Asp Leu Thr
                20                  25                  30

Ala Ala Gln Arg Glu Thr Ala Phe Gly Asn Gly Gln Asn Gln Leu Gly
            35                  40                  45

Phe Ser Ile Leu Arg Ile His Val Asp Glu Asn Arg Asn Asn Trp Tyr
50                  55                  60

Arg Glu Val Glu Thr Ala Lys Ser Ala Ile Lys His Gly Ala Ile Val
65                  70                  75                  80

Phe Ala Ser Pro Trp Asn Pro Pro Ser Asp Met Val Glu Thr Phe Asn
                85                  90                  95

Arg Asn Gly Asp Thr Ser Ala Lys Arg Leu Arg Tyr Asp Lys Tyr Ala
            100                 105                 110

```
Ala Tyr Ala Lys His Leu Asn Asp Phe Val Thr Phe Met Lys Asn Asn
            115                 120                 125

Gly Val Asn Leu Tyr Ala Ile Ser Val Gln Asn Glu Pro Asp Tyr Ala
        130                 135                 140

His Asp Trp Thr Trp Trp Thr Pro Gln Glu Ile Leu Arg Phe Met Lys
145                 150                 155                 160

Glu Asn Ala Gly Ser Ile Asn Ala Arg Val Ile Ala Pro Glu Ser Phe
                165                 170                 175

Gln Tyr Leu Lys Asn Ile Ser Asp Pro Ile Leu Asn Asp Pro Lys Ala
            180                 185                 190

Leu Ala Asn Met Asp Ile Leu Gly Ala His Leu Tyr Gly Thr Gln Leu
        195                 200                 205

Asn Asn Phe Ala Tyr Pro Leu Phe Lys Gln Lys Gly Ala Gly Lys Asp
    210                 215                 220

Leu Trp Met Thr Glu Val Tyr Tyr Pro Asn Ser Asp Asn His Ser Ala
225                 230                 235                 240

Asp Arg Trp Pro Glu Ala Leu Asp Val Ser His Ile His Asn Ser
                245                 250                 255

Met Val Glu Gly Asp Phe Gln Ala Tyr Val Trp Trp Tyr Ile Arg Arg
                260                 265                 270

Ser Tyr Gly Pro Met Lys Glu Asp Gly Thr Ile Ser Lys Arg Gly Tyr
            275                 280                 285

Asn Met Ala His Phe Ser Lys Phe Val Arg Pro Gly Tyr Val Arg Val
        290                 295                 300

Asp Ala Thr Lys Ser Pro Ala Ser Asn Val Tyr Val Ser Ala Tyr Lys
305                 310                 315                 320

Gly Asp Asn Lys Val Val Ile Val Ala Ile Asn Lys Asn Asn Ser Gly
                325                 330                 335

Val Asn Gln Asn Phe Val Leu Gln Asn Gly Ser Val Ser Gln Val Ser
            340                 345                 350

Arg Trp Ile Thr Ser Ser Ser Asn Leu Gln Pro Gly Thr Asn Leu
        355                 360                 365

Asn Val Thr Asp Asn His Phe Trp Ala His Leu Pro Ala Gln Ser Val
    370                 375                 380

Thr Thr Phe Val Ala
385

<210> SEQ ID NO 25
<211> LENGTH: 389
<212> TYPE: PRT
<213> ORGANISM: Bacillus amyloliquefaciens

<400> SEQUENCE: 25

Ala Ala Ser Asp Ala Thr Val Asn Ile Ser Ala Glu Arg Gln Val Ile
1               5                   10                  15

Arg Gly Phe Gly Gly Met Asn His Pro Ala Trp Ile Gly Asp Leu Thr
                20                  25                  30

Ala Pro Gln Arg Glu Thr Ala Phe Gly Asn Gly Gln Asn Gln Leu Gly
            35                  40                  45

Phe Ser Val Leu Arg Ile His Val Asp Glu Asn Arg Asn Asn Trp Tyr
        50                  55                  60

Lys Glu Val Glu Thr Ala Lys Ser Ala Ile Lys His Gly Ala Ile Val
65                  70                  75                  80

Phe Ala Ser Pro Trp Asn Pro Pro Asn Asp Met Val Glu Thr Phe Asn
```

```
                        85                  90                  95
His Asn Gly Asp Thr Ser Ala Lys Arg Leu Lys Tyr Asp Lys Tyr Ala
                    100                 105                 110

Ala Tyr Ala Gln His Leu Asn Asp Phe Val Asn Phe Met Lys Ser Asn
                115                 120                 125

Gly Val Asn Leu Tyr Ala Ile Ser Met Gln Asn Glu Pro Asp Tyr Ala
            130                 135                 140

His Glu Trp Thr Trp Trp Thr Pro Gln Glu Ile Leu Arg Phe Met Arg
145                 150                 155                 160

Glu Asn Ala Gly Ser Ile Asn Ala Arg Val Ile Ala Pro Glu Ser Phe
                165                 170                 175

Gln Tyr Leu Lys Asn Ile Ser Asp Pro Ile Leu Asn Asp Pro Gln Ala
                180                 185                 190

Leu Arg Asn Met Asp Ile Leu Gly Thr His Leu Tyr Gly Thr Gln Val
                195                 200                 205

Ser Gln Phe Pro Tyr Pro Leu Phe Lys Gln Lys Gly Gly Lys Glu
            210                 215                 220

Leu Trp Met Thr Glu Val Tyr Tyr Pro Asn Ser Asp Asn Ser Ala
225                 230                 235                 240

Asp Arg Trp Pro Glu Ala Leu Gly Val Ser Glu His Ile His His Ser
                245                 250                 255

Met Val Glu Gly Asp Phe Gln Ala Tyr Val Trp Trp Tyr Ile Arg Arg
                260                 265                 270

Ser Tyr Gly Pro Met Lys Glu Asp Gly Met Ile Ser Lys Arg Gly Tyr
            275                 280                 285

Asn Met Ala His Phe Ser Lys Phe Val Arg Pro Gly Tyr Val Arg Ile
            290                 295                 300

Asp Ala Thr Lys Asn Pro Glu Pro Asn Val Tyr Val Ser Ala Tyr Lys
305                 310                 315                 320

Gly Asp Asn Lys Val Val Ile Val Ala Ile Asn Lys Asn Asn Thr Gly
                325                 330                 335

Val Asn Gln Asn Phe Val Leu Gln Asn Gly Thr Ala Ser Gln Val Ser
                340                 345                 350

Arg Trp Ile Thr Ser Ser Ser Ser Asn Leu Gln Pro Gly Thr Asp Leu
                355                 360                 365

Lys Val Thr Asp Asn His Phe Trp Ala His Leu Pro Ala Gln Ser Val
                370                 375                 380

Thr Thr Phe Val Val
385

<210> SEQ ID NO 26
<211> LENGTH: 426
<212> TYPE: PRT
<213> ORGANISM: Fibrobacter succinogenes

<400> SEQUENCE: 26

Phe Ala Ser Thr Val Asn Val Asp Val Thr Glu Glu His Gln Val Ile
1               5                   10                  15

Arg Gly Phe Gly Gly Met Val His Asn Gln Trp Gln Gly Gly Gly Gly
                20                  25                  30

Leu Ser Glu Ala Asp Ala Lys Ile Ala Phe Gly Thr Gly Asp Gly Thr
                35                  40                  45

Ile Gly Leu Asn Thr Leu Arg Ile Pro Val Tyr Ala Asn Ser Asn Asp
            50                  55                  60
```

```
Phe Asn Lys Glu Val Gln Ala Ala Lys Tyr Ala Lys Tyr Ala Gly
 65                  70                  75                  80

Asp Asp Phe Ile Leu Tyr Ala Thr Pro Trp Thr Ser Pro Tyr Ala Gly
             85                  90                  95

Ala Asn Gln His Met Ala Ser Ser Asn Tyr Gln Lys Tyr Val Asp His
                100                 105                 110

Leu Asn Ser Phe Asn Asp Tyr Met Lys Asn Gln Gly Val Pro Leu Tyr
            115                 120                 125

Ala Ile Ser Ile Ser Asn Glu Pro Asp Trp Cys Gly Glu Trp Ala Cys
        130                 135                 140

Trp Ser Ala Asp Glu Ile Tyr Asn Phe Thr Lys Gly Tyr Ala Asp Lys
145                 150                 155                 160

Met Arg Lys Asn Gly Ala Lys Val Ile Ser Thr Glu Ser Phe Arg Tyr
                165                 170                 175

Asp Lys Asn Leu Tyr Asn Lys Val Leu Asn Asp Ala Asn Ala Leu Lys
            180                 185                 190

Asn Trp Asp Ile Leu Gly Ala His Phe Tyr Ala Ser Asp Arg Arg Thr
        195                 200                 205

Gly Asp Asn Phe Phe Gln Tyr Ser Leu Ala Asp Gln Lys Lys Val Glu
210                 215                 220

Arg Trp Met Thr Glu His Tyr Thr Glu Ser Gln Gly Ser Gly Asn Tyr
225                 230                 235                 240

Trp Arg Thr Ile Thr Asn Thr Gly Asp Gln Ala Asn Ala Asn Lys Arg
                245                 250                 255

Asp Thr Val Asn Ala Met Asp Val Ala Tyr Glu Ile His Arg Ala Met
            260                 265                 270

Val Val Gly Asn Phe Asn Gln Tyr Thr Trp Trp Tyr Ile Arg Arg Cys
        275                 280                 285

Tyr Gly Leu Ile Met Glu Lys Asp Phe Gly Asn Lys Leu Gln Ile Pro
290                 295                 300

Gln Asn Glu Ile Gly Lys Ile Ser Lys Arg Gly Tyr Val Met Ser Gln
305                 310                 315                 320

Phe Ala Arg Phe Val Arg Pro Gly Ala Val Arg Val Gly Ala Thr Ala
                325                 330                 335

Asn Pro Glu Lys Glu Val Phe Ala Ser Ala Tyr Lys Ser Lys Asp Gly
            340                 345                 350

Asp Ser Val Ile Val Val Leu Val Asn Arg Asp Tyr Lys Asn Ser Lys
        355                 360                 365

Thr Val Thr Val Asn Val Lys Gly Ala Asp Val Glu Thr Phe His Val
370                 375                 380

Tyr Thr Thr Ser Glu Ala Lys Asn Ala Lys Tyr Glu Gly Glu Val Glu
385                 390                 395                 400

Val Lys Asn Gly Ser Val Thr Ile Thr Met Asp Ala Gly Asn Ser Ser
                405                 410                 415

Asn Lys Asp Cys Ile Val Thr Leu Val Gly
            420                 425

<210> SEQ ID NO 27
<211> LENGTH: 407
<212> TYPE: PRT
<213> ORGANISM: Verrucosispora maris

<400> SEQUENCE: 27

Gly Pro Ala Asp Ile Thr Val Asn Ser Thr Thr Arg Tyr Gln Thr Val
 1               5                  10                  15
```

Asp Gly Phe Gly Ala Ala Thr Pro Ile Trp Gly Gly Thr Trp Ser Thr
           20                  25                  30

Ser Asp Thr Gln Thr Leu Val Gly Leu Gly Ala Asn Gln Leu Gly Leu
       35                  40                  45

Ser Ile Val Arg Thr Gly Ile Ser Pro Val Ser Ser Glu Trp Ser Ser
 50                  55                  60

Gln Val Asn Ala Leu Arg Thr Ala Lys Ser Ala Gly Ser Asn Val Lys
 65                  70                  75                  80

Ile Leu Ala Ser Pro Trp Thr Ala Pro Ala Glu Trp Lys Thr Asn Asn
               85                  90                  95

Ser Arg Ile Asn Gly Gly Lys Leu Arg Thr Asp Arg Tyr Ala Asp Tyr
               100                 105                 110

Ala Asn His Leu Asn Ser Tyr Val Gln Tyr Met Arg Asn Gln Gly Val
           115                 120                 125

Thr Ile Asp Val Thr Ser Val Gln Asn Glu Pro Asp Trp His Pro Asp
130                 135                 140

Tyr Asp Ser Met Asp Trp Ser Gly Thr Glu Leu Arg Asn Phe Val Arg
145                 150                 155                 160

Asp His Gly Thr Arg Val Gln Asn Thr Arg Leu Met Val Ala Glu Ala
               165                 170                 175

Val Asn Leu Asn Tyr Thr Tyr Thr Asp Pro Thr Leu Asn Asp Ala Thr
           180                 185                 190

Ala Arg Asn Asn Ile Gly Tyr Ile Gly Gly His Leu Tyr Gly Thr Glu
       195                 200                 205

Ala Ser Gly Arg Leu Arg Ser Tyr Pro Leu Ala Asp Gln His Asn Lys
   210                 215                 220

Pro Val Trp Met Thr Glu Trp Asn Leu His Ala Ala Asp Gly Asn Gly
225                 230                 235                 240

Ser Asn Ile Trp Gly Asn Pro Ala Asn Leu Ala Val Trp Asn Glu Thr
               245                 250                 255

Leu Asp Asp Ile Met Arg Thr Val His Arg Ser Met Glu Ser Asn Trp
           260                 265                 270

Thr Ala Tyr Ile Trp Trp Tyr Gly Lys Arg Tyr Tyr Ser Phe Ile Gly
       275                 280                 285

Asp Gly Glu Ala Ala Phe Gly Thr Thr Ala Gly Ala Pro Leu Lys Arg
   290                 295                 300

Gly Tyr Ala Phe Ser Gln Tyr Ala Lys Tyr Val Arg Pro Gly Tyr Gln
305                 310                 315                 320

Arg Val Ala Leu Thr Lys Ser Thr Lys Ala Asn Pro Leu Glu Val Thr
               325                 330                 335

Ala Tyr Thr Gly Gly Gly Lys Thr Thr Leu Val Ile Leu Asn Arg Ser
           340                 345                 350

Thr Ser Ala Val Asn Asn Ala Val Ile Gln Val Pro Gln Asn Val Thr
       355                 360                 365

Arg Ala Glu His Tyr Leu Thr Ser Gln Asn Ala Asn Ala Ala Ser Gln
   370                 375                 380

Ser Val Gly Val Asn Gly Gly Gln Val Ser Val Asn Val Gly Ala Arg
385                 390                 395                 400

Ser Ile Ser Thr Val Val Leu
               405

<210> SEQ ID NO 28
<211> LENGTH: 407

```
<212> TYPE: PRT
<213> ORGANISM: Micromonospora sp.

<400> SEQUENCE: 28

Gly Ala Ala Asp Ile Thr Val Asn Thr Ala Ser Arg Tyr Gln Thr Ile
1               5                   10                  15

Asp Gly Phe Gly Ala Ala Val Ser Ile Trp Gly Ala Trp Ser Thr
            20                  25                  30

Ala Glu Thr Gln Thr Leu Val Gly Leu Gly Pro Asn Gln Leu Gly Leu
            35                  40                  45

Ser Ile Val Arg Thr Gly Val Ser Pro Val Ser Gly Glu Trp Gly Thr
50                  55                  60

Gln Val Ser Ala Leu Arg Thr Ala Lys Ser Tyr Gly Ser Asn Val Lys
65                  70                  75                  80

Ile Met Ala Ser Pro Trp Thr Ala Pro Ala Ala Trp Lys Thr Asn Asn
                    85                  90                  95

Ser Arg Ile Asn Gly Gly Lys Leu Arg Thr Asp Tyr Tyr Asp Asp Tyr
            100                 105                 110

Ala Asn His Leu Asn Ser Tyr Val Gln Tyr Met Arg Asn Gln Gly Val
            115                 120                 125

Thr Ile Asp Val Thr Ser Val Gln Asn Glu Pro Asp Trp His Pro Asp
130                 135                 140

Tyr Asp Ser Met Asp Trp Ser Gly Thr Glu Leu Gln Thr Phe Val Arg
145                 150                 155                 160

Glu Gln Gly Ala Lys Val Gln Asn Thr Lys Leu Met Val Ala Glu Ala
                    165                 170                 175

Val Asn Leu Asn Tyr Gly Tyr Thr Asp Pro Thr Leu Asn Asp Ala Ala
            180                 185                 190

Ala Arg Asn Asn Ile Gly Tyr Ile Gly Gly His Leu Tyr Gly Thr Glu
            195                 200                 205

Ala Ser Gly Arg Leu Lys Pro Tyr Thr Leu Ala Gln Gln Tyr Asn Lys
210                 215                 220

Pro Val Trp Met Thr Glu Trp Asn Leu His Glu Ala Asp Gly Gly
225                 230                 235                 240

Ser Asn Ile Trp Gly Asn Pro Ala Asn Ala Ala Trp Asn Glu Thr
            245                 250                 255

Leu Asp Asp Ile Met Arg Thr Val His Lys Ser Met Glu Ser Asn Trp
            260                 265                 270

Ser Ala Tyr Val Trp Trp Tyr Gly Lys Arg Tyr Tyr Ser Phe Ile Gly
            275                 280                 285

Asp Gly Glu Ser Ala Tyr Gly Thr Val Ala Gly Ala Pro Leu Lys Arg
            290                 295                 300

Gly Tyr Ala Phe Ser Gln Tyr Ala Lys Tyr Val Arg Pro Gly Tyr Gln
305                 310                 315                 320

Arg Val Ala Leu Thr Lys Ser Ser Lys Ala Ser Pro Leu Glu Val Thr
                    325                 330                 335

Ala Tyr Ser Gly Asp Gly Lys Val Thr Leu Val Ile Leu Asn Arg Ser
            340                 345                 350

Thr Ser Ala Val Asn Asn Ala Ile Ile Gln Ala Pro Gln Asn Val Ser
            355                 360                 365

Arg Ala Glu Tyr Val Ala Thr Ser Gln Asn Ala Ser Ala Ala Ser Gln
            370                 375                 380

Pro Val Gly Val Asn Gly Asn Gln Val Thr Val Asn Val Gly Ala Arg
385                 390                 395                 400
```

```
Ser Ile Ser Thr Val Val Leu
            405

<210> SEQ ID NO 29
<211> LENGTH: 400
<212> TYPE: PRT
<213> ORGANISM: Bacteroides clarus

<400> SEQUENCE: 29

Ser Ala Ala Pro Leu Ile Ile Asp Thr Asp Thr Glu Tyr Gln Lys Val
1               5                   10                  15

Ile Gly Phe Gly Gly Met Asn Thr Lys Trp Gln Ala Ser Thr Leu Ser
            20                  25                  30

Asp Asn Glu Ile Thr Thr Leu Tyr Gly Asn Gly Glu Gly Gln Leu Gly
        35                  40                  45

Tyr Asn Val Leu Arg Val Arg Ile Ser Pro Asn Gly Glu Arg Asp Trp
    50                  55                  60

Lys Gln Ile Val Gly Thr Val Arg Lys Ala Lys Ser Leu Gly Ala Thr
65                  70                  75                  80

Ile Leu Ala Thr Pro Trp Thr Pro Val Gly Leu Lys Asn Asn His
                85                  90                  95

Ser Ile Val Gln Gly Glu Leu Ala Asp Thr Asp Gly Tyr Ala Ala Tyr
            100                 105                 110

Leu Lys Ser Phe Val Arg Tyr Met Gln Asn Asn Gly Ala Asp Ile Asp
        115                 120                 125

Val Leu Ser Ile Gln Asn Glu Pro Asp Ile Asp Val Lys Tyr Glu Ser
    130                 135                 140

Cys Gln Trp Ser Pro Ala Gln Ile Tyr Asp Phe Val Lys Lys Tyr Gly
145                 150                 155                 160

Ala Glu Leu Arg Ala Thr Gly Val Lys Leu Met Ala Ser Glu His Ser
                165                 170                 175

Lys Phe Asn His Asp Phe Thr Asp Pro Leu Leu Gln Asp Ala Gln Val
            180                 185                 190

Ala Ala Asn Val Asp Cys Ile Gly Gly His Ile Tyr Gly Gly Gly Leu
        195                 200                 205

Val Ser Tyr Asp Leu Val Ala Gln Lys Gly Lys Glu Tyr Trp Met Thr
    210                 215                 220

Glu His Tyr Leu Asn Lys Ala Trp Lys Asp Lys Val Leu Thr Gly Pro
225                 230                 235                 240

Glu Ala Leu Arg Thr Glu Asn Met Ala Phe Ala Glu Glu Leu Asn Asn
                245                 250                 255

Cys Met Asn Leu Gly Phe Asn Val Tyr Ile Trp Trp Tyr Leu Arg Arg
            260                 265                 270

Phe Tyr Ser Met Leu Gly Asp Gly Asp Gly Gly Ser Val Arg Ser Glu
        275                 280                 285

Val Thr Thr Arg Gly Tyr Phe Leu Ser His Phe Ala Lys Tyr Ala Thr
    290                 295                 300

Gly Arg Met Arg Val Lys Ala Thr Leu Pro Glu Gly Ala Pro Ser Gly
305                 310                 315                 320

Ile Ser Ala Thr Ala Tyr Lys Asn Ala Glu Gly Asp Ile Ser Val Ile
                325                 330                 335

Leu Val Asn Ser Ser Ala Asn Val Met Gln Gly Leu Lys Ile Ala Leu
            340                 345                 350

Pro Phe Lys Ala Ala Lys Ala Val Lys Val Val Thr Thr Ser Gly Thr
```

```
               355                 360                 365
Thr Pro Ala Glu Thr Val Lys Lys Met Ala Gln Ser Lys Val Lys Leu
        370                 375                 380

Ala Gly Gly Val Asp Val Asp Ala Tyr Ser Val Val Thr Leu Leu Ile
385                 390                 395                 400

<210> SEQ ID NO 30
<211> LENGTH: 365
<212> TYPE: PRT
<213> ORGANISM: Mucilaginibacter paludis

<400> SEQUENCE: 30

Leu Lys Gly Asp Ala Ala Ile Asp Ala Ser Ala Val Gln Gln Thr Ile
1               5                   10                  15

Gln Gly Phe Gly Gly Ala Ser Ile Leu Ala Trp Gln Ala Asp Leu Thr
            20                  25                  30

Ser Asp Gln Arg Thr Lys Ala Phe Ser Thr Thr Ser Gly Ile Gly Met
                35                  40                  45

Ser Ile Leu Arg Val Met Val Pro Thr Ser Ser Ser Phe Ala Ala
        50                  55                  60

Glu Lys Pro Thr Ile Asp Ala Ala Lys Gly Phe Gly Ala Lys Val Val
65                  70                  75                  80

Ala Thr Ala Trp Asn Ala Pro Ala Ser Met Met Thr Gly Asn His Leu
                85                  90                  95

Asn Thr Ala Ser Tyr Gly Ala Phe Ala Ala His Ile Ser Ser Tyr Asn
            100                 105                 110

Thr Ala Val Gly Gly Val Tyr Ala Val Ser Pro Phe Asn Glu Pro Asn
        115                 120                 125

Tyr Ser Gly Ser Gly Trp Met Glu Ala Thr Ala Thr Glu Val Ala Asn
130                 135                 140

Phe Val Ala Ala Gln Gly Asn Asn Cys Gly Ala Pro Ile Met Ala Pro
145                 150                 155                 160

Glu Pro Phe Asn Met Asp Gln Thr Phe Ile Asn Thr Tyr Leu Ser Asn
                165                 170                 175

Ala Thr Ala Lys Ala Asn Thr Ser Phe Val Cys Gly His Ile Tyr Gly
            180                 185                 190

Lys Thr Pro Tyr Asn Leu Gly Ser Ile Gly Lys Ser Val Trp Met Thr
        195                 200                 205

Glu His Tyr Thr Asn Ser Ser Ile Ser Gly Asp Asp Trp Gly Asn Ala
210                 215                 220

Met Thr Ala Ala Lys Glu Ile His Asp Cys Met Asn Ser Gly Trp Ala
225                 230                 235                 240

Ala Tyr Val Trp Trp Tyr Ile Arg Arg Ser Tyr Gly Pro Ile Asn Glu
                245                 250                 255

Ser Ser Ala Ile Thr Lys Leu Gly Tyr Val Met Ala Gln Tyr Ala Arg
            260                 265                 270

Tyr Val Arg Pro Gly Tyr Ser Lys Ile Ser Cys Thr Ser Asn Pro Thr
        275                 280                 285

Ser Gly Val Tyr Val Thr Ala Tyr Lys Ser Gly Thr Lys Leu Val Ile
290                 295                 300

Val Ile Val Asn Gln Asn Ala Ala Thr Thr Tyr Gln Ser Phe Thr Leu
305                 310                 315                 320

Ser Gly Ile Thr Val Ser Gly Phe Asn Arg Tyr Tyr Thr Asn Ser Thr
                325                 330                 335
```

Ser Asn Leu Ala Ser Asn Ser Leu Thr Val Thr Gly Asn Thr Phe Gly
            340                 345                 350

Ile Asn Leu Thr Gly Ser Ser Val Thr Thr Leu Val Ser
            355                 360                 365

<210> SEQ ID NO 31
<211> LENGTH: 384
<212> TYPE: PRT
<213> ORGANISM: Dickeya chrysanthemi

<400> SEQUENCE: 31

Tyr Ala Asp Thr Val Lys Ile Asp Ala Asn Val Asn Tyr Gln Ile Ile
1               5                   10                  15

Gln Gly Phe Gly Gly Met Ser Gly Val Gly Trp Ile Asn Asp Leu Thr
            20                  25                  30

Thr Glu Gln Ile Asn Thr Ala Tyr Gly Ser Gly Val Gly Gln Ile Gly
        35                  40                  45

Leu Ser Ile Met Arg Val Arg Ile Asp Pro Asp Ser Ser Lys Trp Asn
50                  55                  60

Ile Gln Leu Pro Ser Ala Arg Gln Ala Val Ser Leu Gly Ala Lys Ile
65                  70                  75                  80

Met Ala Thr Pro Trp Ser Pro Pro Ala Tyr Met Lys Ser Asn Asn Ser
                85                  90                  95

Leu Ile Asn Gly Gly Arg Leu Leu Pro Ala Asn Tyr Ser Ala Tyr Thr
            100                 105                 110

Ser His Leu Leu Asp Phe Ser Lys Tyr Met Gln Thr Asn Gly Ala Pro
        115                 120                 125

Leu Tyr Ala Ile Ser Ile Gln Asn Glu Pro Asp Trp Lys Pro Asp Tyr
130                 135                 140

Glu Ser Cys Glu Trp Ser Gly Asp Glu Phe Lys Ser Tyr Leu Lys Ser
145                 150                 155                 160

Gln Gly Ser Lys Phe Gly Ser Leu Lys Val Ile Val Ala Glu Ser Leu
                165                 170                 175

Gly Phe Asn Pro Ala Leu Thr Asp Pro Val Leu Lys Asp Ser Asp Ala
            180                 185                 190

Ser Lys Tyr Val Ser Ile Ile Gly Gly His Leu Tyr Gly Thr Thr Pro
        195                 200                 205

Lys Pro Tyr Pro Leu Ala Gln Asn Ala Gly Lys Gln Leu Trp Met Thr
210                 215                 220

Glu His Tyr Val Asp Ser Lys Gln Ser Ala Asn Asn Trp Thr Ser Ala
225                 230                 235                 240

Ile Glu Val Gly Thr Glu Leu Asn Ala Ser Met Val Ser Asn Tyr Ser
                245                 250                 255

Ala Tyr Val Trp Trp Tyr Ile Arg Arg Ser Tyr Gly Leu Leu Thr Glu
            260                 265                 270

Asp Gly Lys Val Ser Lys Arg Gly Tyr Val Met Ser Gln Tyr Ala Arg
        275                 280                 285

Phe Val Arg Pro Gly Ala Leu Arg Ile Gln Ala Thr Glu Asn Pro Gln
290                 295                 300

Ser Asn Val His Leu Thr Ala Tyr Lys Asn Thr Asp Gly Lys Met Val
305                 310                 315                 320

Ile Val Ala Val Asn Thr Asn Asp Ser Asp Gln Met Leu Ser Leu Asn
                325                 330                 335

Ile Ser Asn Ala Asn Val Thr Lys Phe Glu Lys Tyr Ser Thr Ser Ala
            340                 345                 350

Ser Leu Asn Val Glu Tyr Gly Gly Ser Ser Gln Val Asp Ser Ser Gly
        355                 360                 365

Lys Ala Thr Val Trp Leu Asn Pro Leu Ser Val Thr Thr Phe Val Ser
    370                 375                 380

<210> SEQ ID NO 32
<211> LENGTH: 381
<212> TYPE: PRT
<213> ORGANISM: Meloidogyne incognita

<400> SEQUENCE: 32

Asp Asn Ile Ala Lys Ile Asn Ser Asp Ile Thr Tyr Gln Ser Ile Asp
1               5                   10                  15

Gly Phe Gly Gly Ser Ser Ala Trp Leu Gly Asn Ile Pro Asp Lys Gly
            20                  25                  30

Ile Gly Asn Ile Phe Gly Lys Leu Gly Leu Ser Ile Leu Arg Val Gly
        35                  40                  45

Ile Val Asp Leu Cys Lys Asn Gln Lys Trp Gly Asn Tyr Arg Cys Ile
    50                  55                  60

Gly Gln Glu Ala Leu Thr Ala Gln Lys Ala Ser Lys Tyr Gly Val Lys
65                  70                  75                  80

Ile Phe Ala Ser Pro Ser Thr Ser Pro Ile Ser Phe Lys Thr Asn Asn
                85                  90                  95

Asn Glu Val Met Gly Glu Leu Arg Glu Asp Lys Tyr Asn Asp Tyr Val
            100                 105                 110

Glu Tyr Leu Gln Ser Ala Val Asp Glu Leu Asn Lys Val Gly Val Asn
        115                 120                 125

Leu Tyr Ala Ile Ser Leu Gln Ser Glu Pro Asp Phe Ser Pro Pro Tyr
    130                 135                 140

Cys Ser Ile Lys Trp Ser Pro Lys Gln Ile Ala Ala Phe Leu Lys Ser
145                 150                 155                 160

Tyr Ser Arg Lys Ile Lys Gly Pro Lys Ile Met Ala Pro Glu Cys Ala
                165                 170                 175

His Phe Val Pro Glu Tyr Asn Asp Ala Ile Leu Asn Asn Pro Asp Val
            180                 185                 190

Ala Lys Gly Val Asp Ile Ile Ala Trp His Met Tyr Gly Met Gln Leu
        195                 200                 205

Val Ser Gln Thr Lys Ala Gln Lys Met Gly Lys Ser Ala Trp Met Thr
    210                 215                 220

Glu Lys Thr Asn Asp Gly Asn Asp Trp Lys Ser Phe Met Glu Thr Ala
225                 230                 235                 240

Lys Asp Ile His Asp Cys Met Thr Ile Ala Asn Tyr Asn Ala Tyr Val
                245                 250                 255

Tyr Phe Trp Phe Lys Asp Pro Lys Tyr Val Ser Ile Val Asp Asn Asn
            260                 265                 270

Tyr Glu Ile Thr Ser Arg Gly Tyr Ile Leu Gly Gln Tyr Ala Lys Tyr
        275                 280                 285

Ile Arg Pro Gly Tyr Phe Arg Ile Asn Ala Thr Glu Asn Pro Thr Thr
    290                 295                 300

Asn Ile Tyr Val Ser Ala Tyr Lys Gly Asn Gly Lys Val Ile Ile Val
305                 310                 315                 320

Ala Ile Asn Ile Gly Trp Pro Asp Lys Asn Gln Gln Phe Ser Ile Lys
                325                 330                 335

Arg Ile Lys Ser Phe Thr Pro Ile Ile Thr Ala Pro Asn Lys Asn Met

```
                340             345             350
Ile Asn Gly Thr Lys Ile Leu Val Lys Asn Gly Asn Phe Asn Tyr Leu
            355             360             365

Leu Pro Ala Met Ser Val Val Thr Phe Val Ser Val Asn
            370             375             380

<210> SEQ ID NO 33
<211> LENGTH: 381
<212> TYPE: PRT
<213> ORGANISM: Radopholus similis

<400> SEQUENCE: 33

Asn Ala Ala Thr Gly Ser Val Ala Leu Gly Ser Met Arg Gln Thr Ile
1               5                   10                  15

Gln Gly Phe Gly Gly Ser Ser Ala Trp Met Gly Ala Met Thr Asp Ala
            20                  25                  30

Gln Met Asn Thr Leu Phe Gly Asn Gly Asn Asn Gln Tyr Gly Leu
        35                  40                  45

Ser Leu Leu Arg Leu Arg Ile Asp Pro Gly Lys Ser Trp Ala Asn Glu
50                  55                  60

Leu Ser Asn Ala Gln Lys Ala Gly Ala Arg Gly Ala Gln Val Phe Ala
65                  70                  75                  80

Thr Pro Trp Ser Pro Pro Ala Ser Met Lys Ser Asn Asn Asn Val Val
                85                  90                  95

Gly Gly Ser Leu Asn Thr Ala Ser Tyr Gly Ala Tyr Ala Ala Tyr Leu
            100                 105                 110

Lys Ser Phe Val Asp Tyr Leu Lys Ala Gly Gly Val Ser Leu Tyr Ala
            115                 120                 125

Ile Ser Val Asn Asn Glu Pro Asp Ile Thr Val Thr Tyr Glu Ser Cys
130                 135                 140

Asp Trp Thr Ala Ala Gln Leu Val Asn Phe Val Lys Asn Tyr Gly Ser
145                 150                 155                 160

Ala Val Gly Thr Lys Leu Ile Ala Ala Glu Ser Phe Lys Phe Asn Lys
                165                 170                 175

Ala Leu Thr Asp Pro Ile Leu Ser Asp Ser Ser Ala Val Ser Gln Val
            180                 185                 190

Ser Ile Ile Ala Gly His Ile Tyr Gly Ser Gly Leu Ala Asp Tyr Ser
            195                 200                 205

Ser Ala Gln Asn Lys Gly Lys Gln Val Trp Met Thr Glu His Tyr Asn
210                 215                 220

Ala Gly Phe Asp Trp Thr Ser Met Met Ala Thr Ala Lys Glu Ile His
225                 230                 235                 240

Asp Ala Met Thr Val Ala Ser Tyr Asn Ala Tyr Val Trp Trp Trp Phe
                245                 250                 255

Val Asp Leu Asn Asn Glu Phe Thr Ser Leu Thr Asp Lys Ser Gly Asn
            260                 265                 270

Pro Thr Lys Arg Gly Tyr Ile Met Ala Gln Trp Ser Lys Tyr Ile Arg
            275                 280                 285

Pro Gly Tyr Thr Arg Val Asp Ala Thr Tyr Gln Pro Thr Thr Asn Val
290                 295                 300

Phe Leu Ser Ala Tyr Lys Ser Gly Ser Lys Val Val Leu Val Ala Val
305                 310                 315                 320

Asn Thr Gly Ser Ser Ala Val Ser Gln Thr Phe Ser Leu Ser Gly Gly
                325                 330                 335
```

```
Thr Ile Pro Ala Ser Phe Thr Pro His Ile Thr Ser Ser Lys Ser
                340                 345                 350

Leu Ser Asn Glu Ala Ser Val Ser Val Lys Ser Gly Ala Phe Thr Tyr
            355                 360                 365

Ser Leu Pro Gly Gln Ser Val Thr Thr Phe Val Ser Asn
        370                 375                 380

<210> SEQ ID NO 34
<211> LENGTH: 384
<212> TYPE: PRT
<213> ORGANISM: Clostridium sp. DL-VIII

<400> SEQUENCE: 34

Ala Ala Ala Ser Asp Thr Ile Asn Leu Ser Ser Lys Gln Gln Leu Ile
1               5                   10                  15

Arg Gly Phe Gly Ala Ala Ser Val Trp Cys Gly Ala Leu Ser Asp Ser
            20                  25                  30

Tyr Met Asn Thr Leu Tyr Asn Thr Ala Gly Leu Ser Ile Leu Ar

```
Gly Gly Lys Thr Ser Ser Val Ser Pro Tyr Val Ser Ser Ser
            340                 345                 350

Asn Met Ala Lys Gly Thr Asp Ile Ser Val Ser Asn Gly Ser Phe Thr
            355                 360                 365

Thr Thr Leu Pro Ala Gln Ser Val Thr Thr Phe Val Gly Thr Leu Ser
            370                 375                 380
```

<210> SEQ ID NO 35
<211> LENGTH: 385
<212> TYPE: PRT
<213> ORGANISM: Clostridium saccharoperbutylacetonicum

<400> SEQUENCE: 35

```
Thr Asn Asn Ala Thr Val Asn Leu Ser Ser Lys Gln Gln Leu Ile Thr
1               5                   10                  15

Gly Phe Gly Ala Ser Ser Ala Trp Cys Gly Ala Leu Asn Asp Ser Ser
            20                  25                  30

Met Asp Thr Leu Tyr Lys Asn Ile Gly Leu Ser Ile Leu Arg Val Arg
            35                  40                  45

Ile Asp Pro Asn Glu Gly Trp Asn Lys Gly Asp Tyr Ser Arg Trp Ala
50                  55                  60

Asp Glu Leu Ser Asn Ala Lys Lys Ala Ala Arg Gly Ala Ile Val
65                  70                  75              80

Phe Ala Thr Pro Trp Ser Pro Pro Ala Ser Met Lys Thr Asn Asn Ser
                    85                  90                  95

Ile Lys Gly Gln Gly Ser Leu Lys Ile Ser Ser Tyr Ala Asp Tyr Ala
            100                 105                 110

Ala Tyr Leu Lys Thr Phe Ala Asn Tyr Phe Ala Asn Asn Gly Val Pro
            115                 120                 125

Leu Tyr Ala Ile Ser Leu Gln Asn Glu Pro Asp Trp Lys Val Asp Tyr
130                 135                 140

Asp Gly Cys Leu Trp Thr Gly Asn Glu Leu Tyr Asp Phe Val Lys Ser
145                 150                 155                 160

Tyr Gly Ser Thr Ile Ser Lys Thr Val Lys Ile Ile Met Pro Glu Ser
                    165                 170                 175

Leu Asn Phe Asn Gln Ala Met Ser Asn Pro Thr Leu Asn Asp Pro Ala
            180                 185                 190

Ala Ser Ser Tyr Val Ser Ile Val Gly Gly His Leu Tyr Gly Ala Thr
            195                 200                 205

Ile Lys Asp Tyr Pro Leu Ala Arg Ser Glu Gly Lys Glu Leu Trp Met
            210                 215                 220

Thr Glu His Tyr Phe Gln Gly Glu Asn Ile Ser Ser Ser Met Asp Leu
225                 230                 235                 240

Ala Lys Glu Ile Asn Asp Cys Met Thr Ile Gly Asn Met Asn Ala Tyr
                    245                 250                 255

Val Tyr Trp Trp Ile Leu Asn Asp Gly Asn Gly Leu Tyr Thr Arg Ser
            260                 265                 270

Gly Gln Ala Asn Lys Arg Ala Tyr Val Leu Gly Gln Phe Ser Lys Phe
            275                 280                 285

Ile Arg Ser Gly Tyr Asn Arg Val Asn Thr Thr Ser Asn Pro Gln Ser
            290                 295                 300

Asn Val Tyr Leu Ser Ala Tyr Thr Gly Asn Asn Lys Val Val Ile Leu
305                 310                 315                 320

Ala Ile Asn Gln Gly Lys Ser Pro Val Thr Gln Ser Phe Asn Val Gln
```

```
              325                 330                 335
Asn Gly Lys Val Ser Ser Val Ser Ser Tyr Val Thr Ser Ala Thr Ser
              340                 345                 350

Asp Met Val Lys Ser Asn Ser Asp Ile Asn Val Thr Asn Gly Ser Phe
              355                 360                 365

Thr Ala Ser Leu Pro Ala Glu Ser Val Thr Thr Phe Val Gly Asp Ile
      370                 375                 380

Lys
385

<210> SEQ ID NO 36
<211> LENGTH: 388
<212> TYPE: PRT
<213> ORGANISM: Clostridium acetobutylicum

<400> SEQUENCE: 36

Ser Asn Asp Ala Thr Ile Asn Val Ala Ala Lys His Gln Thr Ile Arg
1               5                   10                  15

Gly Phe Gly Ala Ser Ser Ala Trp Cys Gly Ala Leu Ser Asp Thr Cys
              20                  25                  30

Met Asp Thr Leu Tyr Lys Asn Ala Gly Leu Asp Ile Leu Arg Val Arg
          35                  40                  45

Ile Ala Pro Asn Glu Gly Trp Asn Arg Gly Asp Tyr Arg Ala Trp Ala
 50                  55                  60

Asp Glu Leu Ser Asn Ala Lys Lys Val Arg Ala Arg Gly Gly Ile Val
65                  70                  75                  80

Phe Ala Thr Pro Trp Thr Pro Pro Ala Ser Met Lys Thr Asn Asn Thr
                  85                  90                  95

Thr Thr Gly Ala Asn Lys Gly Ser Leu Lys Pro Ser Ser Tyr Ala Ala
              100                 105                 110

Tyr Ala Ala Tyr Leu Lys Thr Phe Val Lys Tyr Met Ser Asp Asn Gly
          115                 120                 125

Ala Pro Leu Tyr Ala Leu Ser Leu Gln Asn Glu Pro Asp Trp Ala Pro
130                 135                 140

Asp Tyr Asp Ala Cys Thr Trp Thr Ala Gln Gln Phe His Asp Phe Leu
145                 150                 155                 160

Lys Gln Tyr Gly Ala Ser Leu Ser Ser Thr Ile Lys Ile Ile Met Pro
                165                 170                 175

Glu Ser Leu Gly Phe Asn Pro Ala Met Ser Asp Pro Thr Leu Asn Asp
              180                 185                 190

Pro Thr Thr Ala Gln Tyr Val Ser Ile Ile Gly His Leu Tyr Gly
          195                 200                 205

Ser Pro Ile Arg Asp Tyr Pro Leu Ala Arg Asn Lys Gly Lys Asp Ile
      210                 215                 220

Trp Met Thr Glu His Tyr Leu Glu Gly Asn Asp Pro Gly Thr Cys Val
225                 230                 235                 240

Lys Leu Ala Lys Glu Ile His Asp Cys Met Thr Ile Gly Asn Met Asn
                245                 250                 255

Ala Tyr Val Tyr Trp Trp Ile Ser Gly Asp Gln Asn Gly Leu Tyr Asn
              260                 265                 270

Thr Arg Thr Asn Glu Thr Tyr Lys Lys Thr Tyr Val Met Gly Gln Phe
          275                 280                 285

Ser Lys Phe Ile Gly Asn Gly Tyr Ser Arg Val Asp Ala Thr Asn Ser
      290                 295                 300
```

```
Pro Gln Ser Asn Val Tyr Val Ser Ala Tyr Thr Gly Asn Asn Lys Val
305                 310                 315                 320

Val Ile Val Ala Ile Asn Gln Gly Thr Tyr Pro Val Asn Gln Ser Phe
            325                 330                 335

Asn Val Gln Asn Ser Thr Val Ser Asn Val Ser Ser Trp Val Ser Ser
            340                 345                 350

Gly Thr Leu Asn Met Ala Lys Thr Asn Ser Asn Ile Ser Ala Ala Asn
            355                 360                 365

Gly Arg Phe Asn Ala Ser Leu Pro Ala Gln Ser Val Thr Thr Phe Val
            370                 375                 380

Ala Asp Leu Asn
385

<210> SEQ ID NO 37
<211> LENGTH: 388
<212> TYPE: PRT
<213> ORGANISM: Clostridium acetobutylicum

<400> SEQUENCE: 37

Ser Asn Asp Ala Thr Ile Asn Val Ala Ala Lys His Gln Thr Ile Arg
1               5                   10                  15

Gly Phe Gly Ala Ser Ser Ala Trp Cys Gly Ala Leu Ser Asp Thr Cys
            20                  25                  30

Met Asp Thr Leu Tyr Lys Asn Ala Gly Leu Asp Ile Leu Arg Val Arg
        35                  40                  45

Ile Ala Pro Asn Glu Gly Trp Asn Arg Gly Asp Tyr Arg Ala Trp Ala
    50                  55                  60

Asp Glu Leu Ser Asn Ala Lys Lys Val Arg Ala Arg Gly Gly Ile Val
65                  70                  75                  80

Phe Ala Thr Pro Trp Thr Pro Pro Ala Ser Met Lys Thr Asn Asn Thr
                85                  90                  95

Thr Thr Gly Ala Asn Lys Gly Ser Leu Lys Pro Ser Ser Tyr Ala Ala
            100                 105                 110

Tyr Ala Ala Tyr Leu Lys Thr Phe Val Lys Tyr Met Ser Asp Asn Gly
        115                 120                 125

Ala Pro Leu Tyr Ala Leu Ser Leu Gln Asn Glu Pro Asp Trp Ala Pro
    130                 135                 140

Asp Tyr Asp Ala Cys Thr Trp Thr Ala Gln Gln Phe His Asp Phe Leu
145                 150                 155                 160

Lys Gln Tyr Gly Ala Ser Leu Ser Ser Thr Ile Lys Ile Ile Met Pro
                165                 170                 175

Glu Ser Leu Gly Phe Asn Pro Ala Met Ser Asp Pro Thr Leu Asn Asp
            180                 185                 190

Pro Thr Thr Ala Gln Tyr Val Ser Ile Ile Gly His Leu Tyr Gly
        195                 200                 205

Ser Pro Ile Arg Asp Tyr Pro Leu Ala Arg Asn Lys Gly Lys Asp Ile
    210                 215                 220

Trp Met Thr Glu His Tyr Leu Glu Gly Asn Asp Pro Gly Thr Cys Val
225                 230                 235                 240

Lys Leu Ala Lys Glu Ile His Asp Cys Met Thr Ile Gly Asn Met Asn
                245                 250                 255

Ala Tyr Val Tyr Trp Trp Ile Ser Gly Asp Gln Asn Gly Leu Tyr Asn
            260                 265                 270

Thr Arg Thr Asn Glu Thr Tyr Lys Lys Thr Tyr Val Met Gly Gln Phe
        275                 280                 285
```

```
Ser Lys Phe Ile Gly Asn Gly Tyr Ser Arg Val Asp Ala Thr Asn Ser
    290                 295                 300

Pro Gln Ser Asn Val Tyr Val Ser Ala Tyr Thr Gly Asn Asn Lys Val
305                 310                 315                 320

Val Ile Val Ala Ile Asn Gln Gly Thr Tyr Pro Val Asn Gln Ser Phe
                325                 330                 335

Asn Val Gln Asn Ser Thr Val Ser Asn Val Ser Ser Trp Val Ser Ser
            340                 345                 350

Gly Thr Leu Asn Met Ala Lys Thr Asn Ser Asn Ile Ser Ala Ala Asn
        355                 360                 365

Gly Arg Phe Asn Ala Ser Leu Pro Ala Gln Ser Val Thr Thr Phe Val
    370                 375                 380

Ala Asp Leu Asn
385

<210> SEQ ID NO 38
<211> LENGTH: 73
<212> TYPE: PRT
<213> ORGANISM: Ruminococcus albus

<400> SEQUENCE: 38

Lys Gln Leu Trp Met Thr Glu Val Tyr Val Pro Asp Ser Asn Val Asp
1               5                   10                  15

Ser Asn Ile Trp Pro Asp Asn Leu Lys Gln Ala Val Ser Ile His Asp
            20                  25                  30

Ser Leu Val Val Gly Gly Met Gln Ala Tyr Val Val Trp Pro Leu Arg
        35                  40                  45

Arg Asn Tyr Ser Ile Leu Arg Glu Asp Thr His Lys Ile Ser Lys Arg
    50                  55                  60

Gly Tyr Ala Phe Ala Gln Tyr Ser Lys
65                  70

<210> SEQ ID NO 39
<211> LENGTH: 69
<212> TYPE: PRT
<213> ORGANISM: Xanthomonas perforans

<400> SEQUENCE: 39

Lys Gln Val Trp Met Thr Glu His Tyr Thr Asp Asn Thr Asp Gly Asn
1               5                   10                  15

Ala Trp Pro Ser Ala Leu Gly Val Ala Ser Glu Leu His Ala Ser Met
            20                  25                  30

Ala Ala Asn Phe Asn Ala Tyr Ile Trp Trp Tyr Ile Arg Arg Ser Tyr
        35                  40                  45

Gly Leu Ile Ser Glu Asn Gly Ala Val Ser Lys Arg Gly Tyr Ala Met
    50                  55                  60

Ser Gln Phe Ala Arg
65

<210> SEQ ID NO 40
<211> LENGTH: 73
<212> TYPE: PRT
<213> ORGANISM: Bacillus subtilis

<400> SEQUENCE: 40

Lys Asp Leu Trp Met Thr Glu Val Tyr Tyr Pro Asn Ser Asp Thr Asn
1               5                   10                  15
```

```
Ser Ala Asp Arg Trp Pro Glu Ala Leu Asp Val Ser Gln His Ile His
            20                  25                  30

Asn Ala Met Val Glu Gly Asp Phe Gln Ala Tyr Val Trp Trp Tyr Ile
            35                  40                  45

Arg Arg Ser Tyr Gly Pro Met Lys Glu Asp Gly Thr Ile Ser Lys Arg
 50                  55                  60

Gly Tyr Asn Met Ala His Phe Ser Lys
 65                  70
```

<210> SEQ ID NO 41
<211> LENGTH: 73
<212> TYPE: PRT
<213> ORGANISM: Paenibacillus sp.

<400> SEQUENCE: 41

```
Lys Glu Leu Trp Met Thr Glu Val Tyr Val Pro Asn Ser Asp Asn Asn
 1               5                  10                  15

Ser Ala Asp Arg Trp Pro Glu Ala Leu Asp Val Ala Tyr His Val His
            20                  25                  30

Asn Ala Met Val Glu Gly Asp Phe Gln Ala Tyr Thr Trp Trp Tyr Ile
            35                  40                  45

Arg Arg Gln Tyr Gly Pro Met Lys Asp Gly Asn Ile Ser Lys Arg
 50                  55                  60

Gly Tyr Met Met Ala Gln Phe Ser Lys
 65                  70
```

<210> SEQ ID NO 42
<211> LENGTH: 67
<212> TYPE: PRT
<213> ORGANISM: Clostridium papyrosolvens

<400> SEQUENCE: 42

```
Lys Glu Leu Trp Met Thr Glu Lys Tyr Phe Asp Asp Thr Thr Gly
 1               5                  10                  15

Asn Ile Met Asn Met Ser Lys Glu Ile His Asp Ser Met Val Thr Gly
            20                  25                  30

Asn Met Asn Ala Tyr Ile Tyr Trp Trp Ile Thr Trp Pro Asn Gly Leu
            35                  40                  45

Ala Thr Ser Ser Gly Thr Ile Tyr Lys Arg Ala Tyr Val Leu Gly Gln
 50                  55                  60

Phe Ala Lys
 65
```

<210> SEQ ID NO 43
<211> LENGTH: 70
<212> TYPE: PRT
<213> ORGANISM: Cellvibrio japonicus

<400> SEQUENCE: 43

```
Lys Glu Val Trp Met Thr Glu His Tyr Thr Asp Ser Lys Asn Asp Ala
 1               5                  10                  15

Asp Val Trp Pro Leu Ala Leu Asp Val Gly Val Glu Leu His Arg Ser
            20                  25                  30

Met Ala Ala Asn Phe Asn Ala Tyr Ile Trp Trp Tyr Ile Arg Arg Phe
            35                  40                  45

Tyr Ser Phe Ile Lys Glu Asp Gly Gln Val Ser Lys Arg Gly Tyr Ile
 50                  55                  60

Met Ser Gln Tyr Ala Arg
```

65                  70

<210> SEQ ID NO 44
<211> LENGTH: 70
<212> TYPE: PRT
<213> ORGANISM: Dickeya chrysanthemi

<400> SEQUENCE: 44

Lys Gln Leu Trp Met Thr Glu His Tyr Val Asp Ser Lys Gln Ser Ala
1               5                   10                  15

Asn Asn Trp Thr Ser Ala Ile Glu Val Gly Thr Glu Leu Asn Ala Ser
            20                  25                  30

Met Val Ser Asn Tyr Ser Ala Tyr Val Trp Trp Tyr Ile Arg Arg Ser
        35                  40                  45

Tyr Gly Leu Leu Thr Glu Asp Gly Lys Val Ser Lys Arg Gly Tyr Val
    50                  55                  60

Met Ser Gln Tyr Ala Arg
65                  70

<210> SEQ ID NO 45
<211> LENGTH: 20
<212> TYPE: PRT
<213> ORGANISM: Bacillus subtilis

<400> SEQUENCE: 45

Gly Lys Asp Leu Trp Met Thr Glu Val Tyr Tyr Pro Asn Ser Asp Thr
1               5                   10                  15

Asn Ser Ala Asp
            20

<210> SEQ ID NO 46
<211> LENGTH: 18
<212> TYPE: PRT
<213> ORGANISM: Meloidogyne incognita

<400> SEQUENCE: 46

Gly Lys Ser Ala Trp Met Thr Glu Lys Thr Asn Asp Gly Asn Asp Trp
1               5                   10                  15

Lys Ser

<210> SEQ ID NO 47
<211> LENGTH: 18
<212> TYPE: PRT
<213> ORGANISM: Radopholus similis

<400> SEQUENCE: 47

Gly Lys Gln Val Trp Met Thr Glu His Tyr Asn Ala Gly Phe Asp Trp
1               5                   10                  15

Thr Ser

<210> SEQ ID NO 48
<211> LENGTH: 20
<212> TYPE: PRT
<213> ORGANISM: Paludibacter propionicigenes

<400> SEQUENCE: 48

Gly Lys Lys Ile Trp Met Thr Glu His Tyr Tyr Asp Asn Ala Asn Asn
1               5                   10                  15

Asn Ile Ser Val
            20

```
<210> SEQ ID NO 49
<211> LENGTH: 19
<212> TYPE: PRT
<213> ORGANISM: Mucilaginibacter paludia

<400> SEQUENCE: 49

Gly Lys His Val Trp Met Thr Glu Tyr Tyr Ile Asn Gly Gln Thr Asp
1               5                   10                  15

Ile Thr Ala

<210> SEQ ID NO 50
<211> LENGTH: 18
<212> TYPE: PRT
<213> ORGANISM: Clostridium sp. DL-VIII

<400> SEQUENCE: 50

Gly Lys Glu Leu Trp Met Thr Glu His Leu Leu Asn Asp Gln Ser Ile
1               5                   10                  15

Ser Gly

<210> SEQ ID NO 51
<211> LENGTH: 18
<212> TYPE: PRT
<213> ORGANISM: Clostridium saccharoperbutylacetonicum

<400> SEQUENCE: 51

Gly Lys Glu Leu Trp Met Thr Glu His Tyr Phe Gln Gly Glu Asn Ile
1               5                   10                  15

Ser Ser

<210> SEQ ID NO 52
<211> LENGTH: 18
<212> TYPE: PRT
<213> ORGANISM: Clostriduim acetobutylicum

<400> SEQUENCE: 52

Gly Lys Asp Ile Trp Met Thr Glu His Tyr Leu Glu Gly Asn Asp Pro
1               5                   10                  15

Gly Thr

<210> SEQ ID NO 53
<211> LENGTH: 18
<212> TYPE: PRT
<213> ORGANISM: Clostridium acetobutylicum

<400> SEQUENCE: 53

Gly Lys Asp Ile Trp Met Thr Glu His Tyr Leu Glu Gly Asn Asp Pro
1               5                   10                  15

Gly Thr

<210> SEQ ID NO 54
<211> LENGTH: 18
<212> TYPE: PRT
<213> ORGANISM: Clostridium acetobutylicum

<400> SEQUENCE: 54

Gly Lys Asp Ile Trp Met Thr Glu His Tyr Leu Glu Gly Asn Asp Pro
1               5                   10                  15

Gly Thr
```

<210> SEQ ID NO 55
<211> LENGTH: 18
<212> TYPE: PRT
<213> ORGANISM: Clostridium papyrosolvens

<400> SEQUENCE: 55

Gly Lys Glu Leu Trp Met Thr Glu Lys Tyr Phe Asp Asp Asp Thr Thr
1               5                   10                  15

Gly Asn

<210> SEQ ID NO 56
<211> LENGTH: 18
<212> TYPE: PRT
<213> ORGANISM: Dickeya chrysanthemi

<400> SEQUENCE: 56

Gly Lys Gln Leu Trp Met Thr Glu His Tyr Val Asp Ser Lys Gln Ser
1               5                   10                  15

Ala Asn

<210> SEQ ID NO 57
<211> LENGTH: 16
<212> TYPE: PRT
<213> ORGANISM: Bacillus subtilis

<400> SEQUENCE: 57

Gln Ala Tyr Val Trp Trp Tyr Ile Arg Arg Ser Tyr Gly Pro Met Lys
1               5                   10                  15

<210> SEQ ID NO 58
<211> LENGTH: 18
<212> TYPE: PRT
<213> ORGANISM: Meloidogyne incognita

<400> SEQUENCE: 58

Asn Ala Tyr Val Tyr Phe Trp Phe Lys Asp Pro Lys Tyr Val Ser Ile
1               5                   10                  15

Val Asp

<210> SEQ ID NO 59
<211> LENGTH: 20
<212> TYPE: PRT
<213> ORGANISM: Radopholus similis

<400> SEQUENCE: 59

Asn Ala Tyr Val Trp Trp Trp Phe Val Asp Leu Asn Asn Glu Phe Thr
1               5                   10                  15

Ser Leu Thr Asp
            20

<210> SEQ ID NO 60
<211> LENGTH: 20
<212> TYPE: PRT
<213> ORGANISM: Paludibacter propionicigenes

<400> SEQUENCE: 60

Asn Ala Tyr Val Trp Trp Trp Val Leu Pro Leu Asn Gly Ser Ile Cys
1               5                   10                  15

Asn Leu Ile Asn
            20

<210> SEQ ID NO 61

```
<211> LENGTH: 19
<212> TYPE: PRT
<213> ORGANISM: Mucilaginibacter paludis

<400> SEQUENCE: 61

Ser Thr Tyr Phe Trp Trp Trp Val Asn Asp Asn Asp Thr Asn Val Asn
1               5                   10                  15

Leu Val Thr

<210> SEQ ID NO 62
<211> LENGTH: 17
<212> TYPE: PRT
<213> ORGANISM: Clostridium sp. DL-VIII

<400> SEQUENCE: 62

Asn Ala Tyr Val Trp Trp Trp Val Ile Ser Asp Ser Asn Gly Leu Tyr
1               5                   10                  15

Asn

<210> SEQ ID NO 63
<211> LENGTH: 17
<212> TYPE: PRT
<213> ORGANISM: Clostridium saccharoperbutylacetonicum

<400> SEQUENCE: 63

Asn Ala Tyr Val Tyr Trp Trp Ile Leu Asn Asp Gly Asn Gly Leu Tyr
1               5                   10                  15

Thr

<210> SEQ ID NO 64
<211> LENGTH: 17
<212> TYPE: PRT
<213> ORGANISM: Clostridium acetobutylicum

<400> SEQUENCE: 64

Asn Ala Tyr Val Tyr Trp Trp Ile Ser Gly Asp Gln Asn Gly Leu Tyr
1               5                   10                  15

Asn

<210> SEQ ID NO 65
<211> LENGTH: 17
<212> TYPE: PRT
<213> ORGANISM: Clostridium acetobutylicum

<400> SEQUENCE: 65

Asn Ala Tyr Val Tyr Trp Trp Ile Ser Gly Asp Gln Asn Gly Leu Tyr
1               5                   10                  15

Asn

<210> SEQ ID NO 66
<211> LENGTH: 17
<212> TYPE: PRT
<213> ORGANISM: Clostridium acetobutylicum

<400> SEQUENCE: 66

Asn Ala Tyr Val Tyr Trp Trp Ile Ser Gly Asp Gln Asn Gly Leu Tyr
1               5                   10                  15

Asn

<210> SEQ ID NO 67
<211> LENGTH: 16
```

```
<212> TYPE: PRT
<213> ORGANISM: Clostridium papyrosolvens

<400> SEQUENCE: 67

Asn Ala Tyr Ile Tyr Trp Trp Ile Thr Trp Pro Asn Gly Leu Ala Thr
1               5                   10                  15

<210> SEQ ID NO 68
<211> LENGTH: 16
<212> TYPE: PRT
<213> ORGANISM: Dickeya chrysanthemi

<400> SEQUENCE: 68

Ser Ala Tyr Val Trp Trp Tyr Ile Arg Arg Ser Tyr Gly Leu Leu Thr
1               5                   10                  15

<210> SEQ ID NO 69
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (5)..(6)
<223> OTHER INFORMATION: Xaa can be any naturally occurring amino acid
      other than Arg

<400> SEQUENCE: 69

Trp Trp Trp Ile Xaa Xaa
1               5

<210> SEQ ID NO 70
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (5)..(6)
<223> OTHER INFORMATION: Xaa can be any naturally occurring amino acid
      other than Arg

<400> SEQUENCE: 70

Trp Trp Trp Val Xaa Xaa
1               5

<210> SEQ ID NO 71
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (5)..(6)
<223> OTHER INFORMATION: Xaa can be any naturally occurring amino acid
      other than Arg

<400> SEQUENCE: 71

Trp Trp Trp Phe Xaa Xaa
1               5

<210> SEQ ID NO 72
<211> LENGTH: 6
<212> TYPE: PRT
<213> ORGANISM: Artificial Sequence
<220> FEATURE:
```

```
<223> OTHER INFORMATION: synthetic
<220> FEATURE:
<221> NAME/KEY: MISC_FEATURE
<222> LOCATION: (5)..(6)
<223> OTHER INFORMATION: Xaa can be any naturally occurring amino acid
      other than Arg

<400> SEQUENCE: 72

Trp Phe Trp Ile Xaa Xaa
1               5

<210> SEQ ID NO 73
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (5)..(6)
<223> OTHER INFORMATION: Xaa can be any naturally occurring amino acid
      other than Arg

<400> SEQUENCE: 73

Trp Phe Trp Val Xaa Xaa
1               5

<210> SEQ ID NO 74
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (5)..(6)
<223> OTHER INFORMATION: Xaa can be any naturally occurring amino acid
      other than Arg

<400> SEQUENCE: 74

Trp Phe Trp Phe Xaa Xaa
1               5

<210> SEQ ID NO 75
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (5)..(6)
<223> OTHER INFORMATION: Xaa can be any naturally occurring amino acid
      other than Arg

<400> SEQUENCE: 75

Tyr Trp Trp Ile Xaa Xaa
1               5

<210> SEQ ID NO 76
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (5)..(6)
<223> OTHER INFORMATION: Xaa can be any naturally occurring amino acid
      other than Arg
```

```
<400> SEQUENCE: 76

Tyr Trp Trp Val Xaa Xaa
1               5

<210> SEQ ID NO 77
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (5)..(6)
<223> OTHER INFORMATION: Xaa can be any naturally occurring amino acid
      other than Arg

<400> SEQUENCE: 77

Tyr Trp Trp Phe Xaa Xaa
1               5

<210> SEQ ID NO 78
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (5)..(6)
<223> OTHER INFORMATION: Xaa can be any naturally occurring amino acid
      other than Arg

<400> SEQUENCE: 78

Tyr Phe Trp Ile Xaa Xaa
1               5

<210> SEQ ID NO 79
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (5)..(6)
<223> OTHER INFORMATION: Xaa can be any naturally occurring amino acid
      other than Arg

<400> SEQUENCE: 79

Tyr Phe Trp Val Xaa Xaa
1               5

<210> SEQ ID NO 80
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (5)..(6)
<223> OTHER INFORMATION: Xaa can be any naturally occurring amino acid
      other than Arg

<400> SEQUENCE: 80

Tyr Phe Trp Phe Xaa Xaa
1               5
```

GLYCOSYL HYDROLASE XYLANASES, COMPOSITIONS AND METHODS OF USE FOR EFFICIENT HYDROLYSIS AND PROCESSING OF XYLAN

CROSS-REFERENCE TO RELATED APPLICATIONS

This application claims the benefit of U.S. Provisional Application No. 62/023,116, filed Jul. 10, 2014, which is incorporated by reference in its entirety for all purposes.

STATEMENT REGARDING FEDERALLY SPONSORED RESEARCH OR DEVELOPMENT

This invention is owned by and was made with government support from the USDA Forest Service. The government has certain rights in the invention.

BACKGROUND OF THE INVENTION

Xylanases (endo-β-1,4-xylanase, EC 3.2.1.8) hydrolyze internal β-1,4-xylosidic linkages in xylan to produce smaller molecular weight xylose and xylo-oligomers. Xylans are polysaccharides formed from β-1,4-glycoside-linked D-xylopyranoses. Xylanases are very useful in multiple commercial applications, including for dough preparation or bread product preparation fruit and vegetable processing, breaking down agricultural waste, manufacturing animal feed as well as in lignocellulose pretreatment and pulp and paper production. Cellulose and hemicellulose materials which can be converted into fermentable sugars are considered a very useful and under-utilized source of renewable biomass materials. Individual β-1,4-glucose chains once synthesized, self-associate through hydrogen bonding to form semi-crystalline cellulose microfibrils (cellulose). The cellulose microfibrils are embedded in a polysaccharide matrix formed of hemicelluloses such as xylan, galactoglucomannan and xyloglucan all of which may be associated with other lower abundance biomass polysaccharides such as arabinans, mannans; pectins including galacturonans and galactans and various other β-1,3 and β-1,4 glucans all of which are dependent upon the plant source and the cellulosic tissue in question. The hemicellulose matrix is also typically surrounded and cross linked with polyphenolic lignins. From the tight interactions that exist between cellulose, hemicellulose and lignin, it is very difficult and expensive to break down this recalcitrant matrix of biomass to yield desired mixtures of oligosaccharides or fermentable simple sugars.

The primary hemicellulose from hardwood and crop residues is a glucuronoxylan (GX) consisting of a chain of β-1,4-linked xylose residues randomly substituted with α-1,2-linked glucuronic acid (GA) residues. Frequency of substitution has been shown to be as high as 1 GA for every 6 xyloses. In hardwoods, unaltered GX is additionally acetylated to a high degree on the O-2 or O-3 (or O-2 and O-3) hydroxyl positions. Commercial extraction of these polysaccharides typically is done under alkaline conditions which deacetylates these polysaccharides. This is the form of GX commonly used for laboratory studies. Other lower yielding extraction procedures must be implemented to obtain a glucuronoacetylxylan polysaccharide. Xylan is the second most abundant hemicellulose in softwood species next to galactoglucomannan, accounting for just less than half of the total hemicellulose. This source of xylan is in the form of glucuronoarabinoxylan with periodic GA substitutions and α-1,2-linked arabinofuranose substitution on the O-2 or O-3 (or O-2 and O-3) hydroxyl positions of xylose. Xylans from other sources such as grains (wheat, WAX) typically consist of an arabinoxylan, having patterns of arabinofuranose substitution similar to softwoods, but lacking the GA substitution.

The glycosyl hydrolase (GH) family 30 (GH30) enzymes (Cantarel, et al., 2009) have recently been redefined (St. John, et al., 2010). The new family composition consists of eight subfamilies that can be assigned into two structurally and phylogenetically distinguishable groups. Biochemical and structural studies have shown the enzymes in subfamily 8 to have unique characteristics in the degradation of the hemicellulosic polymer glucuronoxylan (St. John, et al., 2006; Vrsanska, et al., 2007; Hurlbert & Preston, 2001).

Accordingly, a need exists for novel glycosyl hydrolase enzymes, compositions and methods of use which can more efficiently convert plant or other cellulosic or hemicellulosic materials into fermentable sugars.

SUMMARY OF THE INVENTION

The present invention provides a functionally unique subset of GH30 subfamily 8 xylanases (GH30-8) with GA-independent endo-β-1,4-xylanase activity, compositions comprising an effective amount of the GH30-8 xylanases of the present invention, methods of synthesis and methods of use thereof.

In a first aspect, the invention encompasses an isolated GA-independent GH30-8 enzyme or variant thereof exhibiting xylanase activity. The enzyme or variant includes the amino acid sequence (W or Y)(W or F)W(I or V or F)(not R)(not R) (SEQ ID NOs:69-80) within the β8-α8 loop of the enzyme or variant.

In an alternate aspect, the invention comprises an isolated GA-independent GH30-8 enzyme or variant thereof exhibiting xylanase activity comprising at least one of SEQ ID NOs: 1-4 in the β7-α7 and β8-α8 loops, wherein the amino acid sequence (W or Y)(W or F)W(I or V or F)(not R)(not R) (SEQ ID NOs:69-80) is within the β8-α8 loop of the enzyme or variant.

In an alternate aspect, the invention comprises an isolated GA-independent GH30-8 enzyme exhibiting xylanase activity or variant comprising an amino acid sequence that is at least 30% identical to an amino acid sequence selected from the group consisting of G7M3Z8, M1N0D3, Q97TI2, F7ZYN8, F0KEL6, C0IQA1, C0IQA2, B3TJG3, E4T705, H1YFT8, and F1TBY8.

In some embodiments, GA-independent GH30-8 enzyme or variant of the invention includes an amino acid sequence that is at least 30% identical to SEQ ID NO:1 residues 33-420 (Q97TI2), SEQ ID NO:2 residues 32-421 (F1TBY8), SEQ ID NO:3 beginning at residue 45 (E4T705), SEQ ID NO:4 beginning at residue 33 (H1YFT8), SEQ ID NO:32 (C0IQA1), SEQ ID NO:33 (B3TJG3), SEQ ID NO:34 (G7M3Z8), SEQ ID NO:35 (M1N0D3), SEQ ID NO:36 (F7ZYN8), or SEQ ID NO:37 (F0KEL6). In some such embodiments, the GA-independent GH30-8 enzyme or variant includes an amino acid sequence that is at least 80% identical to the selected amino acid sequence. In some such embodiments, the GA-independent GH30-8 enzyme or variant includes an amino acid sequence that is at least 95% identical to the selected amino acid sequence.

In some embodiments, the GA-independent GH30-8 enzyme or variant includes the amino acid sequence of SEQ ID NO:1 residues 33-420 (Q97TI2), SEQ ID NO:2 residues 32-421 (F1TBY8), SEQ ID NO:3 beginning at residue 45

(E4T705), SEQ ID NO:4 beginning at residue 33 (H1YFT8), SEQ ID NO:32 (C0IQA1), SEQ ID NO:33 (B3TJG3), SEQ ID NO:34 (G7M3Z8), SEQ ID NO:35 (M1N0D3), SEQ ID NO:36 (F7ZYN8), SEQ ID NO:37 (F0KEL6), or the amino acid sequence of C0IQA2.

In some embodiments, the GA-independent GH30-8 enzyme is XynQ97.

In some embodiments, GA-independent GH30-8 enzyme is XynC71 (aka CpXyn30A).

In a second aspect, the invention encompasses a GH30-8 enzyme composition. The composition includes a first polypeptide having xylanase activity that includes the amino acid sequence (W or Y)(W or F)W(I or V or F)(not R)(not R) (SEQ ID NOs:69-80), and a second polypeptide different from the first having xylanase activity that also includes the amino acid sequence (W or Y)(W or F)W(I or V or F)(not R)(not R) (SEQ ID NOs:69-80). The GH30-8 enzyme composition is capable of hydrolyzing a lignocellulosic biomass material.

In some embodiments, the composition further includes at least one additional protein having enzymatic activity.

In some embodiments, the first polypeptide, the second polypeptide, or both include an amino acid sequence that at least 30% identical to SEQ ID NO:1 residues 3.3-420 (Q97TI2), SEQ ID NO:2 residues 32-421 (F1TBY8), SEQ ID NO:3 beginning at residue 45 (E4T705), SEQ ID NO:4 beginning at residue 33 (H1YFT8), SEQ ID NO:32 (C0IQA1), SEQ ID NO:33 (B3TJG3), SEQ ID NO:34 (G7M3Z8), SEQ ID NO:35 (M1N0D3), SEQ ID NO:36 (F7ZYN8), or SEQ ID NO:37 (F0KEL6). In some such embodiments, the first polypeptide, the second polypeptide, or both include an amino acid sequence that is at least 80% identical to the selected amino acid sequence. In some such embodiments, the first polypeptide, the second polypeptide, or both include an amino acid sequence that is at least 95% identical to the selected amino acid sequence.

In some embodiments, the first polypeptide, the second polypeptide, or both include an amino acid sequence selected from SEQ ID NO:1 residues 33-420 (Q97TI2), SEQ ID NO:2 residues 32-421 (F1TBY8), SEQ ID NO:3 beginning at residue 45 (E4T705), SEQ ID NO:4 beginning at residue 33 (H1YFT8), SEQ ID NO:32 (C0IQA1), SEQ ID NO:33 (B3TJG3), SEQ ID NO:34 (G7M3Z8), SEQ ID NO:35 (M1N0D3), SEQ ID NO:36 (F7ZYN8), SEQ ID NO:37 (F0KEL6), or the amino acid sequence of C0IQA2.

In some embodiments, the amount of polypeptides having xylanase activity relative to the total amount of proteins in the enzyme composition is about 10 wt. % to about 20 wt. %.

In a third aspect, the disclosure encompasses a method of hydrolyzing or digesting a lignocellulosic biomass material comprising hemicelluloses, cellulose, or both. The method includes the steps of contacting the GH30-8 enzyme composition described above with the lignocellulosic biomass mixture.

In some embodiments, the lignocellulosic biomass mixture comprises an agricultural crop, a byproduct of a food/feed production, a lignocellulosic waste product, a plant residue, or waste paper.

In some embodiments, the biomass material in the lignocellulosic biomass mixture is subjected to pretreatment, wherein the pretreatment is an acidic pretreatment or a basic pretreatment. In some such embodiments, the pretreatment includes a thermal, aqueous or thermomechanical pulping.

In some embodiments, the GH30-8 enzyme composition is used in an amount and under conditions and for a duration sufficient to convert at least 60% to 90% of the xylan in the biomass material into xylooligosaccharides.

Other objects, features and advantages of the present invention will become apparent after review of the specification, claims and drawings.

INCORPORATION BY REFERENCE

All publications, patents, and patent applications mentioned in this specification are herein incorporated by reference to the same extent as if each individual publication, patent, and patent application was specifically and individually indicated to be incorporated by reference.

BRIEF DESCRIPTION OF THE DRAWINGS

The present invention will be better understood and features, aspects and advantages other than those set forth above will become apparent when consideration is given to the following detailed description thereof.

The patent or application file contains at least one drawing executed in color. Copies of this patent or patent application publication with color drawings will be provided by the Office upon request and payment of the necessary fee.

FIG. 7A. Small scale sequence alignment highlighting the β7-α7 and β8-α8 region of the GA-dependent GH30-8 enzymes with the GA-independent CpXyn30A (C7I, Cp_F1TBY8) included for comparison. The sequence labeled Bs_Q45070 is SEQ ID NO:5, residues 223-295; the sequence labeled Cs_M1MLA3 is SEQ ID NO:15, residues 223-295; the sequence labeled Cp_F1TBY8 is SEQ ID NO:2, residues 258 to 324; The sequence labeled Ra_E6UFE8 is SEQ ID NO:38; the sequence labeled Cj_B3PEH7 is SEQ ID NO:9, residues 220 to 292; the sequence labeled Xp_F0BZ40 is SEQ ID NO:39; the sequence labeled Ec_Q46961 is SEQ ID NO:31, residues 219 to 288.

FIG. 7B. The native DNA coding sequence of CpXyn30A encodes a protein of 628 amino acids including a N-terminus secretion signal sequence, a C-terminal family 6 carbohydrate binding module and two C-terminal dockerin domains for interaction of the secreted, mature form of CpXyn30A with a cellulosome complex.

FIG. 7C. In support of the qualitative sequence alignment in FIG. 7A, a phylogenetic tree showing that CpXyn30A (Cp_F1TBY8) with its unique sequence in the β7-α7 and β8-α8 loop regions still groups confidently with the canonical GH30-8 enzymes.

FIG. 14. SEQ ID NO: 1. Amino acid sequence of UniProt accession Q97TI2 having the named protein expression product Q97 (aka XynQ97, CaXynQ97, CaXyn30A, Q97_RCN and XynQ97_RCN).

FIG. 15. SEQ ID NO: 2. Amino acid sequence of UniProt accession F1TBY8 having 100% identity to the obsolete UniProt accession C7IMC9 and having the named protein expression product C7I (aka XynC7I, CpXynC7I and CpXyn30A).

FIG. 16. SEQ ID NO: 3. Amino acid sequence of UniProt accession E4T705 and having the named protein expression product PpXyn30A.

FIG. 17. SEQ ID NO: 4. Amino acid sequence of UniProt accession H1YFT8 and having the named protein expression product MpXyn30A.

FIG. 18. The β2-α2 loop region of CpXyn30A showing a fine difference between the structure of this enzyme and the canonical GH30-8 subfamily of enzymes.

DETAILED DESCRIPTION OF THE INVENTION

I. In General

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned here are incorporated by reference for all purposes including describing and disclosing the chemicals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

II. The Invention

The present invention provides a functionally unique subset of GH30 subfamily 8 xylanases (GH30-8) with endo-β-1,4-xylanase activity, compositions comprising an effective amount of the GH30-8 xylanases of the present invention, methods of synthesis and methods of use thereof.

GH30-8 Xylanases.

Glycoside hydrolase enzymes defined in family 30 (GH30) have at least 8 subfamilies (GH30-1 through GH30-8). Enzymes classified into the GH30-8 subfamily constitute a well characterized group of endoxylanases which cleave the β-1,4-xylosidic linkage of xylan only upon recognition of the α-1,2-linked 4-O-methylglucuronic acid (glucuronic acid, GA) side chain appendage common to many xylan types and sources (St. John, et al., 2010; St. John, et al., 2006). Cleavage of the xylan chain occurs toward the polymer reducing terminus relative to the target glucuronic acid, such that the GA appendage is positioned penultimate to the new reducing terminus.

Figure 1:
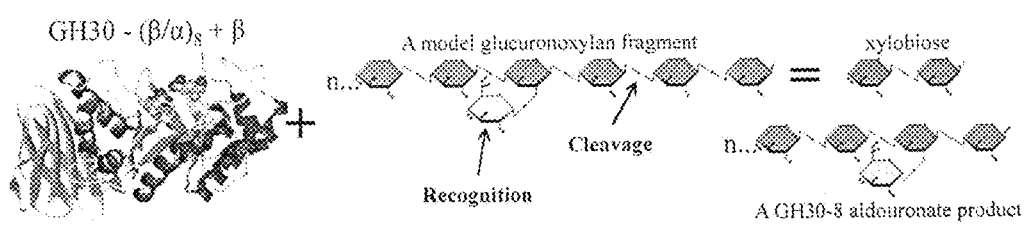
FIG. 1. Exemplified glucuronoxylan processing by canonical GA-dependent GH30-8 xylanases.

Limit hydrolysis of glucuronoxylan by these "GA-dependent" xylanases primarily result in a distribution of aldouronates in which each contains a single GA appendage substituted on the xylose penultimate to the reducing terminal of the resulting aldouronate (FIG. 1). The way in which these enzymes function to perform this specific type of glucuronoxylan chain cleavage has been described through biochemical studies and more recently from a detailed understanding of the protein structure with associated xylan derived ligands (FIGS. 2 & 3) (St. John et al., 2011; Urbanikova et al., 2011).

Before the enzymes of the present invention were identified and pursued, it was strongly established and widely agreed upon that GH30-8 enzymes were restricted to cleaving the β-1,4-linkage of xylan next to a GA substitution (FIGS. 1, 21). Inherent in that understanding is that the mechanism which allowed for that to occur, if it were to not be what it is, then the enzyme may no longer function. Thus, these canonical GA-dependent GH30-8 xylanases, therefore are known to require GA for their function.

Figure 6:
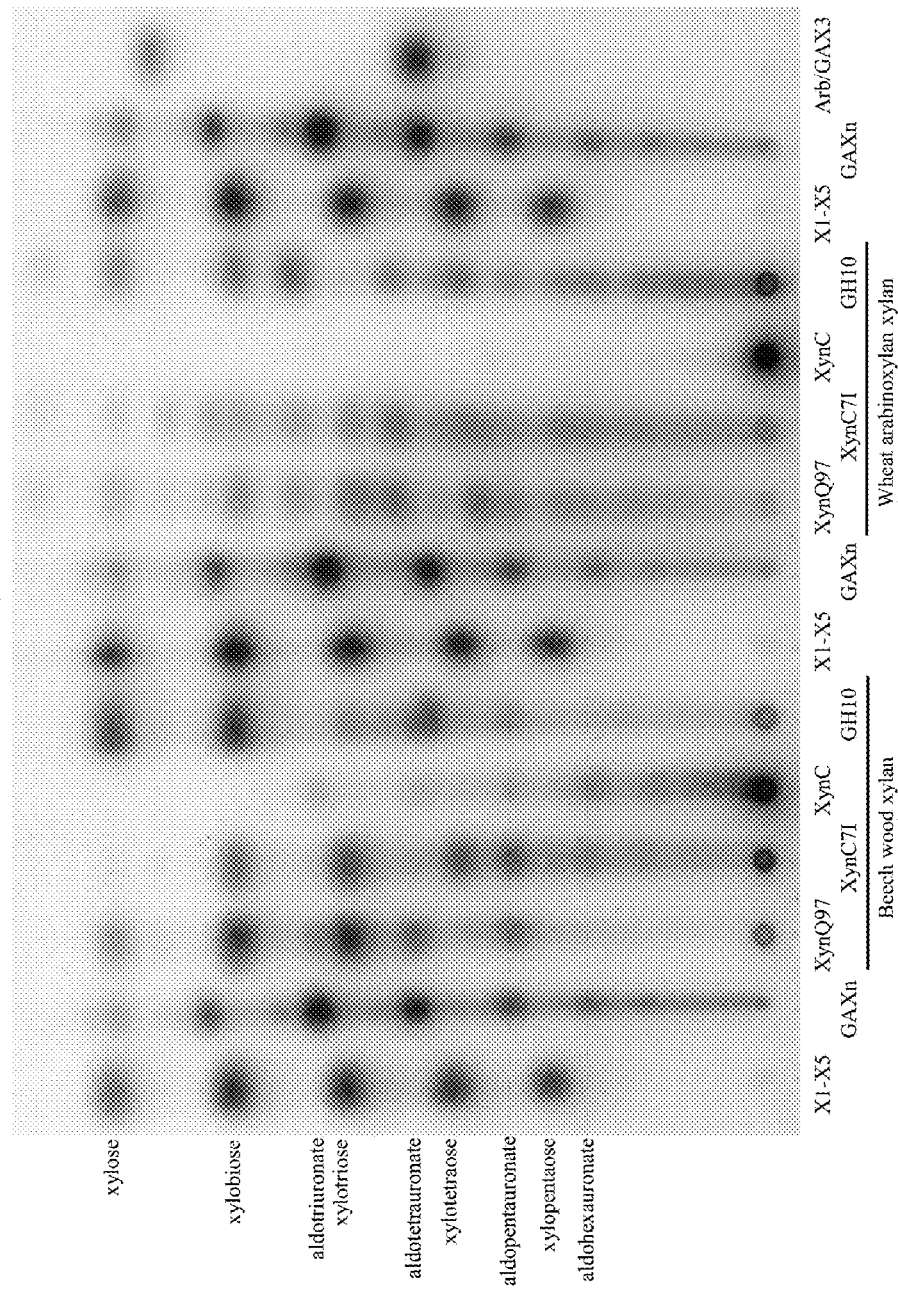
FIG. 6. Limit hydrolysis product analysis by thin layer chromatography, comparing the hydrolysis products of the GA-independent CpXyn30A (C7I) and CaXyn30A (Q97) enzymes to the canonical GA-dependent GH30-8 xylanase XynC from *Bacillus subtilis* and a GH10 family xylanase.

The presently disclosed, functionally distinct subset of GH30-8 xylanases and compositions thereof have a relaxed (or expanded range of) substrate specificity which results in a gain of function, because to function, they do not require the O-2 linked GA. These "GA-independent" xylanases are thus able to hydrolyze diverse polymeric xylans, including glucuronoxylans (GX) such as sweetgum wood xylan (SGX) and beech wood xylan (BX), arabinoxylans such as wheat arabinoxylan (WAX) and neutral xylooligosaccharide (e.g. X6) to smaller xylooligosaccharides and substituted xylooligosaccharides. Such classes of compositions cannot be hydrolyzed by the typical GA-dependent GH30-8 xylanases, which require the O-2 linked glucuronic acid (FIG. 6).

Figure 5:
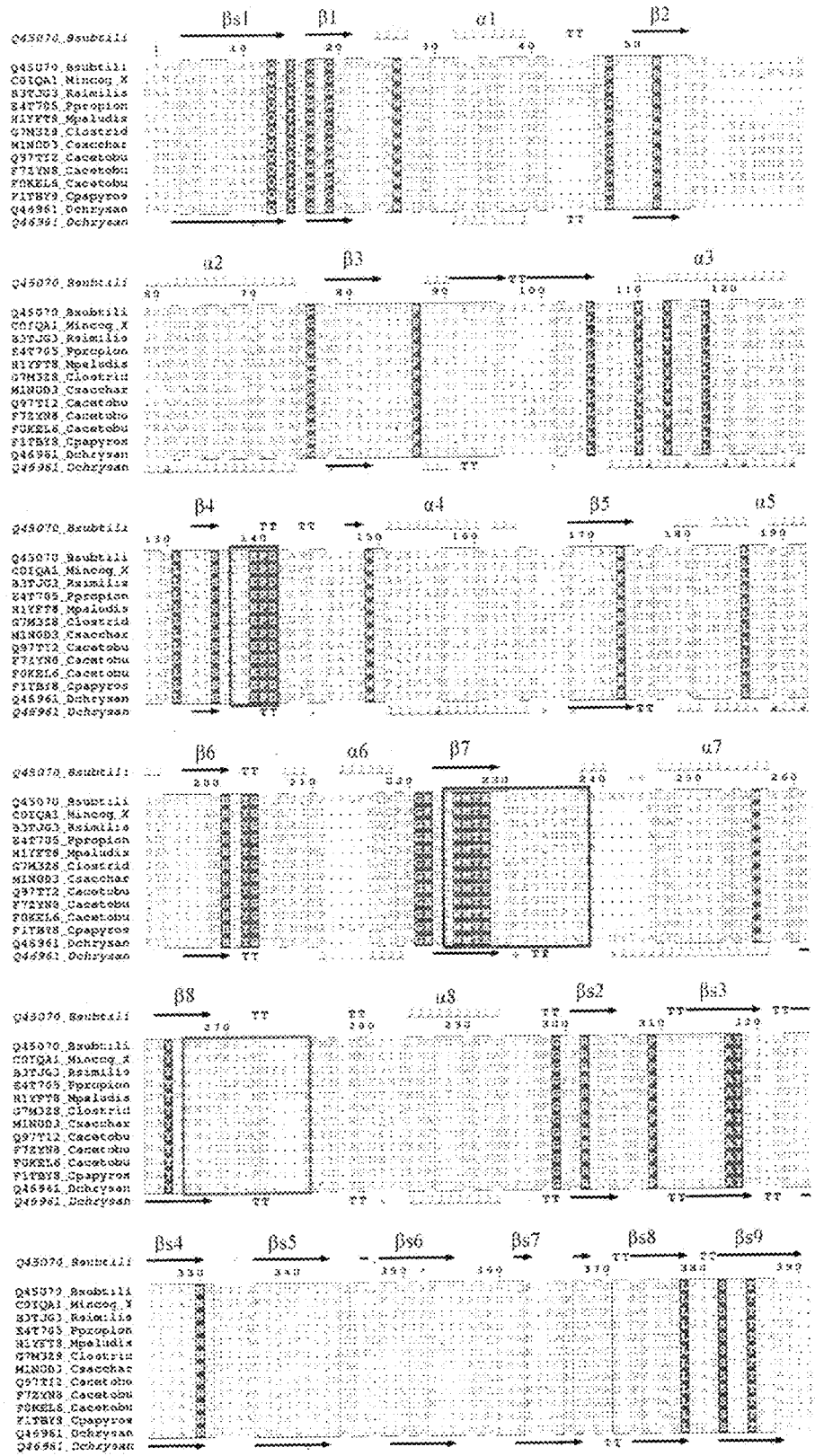
FIG. 5. An amino acid sequence alignment of the GA-independent GH30-8 subset of enzymes being disclosed including the canonical GA-dependent enzymes XynC from *Bacillus subtilis* and XynA from *Erwinia chrysanthemi* for comparison revealing how these enzymes show high levels of sequence identity not different than that shown in FIG. 4, yet the β7-α7 and β8-α8 loop regions are conserved. The sequence labeled Q45070 in FIG. 5 is residues 2-389 of SEQ ID NO:5, which ends with amino acids of asparagine (Asn or N) and arginine (Arg or R); the sequence labeled C0IQA1 is SEQ ID NO:32; the sequence labeled B3TJG3 is SEQ ID NO:33; the sequence labeled E4T705 is SEQ ID NO:3, beginning at residue 45; the sequence labeled H1YFT8 is SEQ ID NO:4, beginning at residue 33; the sequence labeled G7M3Z8 is SEQ ID NO:34; the sequence labeled M1N0D3 is SEQ ID NO:35; the sequence labeled Q97TI2 is SEQ ID NO:1, residues 33 to 420; the sequence labeled F7ZYN8 is SEQ ID NO:36; the sequence labeled F0KEL6 is SEQ ID NO:37; the sequence labeled F1TBY8 is SEQ ID NO:2, residues 34 to 421; the sequence labeled Q46961 is SEQ ID NO:31, which ends with a lysine (Lys or K).

Specifically, the GH30-8 GA-independent xylanases of the present invention comprise any protein which, through primary sequence analysis, contains a confidently classified GH30-8 catalytic module with family conserved catalytic amino acids identified, as a part, or whole of a mature amino acid sequence, but having an altered sequence in place of the functionally characterized, GH30-8 subfamily conserved β7-α7 and β8-α8 loops of interest, as found in the XynQ97 (CaXyn30A), XynC7I (CpXyn30A), PpXyn30A and MpXyn30A xylanases and described further herein. In one embodiment, the specific amino acid sequence in the Pβ7-α7 and β8-α8 loops is as shown in SEQ ID NO: 1 (FIG. 5, Label: Q97TI2_Cacetobu & FIG. 14). The invention also includes those confidently classified GH30-8 (as described above) xylanases comprising at least 30% identity, at least 40% identity, at least 50% identity, at least 60% identity, at least 70% identity, at least 80% identity, at least 90% identity, at least 95% identity, or at least 98% identity to the specific amino acid sequence in the β7-α7 and β8-α8 loop regions of one or more of SEQ ID NO:1, SEQ ID NO:2 (C7I), SEQ ID NO:3 (PpXyn30A) or SEQ ID NO:4 (MpXyn30A).

Figure 4:
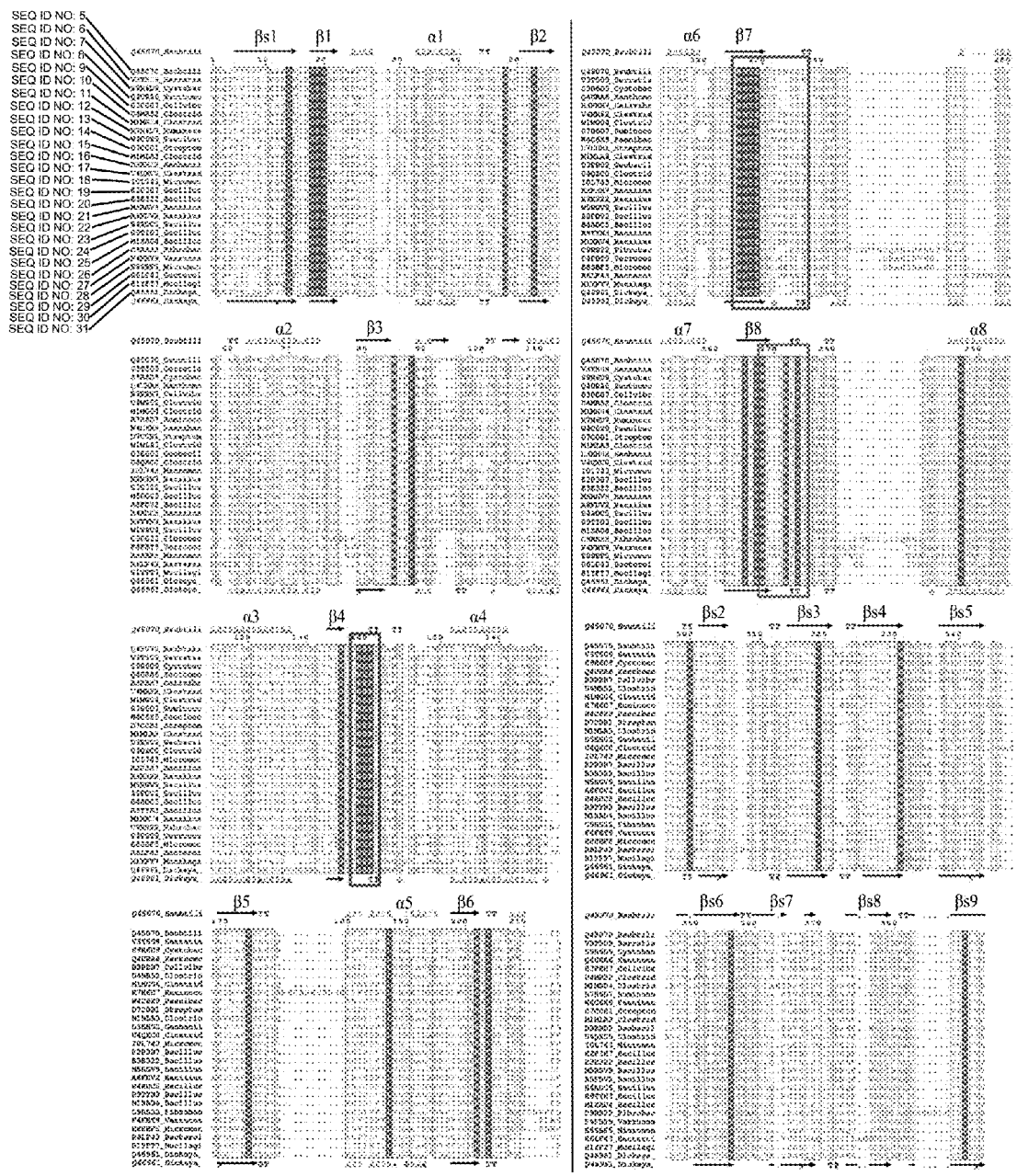
FIG. 4. An amino acid alignment of diverse GA-dependent GH30-8 xylanase amino acid sequences with similarity to XynC from *Bacillus subtilis* and XynA from *Erwinia chrysanthemi* and showing the canonical conserved regions between these enzymes which includes the β7-α7 and β8-α8 loop regions. The sequence labeled Q45070 is SEQ ID NO:5; the sequence labeled V3T509 is SEQ ID NO:6; the sequence labeled S9R6D6 is SEQ ID NO:7; the sequence labeled Q4URA6 is SEQ ID NO:8; the sequence labeled B3PEH7 is SEQ ID NO:9; the sequence labeled U4MR52 is SEQ ID NO:10; the sequence labeled M1MG04 is SEQ ID NO: 11; the sequence labeled R7H6D7 is SEQ ID NO:12; the sequence labeled W4C6X9 is SEQ ID NO:13; the sequence labeled D7C0B1 is SEQ ID NO:14; the sequence labeled M1MLA3 is SEQ ID NO:15; the sequence labeled D3EH02 is SEQ ID NO:16; the sequence labeled U4QXC0 is SEQ ID NO:17; the sequence labeled IOL743 is SEQ ID NO:18; the sequence labeled K2P3H7 is SEQ ID NO:19; the sequence labeled E3E322 is SEQ ID NO:20; the sequence labeled M5RGV9 is SEQ ID NO:21; the sequence labeled A8FDV2 is SEQ ID NO:22; the sequence labeled B4ADC5 is SEQ ID NO:23; the sequence labeled R9TYN3 is SEQ ID NO:24; the sequence labeled M1XAU4 is SEQ ID NO:25; the sequence labeled C9RS22 is SEQ ID NO:26; the sequence labeled F4FBT9 is SEQ ID NO:27; the sequence labeled E8SBF5 is SEQ ID NO:28; the sequence labeled R6LF43 is SEQ ID NO:29; the sequence labeled H1YFT7 is SEQ ID NO:30; the sequence labeled Q46961 is SEQ ID NO:31.

While the GA-independent GH30-8 xylanases are different in the Jβ7-α7 and β8-α8 loop regions relative to the conserved sequence of these loops in the GA-dependent GH30-8 xylanases, these sequences are also notably diverse within this GH30-8 subset of xylanases (FIGS. 5, 12 and 13), highlighting a likelihood that they may all function uniquely. The function of GA-dependent xylanases appears primarily attributable to the conserved β8-α8 loop sequence WW(YF)(IGL)(RK)R(SQYFC)Y(GS) (RR-motif) (as ascertained from the diverse alignment provided in FIG. 4). In the GH30-8 GA-independent xylanases the conserved RR-motif sequence in this loop is replaced with the sequence (WY)(WF)W(IVF)(not R)(not R) (SEQ ID NOs: 69-80), as ascertained from the GA-independent GH30-8 alignment provided in FIG. 5). Accordingly, the invention encompasses GA-independent GH30-8 xylanases or variants thereof comprising the β8-α8 loop sequence (WY) (WF)W(IVF)(not R)(not R) (SEQ ID NOs:69-80).

Figure 20:
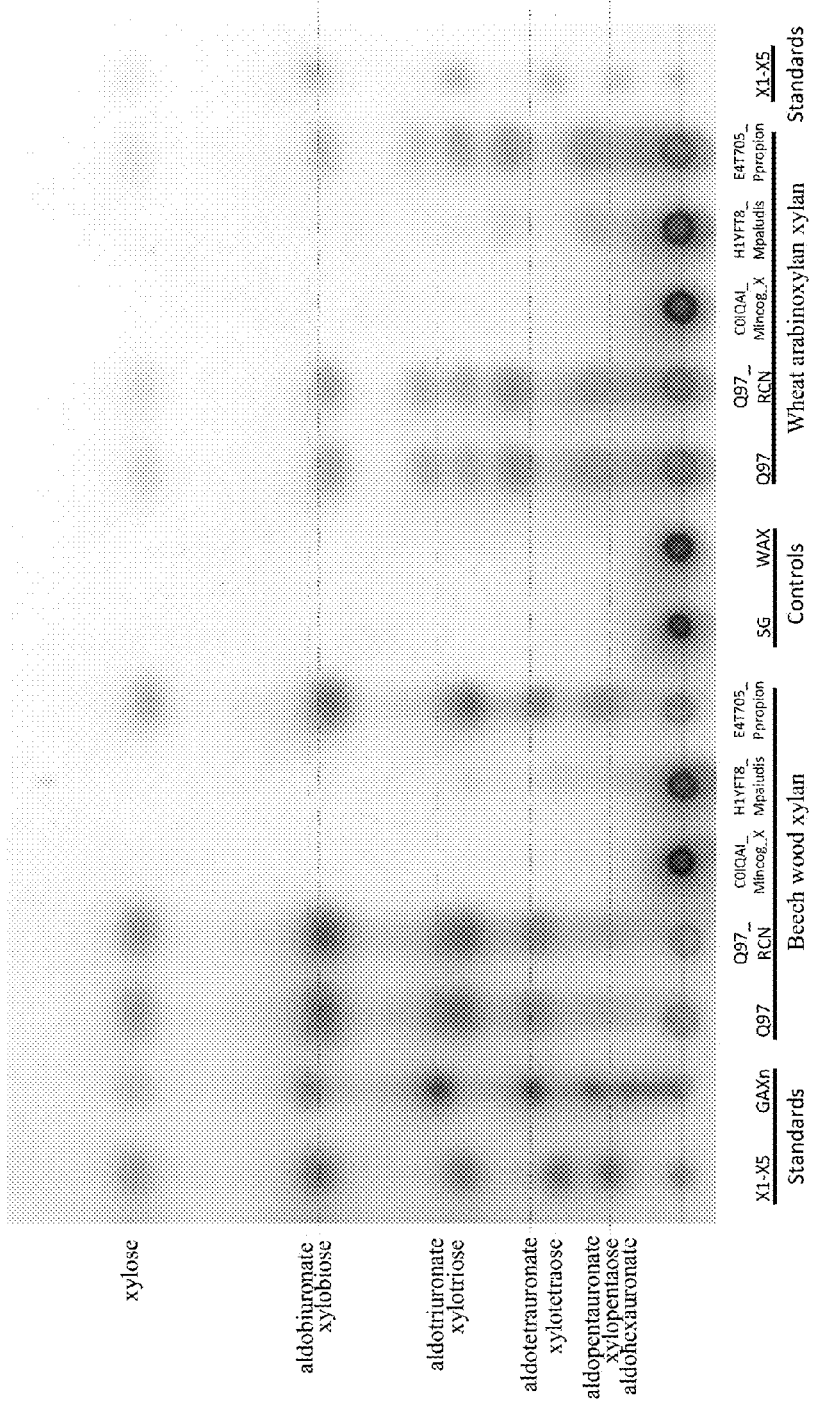
FIG. 20. TLC analysis of additional GA-independent GH30-8 xylanases and the full CaXyn30A (Q97_RCN) xylanase containing the natively encoded C-terminal CBM13 module along with the originally studied Q97 catalytic domain.

Indeed, the CpXyn30A (C7I) xylanase performed very similar to the CaXyn30A (Q97) with respect to the final hydrolysis products detected by TCL, but the measured rate of hydrolysis was notably low. It is not clear from our current level of analysis whether the CpXyn30A yielded a portion of larger oligosaccharides as observed in the TLC (FIG. 6) for both beech wood xylan and wheat arabinoxylan because of this comparably low activity, or because of the unique sequence differences between the β7-α7 and β8-α8 loop regions of these two GA-independent GH30-8 xylanases. Likewise, the PpXyn30A enzyme with yet a different sequence representing its β7-α7 and β8-α8 loops produced very similar results to both CpXyn30A and CaXyn30A (FIG. 20). However, the MpXyn30A enzyme, while clearly functioning as an endoxylanase yielding larger neutral xylooligosaccharides such as xylotriose and xylotetraose failed to result in any significant hydrolysis (barely detectable) yet is still shown to be GA-independent (FIG. 20).

Figure 10A:
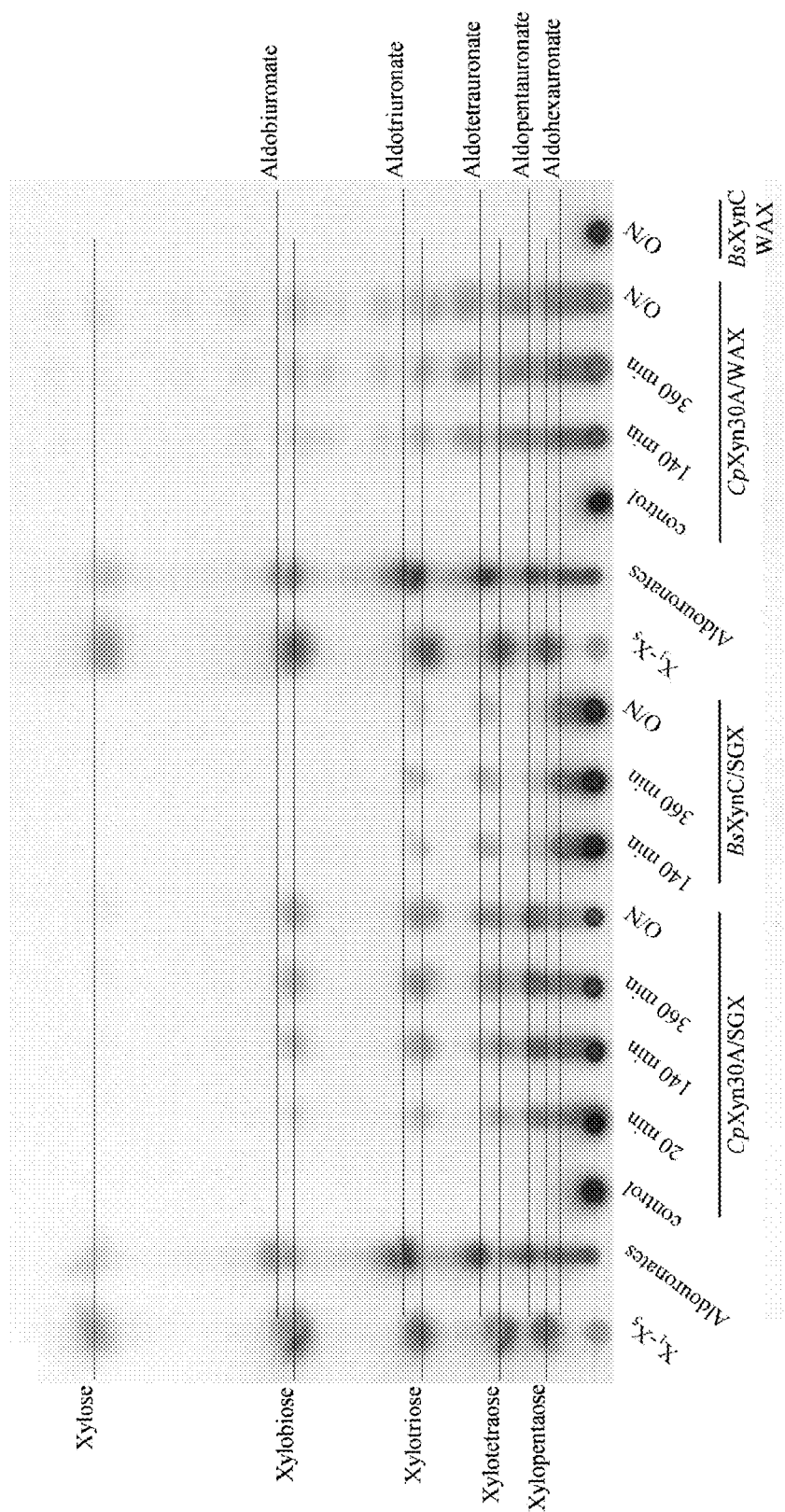
FIG. 10A. Thin layer chromatography analysis of hydrolysis products of glucuronoxylan (SGX) and arabinoxylan (WAX) by CpXyn30A compared with XynC from *Bacillus subtilis*.
Figure 10B:
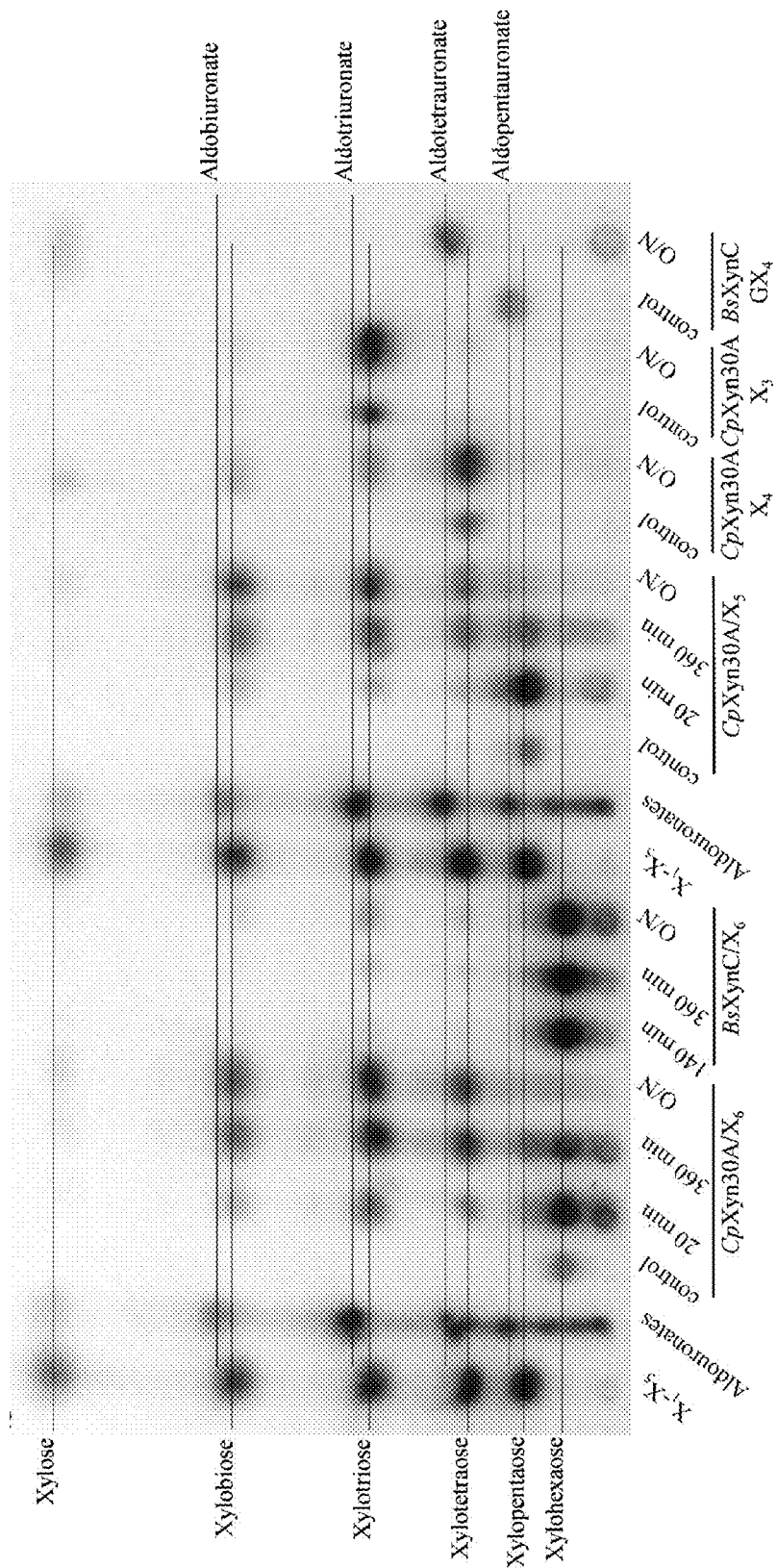
FIG. 10B. Thin layer chromatography analysis of hydrolysis products of xylooligosaccharides by CpXyn30A compared to XynC from *Bacillus subtilis*.

The GA-independent GH30-8 xylanases of the present invention hydrolyze GX to provide a series of small neutral xylooligosaccharides and aldouronates (FIGS. 6, 10A, 10B and 20), which is very different from the aldouronate ladder produced by the GA-dependent GH30-8 xylanases (FIGS. 6, 10A and 10B). Additionally the GX hydrolysis product profile for the GA-independent GH30-8 xylanases of the present invention are more similar, but unique to GX hydrolysis product profiles generated by the common GH10 and GH11 endo-β-1,4-xylanases. None of the GA-independent GH30-8 xylanases result in xylose as a primary hydrolysis product as observed for some GH10 xylanases. Also, unlike the GH10 and GH11 xylanases which produce, as their primary aldouronate limit product of GX hydrolysis, the tetrameric product aldotetrauronate and aldopentauronate, respectively, the GA-independent GH30-8 enzymes are potentially able to liberate aldotriuronate as the smallest limit product (FIGS. 21A-B).

Since hydrolysis of arabinoxylan by GA-dependent GH30-8 xylanases does not occur (FIG. 6), the hydrolysis product profile obtained with the GA-independent GH30-8 xylanases on this substrate is very unique. Further, these enzymes appear to be very efficient at the liberation of difficult to reduce (hydrolyze) arabinoxylan substrates, relative to GH10 xylanases (FIG. 6). For this substrate, the tested GA-independent GH30-8 xylanases produce unique hydrolysis product profiles.

Figure 21A:
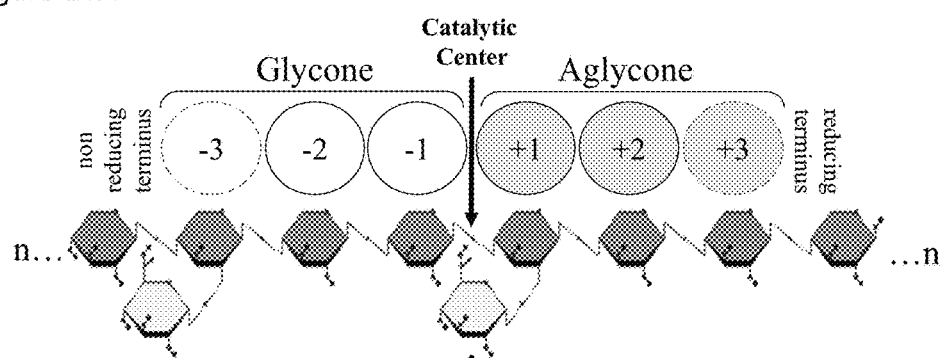
FIG. 21A. Schematic representing the xylosyl binding subsites of an endo-xylanase active site detailing the locations along the xylan chain where the enzyme may accommodate or require (as in the GA-dependent GH30-8 xylanases) a GA substitution. Example of GX within the active site of a GH10 xylanase showing GA accommodating xylose subsites and therefore a deduced limit product of aldotetrauronate.
Figure 21B:
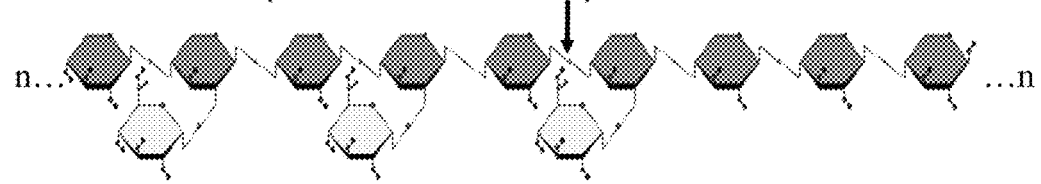
FIG. 21B. Example of GX within the active site of a GH30-8 GA independent xylanase showing GA accommodating xylose subsites and therefore a deduced limit product of aldotriuronate.

Rationalization and our results support the likelihood that the GA-independent GH30-8 xylanases are better at liberating small substituted xylooligosaccharides and substituted xylooligosaccharides from highly substituted regions of xylans (FIGS. 21A-B). The current state-of-the-art is that GH10 xylanases produce the smallest hydrolysis products. The primary limit product of these xylanases is aldotetrauronate. This is because, as detailed in FIG. 21A the enzyme can accommodate the O-2 substituted GA moiety only in the +1 and −3 subsites within the substrate binding cleft. In comparison to these GH10 xylanases and, as detailed in FIG. 21B, for GA-dependent GH30-8 xylanases the −2 subsite is responsible for the coordination of a GA substituted xylose. Without this, hydrolysis is known not to occur. In these enzymes, although the GA is specifically "bound" in this position, the general observation is that the GA moiety is extended upward out of the catalytic cleft and therefore not into the enzyme where steric interaction might prevent hydrolysis. Notably, based on limit product studies of GX by these GA-dependent GH30-8 xylanases, the smallest aldouronate that might be produced (depending upon the nature of the specific GX being analyzed) is aldotriuronate. This would indicate that in these xylanases, a GA substitution can also be accommodated on the xylose in the +1 subsite (see FIGS. 21A-B). Based on xylan chain bonding and the reported position within xylan binding enzymes, it appears very likely that the xylose in this subsite would present the O-2 hydroxyl upward out of the substrate binding cleft. A GA substituted in this position would likely therefore be accommodated.

Extending this rationale to the GA-independent GH30-8 xylanases of the present invention, it would than seem possible that, barring changes to the +1 subsite region, both the +1 and −2 subsites may accommodate substituted GA moieties. This is verified with the CaXyn30A (Q97) xylanase-(FIG. 6), as the sugar aldotriuronate is clearly visible following a limit digestion. The extended range of function of these enzymes is also likely to benefit hydrolysis of the more highly substituted (with arbinofuranose) wheat arabinoxylan substrate. This is confirmed by results in the hydrolysis of this substrate (FIG. 6), where compared to the GH10 xylanase CaXyn30A, it effectively converted the entire starting amount of xylan to xylooligosaccharides and substituted xylooligosaccharides.

In one embodiment, the GA-independent, GH30-8 xylanases of the present invention represent eight (upon last count) nonredundent sequences out of several hundred in the UniProt protein database which through primary sequence analysis are confidently classified as GH30-8 xylanases. However, in each of these the sequence of the β7-α7 and β8-α8 loop regions is completely different than the canonical sequence found in the GA-dependent GH30-8 xylanases and also unique within the disclosed subset as described above. These enzymes are shown to have a loss of GX substrate specificity and expanded function, providing unique xylan hydrolysis product profiles relative to the GA-dependent GH30-8 xylanases and xylanases from other xylanase enzyme families and also are proposed to be more efficient in the hydrolysis of highly substituted polymeric xylan for reasons presented throughout.

In one embodiment, by "GA-independent GH30-8 xylanases" we mean the isolated enzymes having xylanase activity comprising amino acid sequences from *Clostridium* (UniProt accession numbers G7M3Z8, MINOD3, Q97TI2 {Q97}, F7ZYN8 and FOKEL6); the southern root knot nematode *Meloidogyne incognita* (UniProt accession numbers COIQA1 and COIQA2); the plant pathogenic nematode *Radopholus simitis* (UniProt accession number B3TJG3); the bacterium *Paludibacter propionicigenes* (UniProt accession number E4T705); the bacterium *Mucilaginibacter paludis* (UniProt accession number H1YFT8); and from *Clostridium papyrosolvens* (UniProt accession number F1TBY8 {C7I}).

In one embodiment, the GH30-8 enzymes are CpXyn30A (also referred to throughout as C7I, XynC7I and CpXynC7I) and CpXynQ97 (also referred to throughout as Q97 and XynQ97 and CaXynQ97).

By "isolated enzyme" we mean polypeptides isolated from other cellular proteins, purified and recombinant polypeptides, cellular material, viral material, chemical precursors or other chemicals.

TABLE 1

Comparison of amino acid identity levels of the GH30-8 GA-independent xylanases of the present invention to the characterized GH30-8 GA-dependent xylanases BcXynC and EcXynA.

| | Level of Identity to the Canonical GH30-8 Xylanases (%)[1] | | |
|---|---|---|---|
| | XynC (UniProt: 45070) | XynA (UniProt: Q46961) | XynQ97 (UniProt: Q97TI2)[2] |
| Q45070_Bsubtilis (BsXynC) | 100 | 40.4 | 40.9 |
| C0IQA1_Mincognita | 34.3 | 34.6 | 38.9 |
| B3TJG3_Rsimilis | 38.8 | 45.0 | 47.2 |
| E4T705_Ppropionicigenes (PpXyn30A)[2] | 37.5 | 41.6 | 42.1 |
| H1YFT8_Mpaludis (MpXyn30A)[2] | 38.2 | 35.4 | 39.7 |
| G7M3Z8_Clostridium sp. | 43.6 | 43.5 | 65.6 |
| M1N0D3_Csaccharoperbu-tylacetonicum | 40.1 | 43.5 | 68.5 |
| Q97T12_Cacetobutylicum (CaXynQ97)[2,3] | 40.9 | 40.4 | 100 |
| F1TBY8_Cpapyrosolvens (CpXynC7I)[2] | 54.5 | 36.1 | 49.6 |
| Q46961_Dehrysanthemi (EcXynA) | 40.9 | 100 | 40.4 |

[1]Comparative analysis was performed with the sequence shuffling tool PRSS available at http://fasta.bioch.virginia.edu/fasta_www2/fasta_www.cgi?rm=shuffle.
[2]XynQ97, XynC7I, PpXyn30A and MpXyn30A are the four GH30-8 subset xylanases being used to represent the disclosed GH30-8 xylanases of the present invention in this application and are included for comparative reasons.
[3]Sequnces with UniProt accession numbers F7ZYN8 and F0KEL6 are not included as they are 100% identical to UniProt accession number Q97TI2 and are therefore redundant.

Compositions Comprising the GH30-8 Xylanases of the Present Invention.

The present invention provides a composition comprising an effective amount of at least one GA-independent GH30-8 xylanase that is capable of breaking down lignocellulose material. The enzyme composition of the invention may comprise a multi-enzyme blend, comprising more than one enzymes or polypeptides of the present invention. The GH30-8 xylanase subset composition of the invention can suitably include one or more additional enzymes derived from other microorganisms, plants, or organisms. Synergistic enzyme combinations and related methods are contemplated. One skilled in the art can readily identify the optimum ratios of the GH30-8 enzymes to be included in the enzyme compositions for degrading various types of lignocellulosic materials to contribute to efficient conversion of various lignocellulosic substrates to their constituent fermentable sugars in the case of conversion of polymeric sugars to monomers and to the desired oligomeric xylooligosaccharide mixture if that is desired. Assays known to the art may be used to identify optimum proportions/relative weights of the GH30-8 xylanases in the enzyme compositions, with which various lignocellulosic materials are efficiently hydrolyzed or broken down in saccharification processes.

In one embodiment, the invention comprises a composition comprising an effective amount of at least one of the novel GA-independent GH30-8 xylanases of the present invention. By "effective amount" we mean an amount sufficient to catalyze or aid the digestion or conversion of hemicellulose materials in lignocellulosic polysaccharide containing substrates to fermentable sugars or to a desired xylooligosaccharide composition and or to obtain a desired quality in the remaining xylan containing materials providing the full or partial removal of xylan. In one embodiment, an "effective amount" comprises the amount required to convert polymeric xylan, under ideal conditions, to the limit xylooligosaccharides, with depletion of the polymer in a given period of time. In one example, the combined weight of the novel GH30-8 xylanase subset of the present invention having xylanase activity as measured by HPLC or biochemical reducing sugar assays can constitute about 0.05 wt. % to greater than 99 wt. % (e.g., about 0.05 wt. % to about 70 wt. %, about 0.1 wt. % to about 60 wt. %, about 1 wt. % to about 50 wt. %, about 10 wt. % to about 40 wt. %, about 20 wt. % to about 30 wt. %, about 2 wt. % to about 45 wt %, about 5 wt. % to about 40 wt. %, about 10 wt. % to about 35 wt. %, about 2 wt. % to about 30 wt. %, about 5 wt. % to about 25 wt. %, about 5 wt. % to about 10 wt. %, about 9 wt. % to about 15 wt. %, about 10 wt. % to about 20 wt. %, etc) of the total proteins in the enzyme composition.

In one embodiment, the enzyme compositions desirably comprise mixtures of 2 or more, 3 or more, 4 or more, or even 5 or more GH30-8 xylanases of the invention as defined above that can catalyze or aid the digestion or conversion of hemicellulose materials to a desired oligosaccharide mixture, their final xylooligosaccharide mixture or to fermentable sugars. It is expected that members of the GH30-8 subset, may function synergistically with xylanases of other enzyme families (including the GA-dependent GH30-8 xylanases), to more efficiently degrade xylan. Suitable xylanases include those having at least equal to or greater than 30% (e.g., at least about 30%, 35%, 40, 45%, 50%, 55%, 60%, 65%, 70%, 75%, 80%, 85%, 90%, 91%, 92%, 93%, 94%, 95%, 96%, 97%, 98%, or 99%) identity to SEQ ID NOs: 1-4, over a region of at least about 0.10 (e.g., at least about 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400) residues.

The GH30-8 xylanase composition of the present invention may also comprise an effective amount of at least one of the novel GH30-8 enzymes of the present invention and at least a second additional enzyme having enzymatic activity. For example, the composition may include enzymes having xylosidase activity, cellobiohydrolase activity, β-glucosidase activity, cellulase activity, β-xylosidase activity, arabinofuranosidase activity, lytic polysaccharide monooxygenase activity, lyase activity or endoglucanase activity.

The GH30-8 xylanase compositions of the present invention can suitably further comprise one or more accessory proteins, such as, for example and without limitation, mannanases such as endomannanases, exomannanases, and 6-mannosidases; galactanases such as endo- and exo-galactanases; arabinases such as endo-arabinases and exo-arabinases; ligninases; amylases; α-glucuronidases; proteases; esterases such as ferulic acid esterases, acetyl xylan esterases, coumaric acid esterases or pectin methyl esterases; lipases; other glycoside hydrolases; xyloglucanases; CIP1; CIP2; swollenins; expansins; and cellulose disrupting proteins such as cellulose binding modules; other xylanases, pectate lyases and arabinofuranosidases; stabilizers known to the art. Additives include, without limitation, any combination of sugars (e.g. maltose, glycerol), sugar alcohols (e.g. sorbitol), detergents (usually nonionic) or thickeners and cryoprotectants (e.g. glycerol, propylene glycol, polyethylene glycol).

The other enzymes or proteins of the composition of the current invention can be isolated or purified from a naturally-occurring source, or expressed or overexpressed by a recombinant host cell. They may be added to an enzyme composition in an isolated or purified form. They may be expressed or overexpressed by a host organism or host cell as part of a culture mixture, for example a fermentation broth.

The GH30-8 enzyme compositions of the present invention are used or are useful for producing metabolizable simple sugars in conjunction with other xylan accessory enzymes, such as α-glucuronidases, α-arabinofuranosidases, esterases and xylosidases. The GH30-8 subset xylanases of the present invention, by themselves will generate xylose only as a nonspecific low rate side reaction of an already small xylooligosaccharide. The xylooligomeric sugar mixture produced by these enzymes can best be viewed in the TLC data of the Q97, C7I, PpXyn30A and MpXyn30A proteins (FIGS. 6, 10A-B and 20).

The GH30-8 enzyme compositions of the present invention are also used or are useful for reducing hemicellulosic polymers and cellulosic polymers (when synergistically applied with cellulase enzymes or lignocellulose or cellulase disrupting proteins such as CBMs, expansins or swollenins or lytic polysaccharide monooxygenases) into metabolizable carbon moieties. The enzyme composition is suitably in the form of a product of manufacture, such as a formulation, and can take the physical form of a liquid or a solid.

Methods of Synthesis.

As described in the examples below, protein expression and purification scheme is done as known in the art. The cells are grown in preparation of protein expression and during protein expression and are optimized as necessary to increase protein yield. Such changes that might be considered for enhanced protein expression include: the specific treatment of the cells during the inoculant growth, the specific conditions of the inoculation such as the quantity of cells used, the starting amount of antibiotic selection, culture growth (and/or protein expression) temperature, the OD 600 nm measure when induction begins, whether IPTG or lactose is used to induce expression of the lac operator, The concentration of the inductant, oxygen availability during growth and more importantly during protein expression, and the length of time provided for expression. The current systems of expression are primarily based upon guidance provided by the pET System manual from Novagen (10$^{th}$ Edition) for use with IPTG/lactose inducible lac operators in the Gram-negative bacterium *Escherichia coli*. The protein coding region for these GH30-8 GA-independent xylanases of the present invention might also be expressed from any number of other inducible expression vectors or even nun-inducible, leaky vectors. Other vectors include expression that is inducible with other sugars such as arabinose, mannose or other chemicals or those that are responsive to physical changes such as exposure to any wavelength of light, temperature change or chemical shock.

Using any of the protein expression systems described above, the methods employed for protein expression could also be altered to perform as an autoinduction system. Yields of these enzymes might also increase through the use of other protein expression hosts such as, but not limited to other bacteria, yeast, fungi, plants and insects. Although not expected to increased yields, these enzymes might also be produced through in-vitro synthesis or through purification of the desired enzyme from the native source organism.

METHODS OF USE

The GH30-8 xylanases and compositions of the present invention can be applied in any industry for the reduction of xylans to xylooligosaccharides and novel mixtures of substituted xylooligosaccharides or for the production of desired product characteristics resulting from the removal, partial removal, limited disruption or modification of xylan fraction. By "xylans" we mean a β-1,4-linked xylose polysaccharide which is the primary hemicellulose of hardwoods and crop residues and the second most abundant carbohydrate polymer in lignocellulosic biomass. Other forms of this hemicellulosic polysaccharide can also be found in grain derived food products and in fruit products. The source of the xylan polysaccharide typically defines its chemical characteristics in terms of chain length and sugar and non-sugar substitutions along the xylan chain. The nature of the substitutions along the xylan chain define various xylan types including, glucuronoxylan, acetylglucuronoxylan, acetylglucuronoarabinoxylan, glucuronoarabinoxylan and arabinoxylan, all generally referred to as "xylans".

The GH30-8 xylanase and compositions thereof of the present invention can be used for hydrolyzing, breaking up, or disrupting all xylans or xylan-comprising compositions. In one embodiment, the method comprises contacting the xylan or xylan-comprising composition with the GH30-8 GA-independent subset of xylanases or enzyme composition of the present invention under suitable conditions, wherein the GH30-8 subset or enzyme composition of the present invention hydrolyzes, breaks up or disrupts the xylan or xylan-comprising composition.

The GH30-8 xylanases of the present invention and compositions thereof used in such a process may comprise, for example, a 0.1 g to 100 g (e.g., 2 g to 20 g, 3 g to 7 g, 1 g to 5 g, or 2 g to 5 g) of polypeptides having xylanase activity per kg of hemicellulose in the biomass material. The GH30-8 xylanases of the present invention and compositions thereof may be applied in conjunction with other enzymes for complete enzymatic degradation of xylans to xylan-constituent monosaccharides or by itself to produce complex xylooligosaccharide mixtures or otherwise facilitate the processing of the xylan fraction of lignocellulosics.

The GH30-8 xylanase and compositions of the present invention can also be used to digest xylans from any source, including all biological sources, such as plant biomasses, including, but not limited to, corn, grains, sugarcane, grasses (Indian grass, such as *Sorghastrum nutans*; or, switchgrass, e.g., *Panicum* species, such as *Panicum virgatum*), perennial canes (e.g., giant weeds), woods or wood processing byproducts, e.g., in the wood processing, pulp and/or paper or nanocellulose and nanofibrilated cellulose industry, in textile manufacturing, in household and industrial cleaning agents, and in biomass waste processing; for the processing or preparation of dough or bread based products and in animal feed for application to enhance animal nutrition and feed digestion and possibly for the synthesis of larger xylooligosaccharides as exemplified in Example 1.

The GH30-8 xylanases of the present invention and compositions thereof (including enzymes or designed enzyme compositions) can also comprise at least one biomass material. By "biomass material" we mean any material comprising a lignocellulosic material derived from an agricultural crop or byproduct of a food or feed production. Suitable biomass material can also include lignocellulosic waste products, waste paper or waste paper products, plant residues comprising grains, seeds, stems, leaves, hulls, husks, corncobs, corn stover, grasses, straw, reeds, wood, wood chips, wood pulp, or sawdust. Exemplary grasses include, without limitation, Indian grass or switchgrass. Exemplary reeds include, without limitation, certain perennial canes such as giant reeds. Exemplary paper waste include, without limitation, discarded or used photocopy paper, computer printer paper, notebook paper, notepad paper, typewriter paper, newspapers, magazines, cardboard and paper-based packaging materials.

The GH30-8 xylanase of the present invention and compositions thereof (including enzymes or designed enzyme compositions, such as products of manufacture or a formula) are useful for hydrolyzing hemicellulosic materials, catalyzing the enzymatic conversion of suitable biomass substrates to mixtures of complex oligomeric sugars or fermentable simple sugars.

Methods of using or applying the GH30-8 xylanases and compositions thereof in a research setting, an industrial setting, or in a commercial setting are also provided. The GH30-8 xylanases of the present invention and compositions thereof may be added as a desired mass of dry powder or as a desired volume of concentrated or diluted aqueous or non-aqueous solution to xylan containing materials incubated at a desired temperature, which may include temperatures which are optimal or not optimal (could be too hot (slow or fast inactivation through denaturation) or too cold (non-optimal activity)) for the GH30-8 xylanases of the present invention. The application of the GH30-8 xylanases of the present invention and compositions thereof may continue until such time as the desired outcome is achieved. For application as an additive to animal feed, the designated amount of GH30-8 xylanases of the present invention or compositions thereof will be added to, at the desired proportion, a xylan containing biomass material or to a non-xylan containing material intended for animal consumption. Following addition, this animal feed material will be processed in a manner consistent with significant or acceptable GA-independent GH30-8 xylanase activity recovery for the anticipated application within the animals digestive tract.

It is also considered that these GH30-8 xylanases of the present invention and compositions thereof may be applied through surface treatments of biomass products and items for the alteration of wood surface physical, chemical or textural properties. Using the GH30-8 xylanases and compositions of the present invention to remove or reduce xylans in biomass preferably yields 50% to 90% xylobiose and an array of xylooligosaccharides of the enzyme accessible xylan.

In addition to reducing xylans in biomass to xylooligosaccharides and sugars, the GH30-8 xylanases and compositions of the present invention can be used in industrial, agricultural, human food and animal feed, as well as a human food and animal feed supplementation. There is an ever increasing interest for the use of lignocellulosic biomass to make products and fuels to increase our use of renewable resources, and for reduction of greenhouse gas emissions. The GH30-8 xylanases and compositions of the present invention may find applications in any lignocellulose based process in which the xylan component is treated for removal, or for subsequent use in the form of xylooligosaccharides, substituted xylooligosaccharides, oligosaccharides of other polymeric sugars or monosaccharides of any lignocellulose derived sugar. For instance, the GH30-8 xylanases and compositions of the present invention may find applications in wood, paper and pulp treatments, treating fibers and textiles, treating foods and food processing, animal feed supplementation and food or feed or food additives, reducing the mass and volume of substantially untreated solid waste, detergent, disinfectant or cleanser (cleaning or cleansing) compositions. There is also interest for use of such enzymes in processing of dough and in the preparation of other foods and beverages and in the preparation of prebiotics from both cereal grains and lignocellulosic biomass as food additives and nutraceuticals.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed description of the novel compounds and methods of the present invention are to be regarded as illustrative in nature and not restrictive.

III. Examples

The invention will be more fully understood upon consideration of the following non-limiting Examples. The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

Example 1. Structural and Biochemical Characterization CpXyn30A

In this example, we present the structural and biochemical characterization of a novel enzyme that possesses a high degree of amino acid identity to the canonical GH30-8 enzymes, but lacks the hallmark β8-α8 loop region which defines the GH30-8 subfamily of xylanases. The three-dimensional structure of this unique GH30 subfamily 8 homolog was determined using x-ray crystallographic methods and provide functional characterization of the enzyme with comparisons to the canonical GH30 subfamily enzyme XynC from *Bacillus subtilis* (BsXynC).

In light of the role of the β8-α8 loop region in imparting functional specificity to the GH30-8 subfamily, amino acid sequence studies were implemented to identify homologs which possess sequence differences in this region. A putative xylanase (UniProt ID: F1TBY8; referred to as xylanase 30A) derived from the lignocellulose degrading bacterium *Clostridium papyrosolvens* (CpXyn30A) was identified and chosen for study.

DNA Synthesis and Protein Expression.

The sequence for UniProt ID: C7MC9 (also known as F1TBY8) was identified for this study and the expression-optimized coding sequence (Welch et al., 2009) including an C-terminal HisTag was ordered from DNA 2.0 (Menlo Park, Calif.) in the kanamycin-resistant pJexpress 411 expression vector. Plasmid DNA was used to transform *Escherichia coli* for expression. Cells were grown with shaking at 37° C. in Luria-Bertani broth supplemented with 0.03 mg/mL kanamycin until they reached an optical density at 600 nm of 0.6. The cells were induced by the addition of isopropyl-β-D-thiogalactopyranoside to a final concentration of 0.5 mM and incubated with shaking at 250 RPM for five hours at 37° C. Cells were harvested by centrifugation at 7500 RPM for 20 minutes at 4° C. The resulting pellet was suspended in 50 mM sodium phosphate, 100 mM NaCl, pH 7.2 at a ratio of 5 mL per gram of cell pellet. A 1 µL aliquot of 1× Halt protease inhibitor (Thermo Fisher, Rockford, Ill. USA) was added for every 1 mL of buffer used. Suspended cells were lysed using sonication and the lysate was centrifuged at 11,000 RPM for 30 minutes at 4° C. The resulting supernatant was dialyzed overnight at 4° C. against 50 mM sodium phosphate, 500 mM NaCl, 10 mM imidazole, pH 7.2, using 10,000 Da MWCO dialysis tubing.

Purification.

The post dialysis material was centrifuged to remove any precipitate and then filtered through a 0.22 m filter to further remove debris. The filtered solution was then loaded onto a 1 mL HisTrap fast flow column (GE Healthcare Life Sciences Pittsburgh, Pa.) charged with $Ni^{2+}$ and the hexahistidine-tagged recombinant protein was eluted with a linear gradient of 0-500 mM imidazole in 50 mM sodium phosphate, 250 mM NaCl, pH 7.2. Peak fractions were analyzed by SDS-PAGE (Laemmli, 1970). Fractions containing the protein were combined and dialyzed against 50 mM sodium phosphate, 250 mM NaCl, 10 mM imidazole, pH 7.2, overnight at 4° C. using 10,000 Da MWCO dialysis tubing. A second purification step using a 1 mL HisTrap column charged with $Co^{2+}$ was then employed with the same elution scheme as above. A single large peak was obtained from this run and peak fractions were analyzed by SDS-PAGE to ascertain purity and size. Fractions containing the purified protein were combined and dialyzed into 20 mM HEPES, 150 mM NaCl, pH 7.2. In a separate preparation meant solely for biochemical studies, CpXyn30A was purified as described, but the final purified protein was dialyzed against 30 mM Tris HCl, 50 mM NaCl, pH 7.5. After dialysis, the protein solution was concentrated to at least 5 mg/mL and stored at −80° C. until crystallization or functional studies. The GH30-8 xylanase, BsXynC, was purified as previously described (St. John et al., 2011; St. John et al., 2006). Protein concentration was routinely determined using absorbance at 280 nm with the ProtParam predicted extinction coefficient (Gasteiger et al., 2005).

Crystallization.

The sparse matrix screens Crystal Screen, Crystal Screen 2, Index and PEG/Ion as well as the Sodium Malonate, and Ammonium Sulfate Grid Screens (Hampton Research, Aliso Viejo, Calif.) were used for the initial screening. Sitting-drop vapor-diffusion experiments were performed in 24 well microplates (Art Robbins Instruments, Sunnyvale, Calif.). Each well contained 300 μL of precipitant solution and drops were set using 1 μL of protein solution and 1 μL of precipitant. The plates were sealed with sealing film and incubated at 25° C. A crystallization condition of 0.1 M ammonium acetate, 0.1M Bis-Tris pH 5.5 and 17% polyethylene glycol 10,000 was found using the Hampton Research Index screen. Sitting-drop vapor-diffusion experiments were performed using this condition at protein concentrations of 6.5 mg/mL and 10 mg/mL and cubic crystals (0.5 mm on edge) were obtained in the drops containing CpXyn30A at a concentration of 6.5 mg/mL. Crystals were harvested for cryocrystallographic data collection by transferring them stepwise to solutions containing 5% (v/v), 10% (v/v) and 20% (v/v) glycerol in well solution. After the 20% glycerol transfer, the crystals were flash cooled and stored in liquid nitrogen until data collection.

Data Collection, Analysis and Model Building.

Data was collected on a Rigaku RU-H3R copper rotating anode generator, operating at 50 kV and 100 mA, fitted with Confocal Maxflux™ optics (Osmic Inc., Troy, Mich.) and a Rigaku R-Axis IV+ image plate detector. A 180° dataset was collected with 5 minute exposure times and a Phi oscillation of 0.5 degrees per image. The resulting data was processed to 2.01 Å and the crystal belonged to the orthorhombic space group, $C222_1$ with unit cell parameters: a=66.0, b=76.5, c=150.6 and a=β=γ=90.00. Data were indexed and integrated in iMosflm (Battye et al., 2011), scaled in SCALA (Evans, 2005), and initial molecular replacement phases, electron density map calculation and model building was performed with the programs Phaser (McCoy et al., 2007), Phenix (Adams et al., 2010) and Coot (Emsley et al., 2010), respectively. The final model (PDB code: 4FMV) was studied and figures prepared using PyMOL (DeLano, 2002).

Biochemicals and Assays.

All reagents were of the highest purity available. Xylooligosaccharides xylobiose (X2) and xylotriose (X3) were purchased from WAKO Chemicals (Richmond, Va.) and xylotetraose (X4), xylopentaose (X5) and xylohexaose (X6) were purchased from Megazyme International (Wicklow, Ireland). Concentrations of xylooligosaccharide standards were determined with the phenol-sulfuric total carbohydrate assay (Dubois et al., 1956). The aldouronate, aldopenturonate (GX4), with a GA residue substituted penultimate to the nonreducing terminus of xylotetraose was the aldouronate limit product of a GH11 xylanase (Biely et al, 1997) (*Trichoderma longibrachiatum*, XynII, Hampton Research, Aliso Viejo, Calif.) and was purified using a 1.7 m P-2 resin column (Bio-Rad, Hercules Calif.) in 50 mM formic acid. The Rotovap concentrated sugar was then loaded onto the same column equilibrated with water to remove the formic acid from the oligosaccharide. The desalted GX4 was lyophilized, dissolved in water and the concentration determined with the Blumenkrantz assay for total uronic acid content (Blumenkrantz & Asboe-Hansen, 1973).

Enzymatic Activity Measurements and Hydrolysis Product Studies.

Activity measurements on polymeric substrates were determined through reducing end quantification with the Nelson's Test (Nelson, 1944) as has been previously described (St. John et al., 2006). Conditions for hydrolysis by CpXyn30A were optimized using beech wood xylan (Sigma-Aldrich Corporation St. Louis, Mo.) in acetate buffers ranging in pH from 3-6. Thermostability was analyzed using enzyme pre-incubations at a range of temperatures from 4°-50° C. followed by activity assessment at 30° C. Activity measurements for functional comparison were performed using sweet gum wood glucuronoxylan (SGX) (kindly provided by James F. Preston from the University of Florida) and wheat arabinoxylan (WAX) (Megazyme International). Hydrolysis of xylooligosaccharides was determined using an Agilent 1260 HPLC (Agilent Technologies, Santa Clara, Calif.) with resolution of neutral xylooligosaccharides performed using a Phenomenex RNO column (Phenomenex Torrance, Calif. USA) with water as eluent at 0.3 ml/min flow and 75° C. or a Shodex SH1821 (Showa Denko America, New York, N.Y.) in 0.05% $H_2SO_4$ running at 0.8 ml/min and 75° C. In both cases, the refractive index of the eluate was monitored throughout the separations.

Hydrolysis reactions were performed in 25 μL volumes under optimized conditions (100 mM sodium acetate, pH 4.5, at 30° C.) with xylooligosaccharides at 12.1 mM; a concentration (of X6) that approximated that of the polysaccharide used in the reactions employing polymeric xylan substrates. Reactions were stopped by boiling the samples in a water bath for 5 minutes. For studies evaluation p-nitrophenol (pNP) conjugated xylooligosaccharides (pNPXn, where n=the number of xylose units) samples were injected onto an Agilent 1260 HPLC (Agilent Technologies, Santa Clara, Calif.) equipped with a Zorbax C8 column (Agilent Technologies) and were eluted with a 0-90% acetonitrile gradient in water (Eneyskaya et al., 2003) and absorbance of the eluate was monitored at 302 nm. All HPLC analyses were performed in triplicate using 5 μL injections. Thin layer chromatography (TLC) was performed as described previously (St. John et al., 2006; Bounias, 1980).

Amino Acid Sequence Studies.

Sequences were aligned with the program MAFFT (Katoh & Toh, 2008) and the alignment figure was generated with ESPript (Gouet et al., 2003). Domain prediction was done using the online Conserved Domains program (Marchler-Bauer et al., 2011) and the domain representation was created using the program DOG 1.0 (Ren et al., 2009). Phylogenetic relationships were calculated and represented using the software MEGA 6.0 (Tamura et al., 2013).

Selection of CpXyn30A.

Primary amino acid sequence alignments (FIG. 7a) identified a unique GH30-8 enzyme that did not contain the normally conserved β8-α8 loop sequence. For this enzyme, (UniProt ID: F1TBY8) sequence studies verified the existence of the two conserved glutamate amino acid side chains which catalyze the double displacement reaction common to CAZy Clan A enzymes and identified a likely secretion signal sequence in addition to non-catalytic modules positioned C-terminal of the GH30-8 catalytic module. These include a family 6 carbohydrate binding module (CBM6) for binding soluble glucan and two dockerin domains presumably for interaction within a cellulosome assembly (FIG. 7b). Combined, these features suggest that this enzyme may have a role in the degradation of the xylan component of lignocellulosic biomass. Phylogenetic analysis of CpXyn30A verifies the most similar enzymes to be GH30-8 homologs from Gram positive organisms (FIG. 7c).

Based on these findings and an interest in characterizing a GH30-8 enzyme with a nonconserved amino acid sequence in the β8-α8 loop, the coding sequence for the gene was ordered from DNA 2.0 with the Signal-P (Petersen et al., 2011) predicted secretion signal sequence replaced by an amino-terminal methionine and a hexahistidine tag appended to the new carboxy-terminus defined by the end of a GH30-8 sequence alignment effectively truncating the protein sequence before the predicted (Bateman et al., 2004) CBM6 and dockerin domains.

Structure of CpXyn30A.

Refinement and model quality statistics for CpXyn30A structure model are presented in Table 2.

TABLE 2

Data collection and refinement statistics of *Clostridium papyrosolvens* Xyn30A.

| PDB code | 4FMV |
|---|---|
| Wavelength (Å) | 1.542 |
| Resolution range (Å) | 38.30-2.01 (2.08-2.01) |
| Space group | C2221 |
| Unit cell parameters a, b, c (Å) | 66.0, 76.5, 150.6 |
| Total reflections | 46801 (4031) |
| Unique reflections | 24506 (2121) |
| Redundancy | 1.9 (1.9) |
| Completeness (%) | 94.9 (85.7) |
| Mean I/sigmaI | 27.63 (12.32) |
| Wilson B-factor (Å$^2$) | 16.05 |
| R-merge | 0.020 (0.058) |
| R-meas | 0.028 |
| CC* | 1.00 (0.996) |
| R-work | 0.1642 (0.1534) |
| R-free | 0.2010 (0.2341) |
| CC(work) | 0.949 (0.955) |
| CC(free) | 0.928 (0.708) |
| Number of atoms | 3228 |
| Ligands | 0 |
| Waters | 212 |
| Protein residues | 386 |

TABLE 2-continued

Data collection and refinement statistics of *Clostridium papyrosolvens* Xyn30A.

| PDB code | 4FMV |
|---|---|
| RMS (bonds, Å) | 0.013 |
| RMS (angles, °) | 1.50 |
| Ramachandran favored (%) | 97 |
| Ramachandran outliers (%) | 0 |
| Clash score | 2.71 |
| Average B-factor (Å$^2$) | 15.20 |
| Solvent (%) | 18.10 |

Statistics for the highest-resolution shell are shown in parentheses.

Figure 8A:
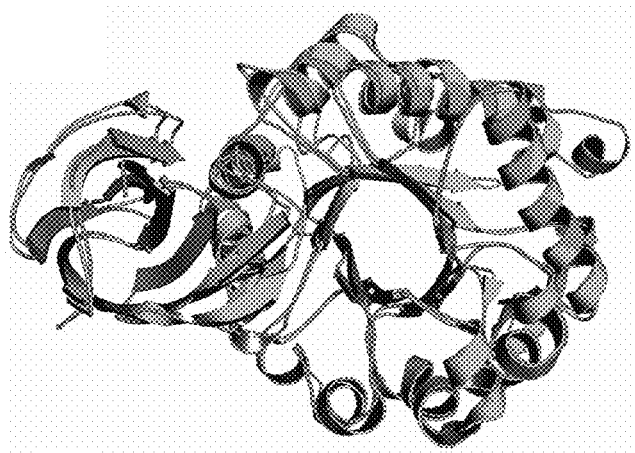
FIG. 8A. The crystal structure of CpXyn30A superposed on XynC of *Bacillus subtilis* establishing a structural relationship.
Figure 8B:
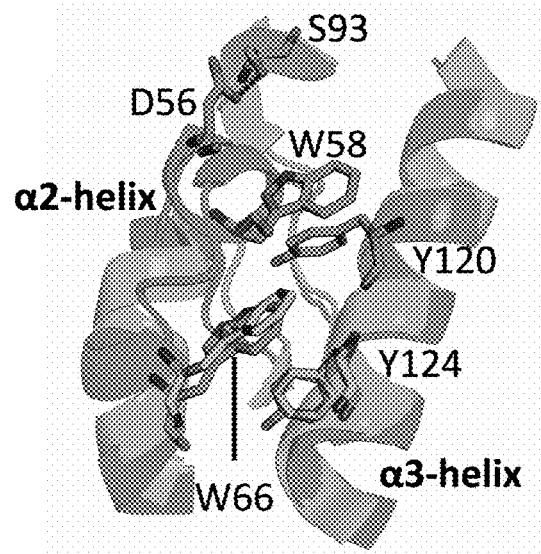
FIG. 8B. CpXyn30A superposed with XynC from *Bacillus subtilis* to compare structural differences in the α2 and α3 helix region.
Figure 8C:
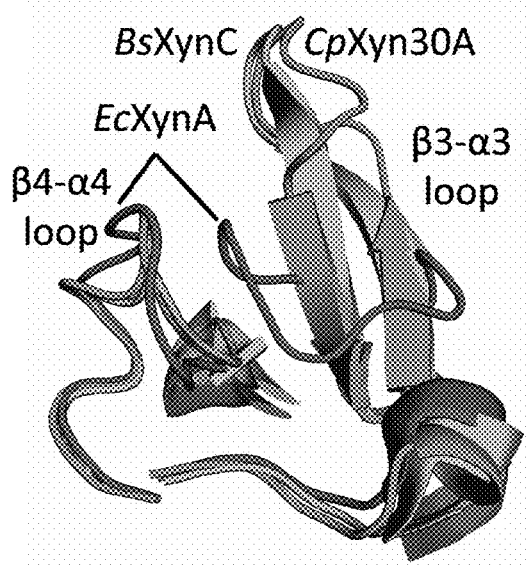
FIG. 8C. CpXyn30A superposed with XynC from *Bacillus subtilis* to compare the β3-α3 loop region which indicate that this notable structural portion is more similar to GH30-8 enzymes which derive from Gram-positive bacteria.
Figure 9A:
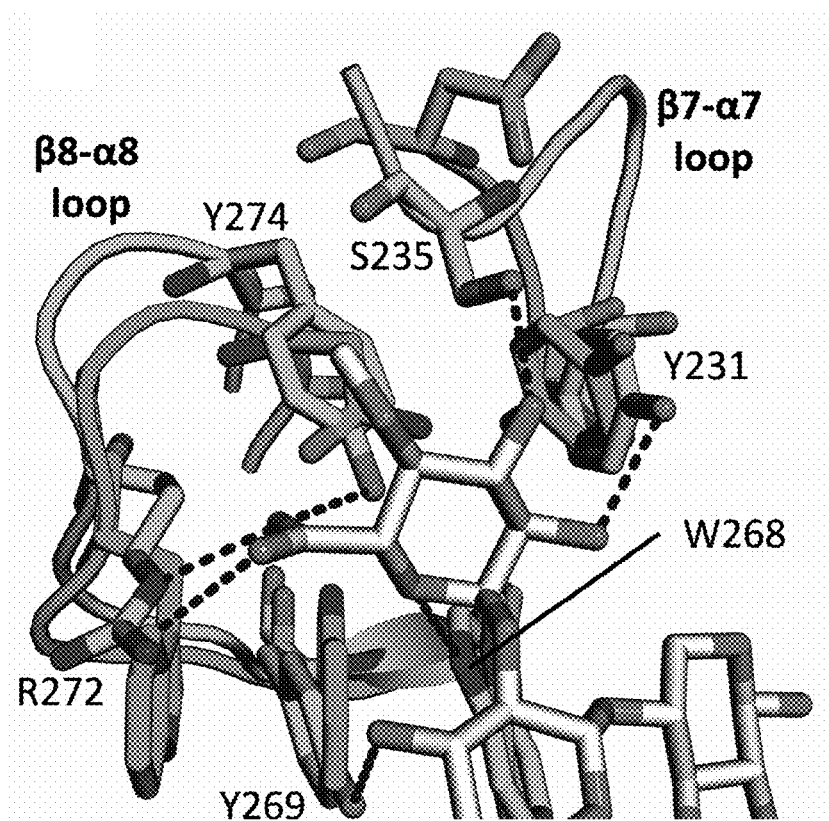
FIG. 9A. Ligand bound structural model of XynC from *Bacillus subtilis* superposed with the structure model of CpXyn30A showing how the substrate binding specificity is altered by the changes to the β7-α7 and β8-α8 loops.
Figure 9B:
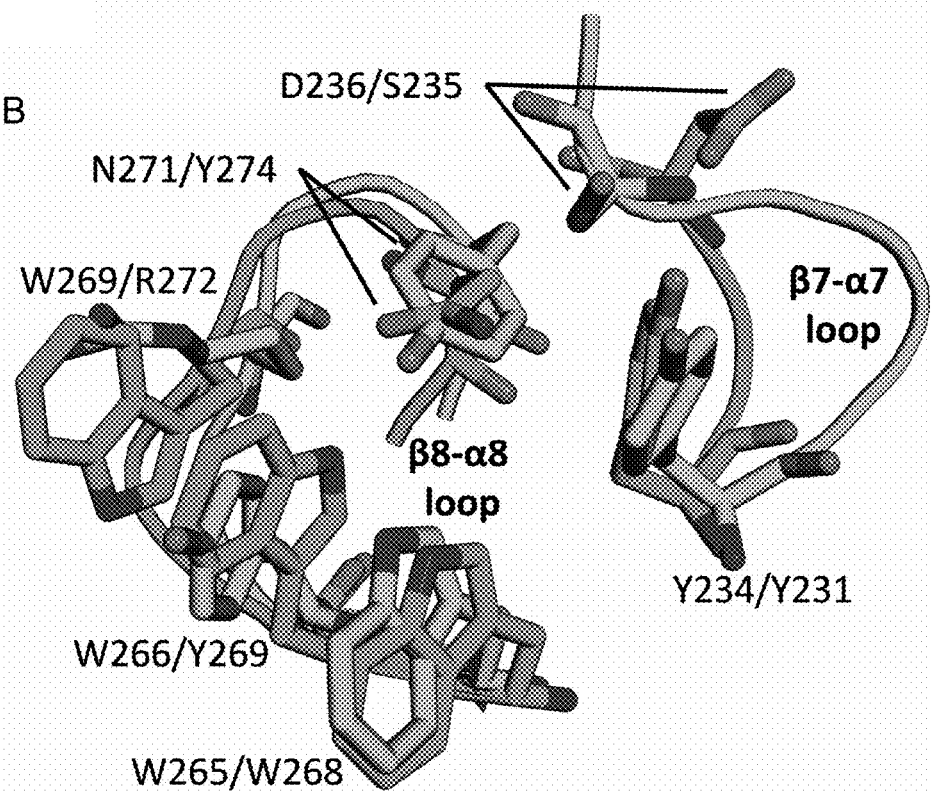
FIG. 9B. Superposition of CpXyn30A with XynC from *Bacillus subtilis* showing the amino acid side chains which are different resulting in a loss of specificity.

As expected, the overall structure of CpXyn30A is very similar to other GH30-8 enzymes with an RMSD of just 0.95 Å (all-atoms, Pymol: align) obtained when compared to the crystallographic structure of the canonical Gram-positive GH30 xylanase, BsXynC (FIG. 8a). However, the structure of CpXyn30A in the β8/α8 catalytic core domain is notably different from BsXynC (PDB code: 3KL5) in the β1-α1, β2-α2 (FIGS. 8b & 8c), and, most importantly in the CpXyn30A unique β7-α7 and β8-α8 loop regions (FIGS. 9a & 9b).

In the β1-α1 loop region, the sequence of CpXyn30A is shorter by three amino acids compared to BsXynC and the Gram-negative bacterial GH30-8 enzyme, XynA, from *Erwinia cluysanthemi* (EcXynA). A conserved tryptophan residue (Trp25) positioned by this loop establishes a predicted −3 xylosyl binding subsite (St. John et al., 2011; Urbanikova et al., 2011). While the Cα position for this conserved tryptophan is nearly identical in both BsXynC and EcXynA, the position of Trp25 in CpXyn30A is shifted 3.4 Å towards the inside portion of the loop. In either case, the indole side chain of the tryptophan lies in a similar position in all three enzymes (FIG. 17). As expected it is unique in the β7-α7 and β8-α8 loop regions relative to BsXynC and also, as expected, unique compared to CpXyn30A The β2-α2 loops of BsXynC and EcXynA are both very similar but the analogous region of CpXyn30A is considerably larger due to the presence of an additional nine amino acids in the α2 helix. In all three enzymes, a single aromatic amino acid stacking interaction is observed between residues in helices α2 and α3 (FIG. 8b). The conserved interaction shared by these three xylanases consists of a phenylalanine (BsXynC and EcXynA) or tyrosine (Tyr124 in CpXyn30A) from the α3-helix in a perpendicular stacking arrangement with a tryptophan (Trp66 in CpXyn30A) extending from the α2-helix. The extended α2 helix unique to CpXyn30A provides two additional intramolecular contacts with adjacent regions of the enzyme.

In the first interaction, Trp58 of CpXyn30A overlays the α3-helix and stacks perpendicular to Tyr120 (FIG. 8b). The second interaction found in the extended loop region is a hydrogen bond between Asp56 and Ser93 of the β4-α4 loop region. These last two contacts are not found in the BsXynC or EcXynA enzymes and may serve a role in supporting the beta-structured β3-α3 loop region as originally described in BsXynC (St John et al., 2011), but not in EcXynA.

A structural difference between GH30-8 enzymes from Gram-negative bacteria and those from Gram-positive bacteria (St. John et al, 2011) is found in the β3-α3 and β4-α4 loop regions (FIG. 8c). In CpXyn30A, this region adopts a fold similar to the Gram-positive GH30-8 enzymes (BsXynC-like) with a small β-structure extending upward at the top of the β3-α3 loop and a region in the β4-α4 loop which supports this extended β-structure primarily through stacking interactions. This is in contrast to the Gram-negative homologs of these enzymes (EcXynA like) which lack the extended β3-α3 loop β-structure and instead relies solely on hydrogen bonding between the two loop regions for stabilizing contacts. These hydrogen bonds are not present in the Gram-positive examples of these enzymes (St. John et al., 2011).

The β7-α7 loop region (FIG. 9) of CpXyn30A also displays a significantly different structure relative to the BsXynC and EcXynA enzymes. In this loop region of BsXynC and EcXynA, two conserved amino acids (Tyr231 and Ser235 in BsXynC) establish hydrogen bonds with the C-2 and C-3 hydroxyl groups of the α-1,2-linked GA appended on the xylan chain (FIG. 9a).

In CpXyn30A, this loop is smaller in size, but still has the conserved tyrosine (Tyr234). Following this amino acid, the loop region diverges slightly from the typical structure with Asp236 in place of a normally conserved serine and is positioned as to make a functionally similar contact unlikely. Despite this difference, it may be considered possible that the O-2 hydroxyl of sugars linked α-1,2 to the xylose in this subsite (typically GA) may hydrogen bond with Tyr234 as observed in the ligand bound crystal structures of BsXynC (FIG. 3a) and EcXynA (St. John et al., 2011, 291; Urbanikova et al., 2011).

In the altered sequence of the β8-α8 loop, four of the GA coordinating contacts identified for the ligand bound BsXynC structure are no longer available (FIG. 3b) (St. John et al., 2011). Surprisingly, despite the fact that the sequence of the β8-α8 loop region of CpXyn30A is completely different from the conserved sequence found in BsXynC and EcXynA, the structure of the loop does not significantly deviate from the Ca-trace of these model enzymes. This is most noteworthy since this region forms the basis for classification of the proteins into the GH30-8 subfamily due to its importance in GA recognition (FIG. 3b).

Functional Characterization.

While CpXyn30A has measurable activity on glucuronoxylan, the specific activity is low relative to the characterized GH30-8 xylanases as well as other more common β-1,4-endoxylanases such as those from families GH10 and GH11. In consideration of this finding, other polymeric substrates were tested for activity. These included carboxymethylcellulose, barley β-glucan, yeast glucan, glucomannan, galactoglucomannan, xyloglucan and gum arabic, but in each case there was no detectable activity. The results presented in Table 3 indicate that CpXyn30A displays similarly low specific activity on all xylan substrates tested.

TABLE 3

Specific activity[1] comparison of CpXyn30A and BsXynC on xylans and xylooligosaccharides.

| Substrates | Concentration | CpXyn30A | BsXynC |
|---|---|---|---|
| Sweetgum glucuronoxylan (SGX) | 10.00 mg/ml | 1.1 ± 0.1 | 70.7 ± 4.8 |
|  | 7.50 mg/ml | 1.1 ± ≤0.1 | 61.7 ± 3.8 |
| Wheat arabinoxylan (WAX) | 7.50 mg/ml | 1.7 ± 0.2 | nd[2] |
| Xylohexaose (X$_6$)[4] | 12.10 mM | 1.19 ± ≤0.01 | 0.019 ± ≤0.002[5] |
| Xylopentaose (X$_5$)[4] | 12.10 mM | 0.36 ± ≤0.01 | ND[3] |

[1]Units/mg protein, where one Unit is defined as one μmole/minute of activity. Data results from triplicate measurements resulting from a single assay. These results were consistent with numerous previous analyses. The given error is represented by the standard deviation.
[2]nd = Not detected
[3]ND = Not determined
[4]The data for these substrates represent an evaluation of specific activity based solely on the decrease of substrate. These values are higher than the true specific activity as the described competing transglycosylation reaction presumable consumes two X$_6$ molecules. Xylohexaose was digested for 8 minutes and xylopentaose was digested for 20 minutes.
[5]The X$_6$ substrate concentration was only 10 mM for this reaction, a difference in the comparison which is considered inconsequential to this study.

Interestingly, specific activity was 57% greater on WAX than on SGX when measured at the same substrate concentration (7.5 mg/ml). Studies employing X6 as a substrate at 12.1 mM (roughly the molar equivalence of 10 mg/ml xylan) show that CpXyn30A exhibits a similar activity as with 10 mg/ml SGX a characteristic not previously observed for other GH30-8 enzymes (see below).

In TLC analysis of an overnight hydrolysate of SGX by CpXyn30A, X2, X3, X4 and the primary aldouronate, GX4 (aldopentauronate, FIG. 10A) were observed. However, without further studies, the configuration (i.e. GA substitution position) of this aldouronate product is unknown.

CpXyn30A also efficiently processed WAX with only low levels of X2 and X3 apparent following an overnight digestion, but numerous other spots were observed on the plate which did not align with any of our standards. This suggests they are arabinofilranose substituted xylooligosaccharides instead of neutral oligoxylosides. Hydrolysis of X6 and X5 resulted in a distribution of smaller xylooligosaccharides similar to those observed for glucuronoxylan hydrolysis. There was only slight hydrolysis of X4 observed (FIG. 10B) and no detectable hydrolysis of X3 in overnight reactions (FIG. 10B).

Activity measurements of BsXynC confirm the reported function of this enzyme as a glucuronoxylan xylanohydrolase which requires a substitution of α-1,2-linked GA residues for activity. Multiple attempts were made to obtain activity measurements for the hydrolysis of WAX by BsXynC, including one attempt which used a 10-fold greater amount of enzyme than that used in similar reactions employing CpXyn30A and an overnight reaction time. However, all results were generally too variable and close to zero to be reported as anything other than 'not detected' (Table 3).

In agreement with previous findings, it is observed that BsXynC activity on X6 (10 mM) was 3-orders of magnitude (6172 fold) lower than on SGX (at 7.5 mg/ml) (Urbanikova et al., 2011), supporting the requirement for the GA appendage for activity.

Parallel TLC studies of the reaction products generated by BsXynC also confirm our current understanding of these enzymes and have provided further insight to their specificity (FIGS. 10A & 10B). Hydrolysis of SGX by BsXynC yielded an array of aldouronate sugars (St. John et al., 2006; Vrsanska et al., 2007) while reactions containing WAX as substrate did not yield any detectable smaller sugars, a result supported by the lack of detectable enzymatic activity on this substrate in kinetic studies (Table 3). The TLC analysis of BsXynC hydrolysis of X6 visually confirms the results presented in Table 3 with a very low activity observed for hydrolysis of this substrate. In contrast to these observations, overnight hydrolysis of GX4 by BsXynC resulted in xylose and the smaller aldouronate, aldotetrauronate (FIG. 10B).

Xylooligosaccharide hydrolysis studies showed that CpXyn30A has a competing transglycosylase activity (Shaikh & Withers, 2008). For this to occur, following the nucleophilic attack on the anomeric carbon by the catalytic nucleophile (E232 in CpXyn30A) an enzyme-substrate complex is formed which, in retaining glycosyl hydrolase enzymes (such as CpXyn30A), typically resolves by release of the sugar from the enzyme through a water molecule activated by the other member of the catalytic acid/base pair (E143 in CpXyn30A) (Shaikh & Withers, 2008). This accepted, double-displacement reaction scheme generates smaller sugars from polymeric substrates. However, if a sugar molecule were to bind into the active site cleft instead of a water molecule, then the C-4 hydroxyl group of the non-reducing terminal residue may become activated, resulting in a transglycosylation reaction creating a new β-1,4-xylosidic bond instead. For retaining glycosyl hydrolases like GH30 enzymes, transglycosylation may occur as a product of a failed hydrolytic reaction.

Figure 11:
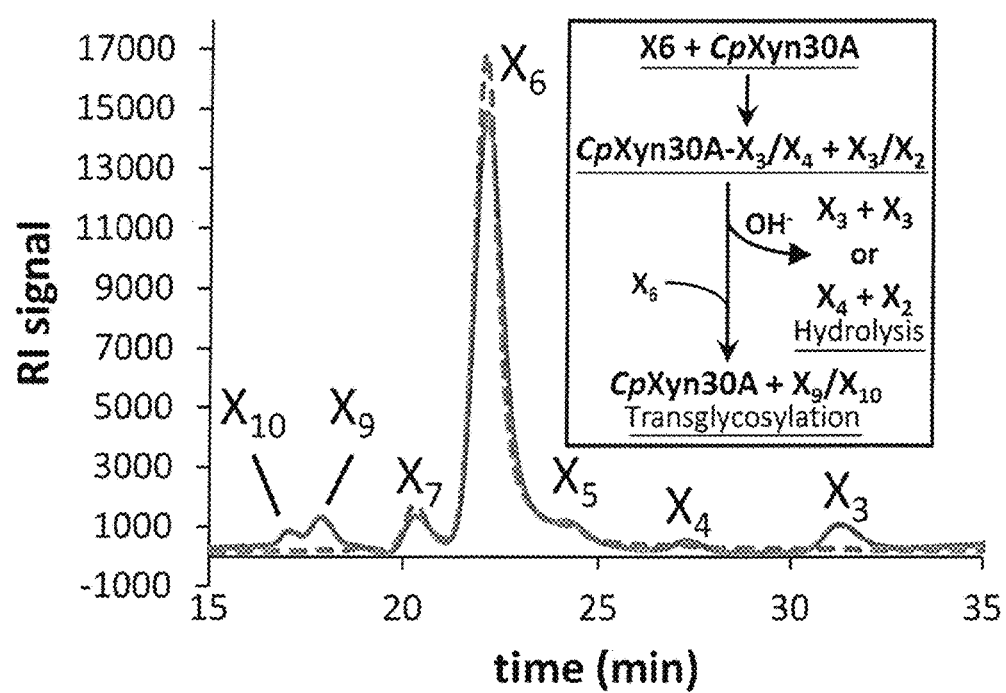
FIG. 11. HPLC analysis of CpXyn30A hydrolysis of xylohexaose showing transglycosylation activity and a flow chart for how this occurs.

Here, reaction mixtures consisting of X6 as the most abundant substrate were employed to probe the transglycosylase activity of CpXyn30A. If X6 binds so that it will be hydrolyzed into two molecules of X3, and a second X6 reoccupies the other half of the active site cleft, then the condensation of these two sugars will result in the formation of the xylooligosaccharide xylononaose (X9) (FIG. 11, inset). Because an initial hydrolytic activity is required to observe transglycosylation, the net reaction proceeds toward the right (smaller xylooligosaccharides) due to the eventual buildup of limit products which do not act as substrates for further endo-hydrolysis.

Figure 12:
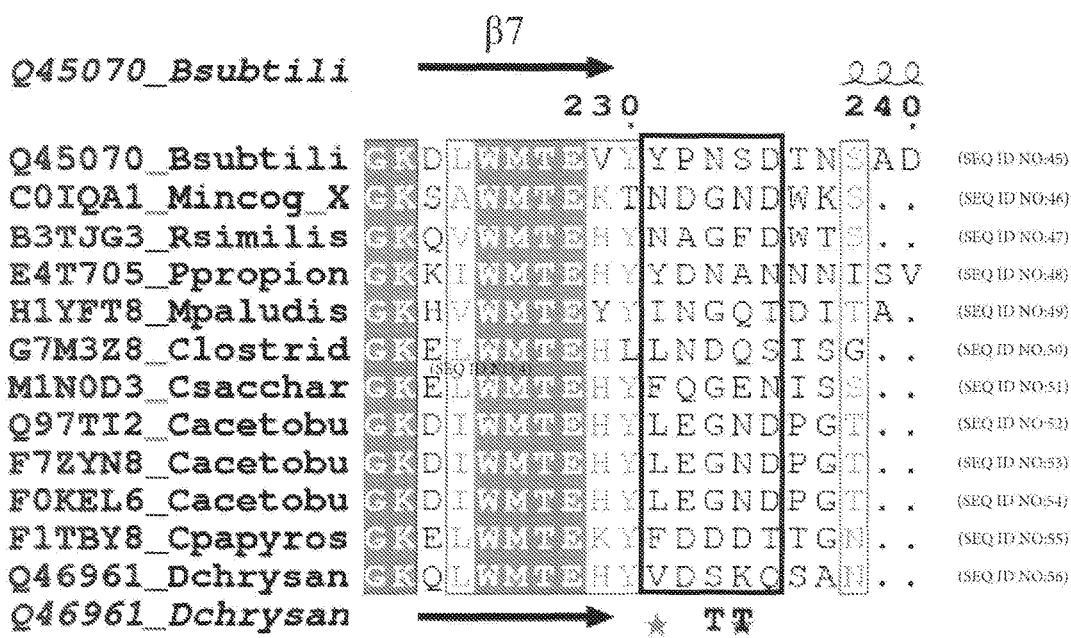
FIG. 12. β7-α7 loop regions of the disclosed GH30-8 subset of enzymes being compared to XynC from *Bacillus subtilis* (top, Q45070_Bsubtili) and XynA from *Erwinia chrysanthemi* (bottom, Q46961_Dchrysan). The sequence labeled Q45070 is SEQ ID NO:5, residues 222 to 241; the sequence labeled C0IQA1 is SEQ ID NO:32, residues 218 to 235; the sequence labeled B3TJG3 is SEQ ID NO:33, residues 214 to 231; The sequence labeled E4T705 is SEQ ID NO:3, residues 255 to 275; the sequence labeled H1YFT8 is SEQ ID NO:4, residues 234 to 252; the sequence labeled G7M3Z8 is SEQ ID NO:34, residues 219 to 236; the sequence labeled M1N0D3 is SEQ ID NO:35, residues 219 to 236; the sequence labeled Q97TI2 is SEQ ID NO:1, residues 253 to 270; the sequence labeled F7ZYN8 is SEQ ID NO:36, residues 221 to 238; the sequence labeled F0KEL6 is SEQ ID NO:37, residues 221 to 238; the sequence labeled F1TBY8 is SEQ ID NO:2, residues 257 to 274; the sequence labeled Q46961 is SEQ ID NO:31, residues 218 to 235.
Figure 13:
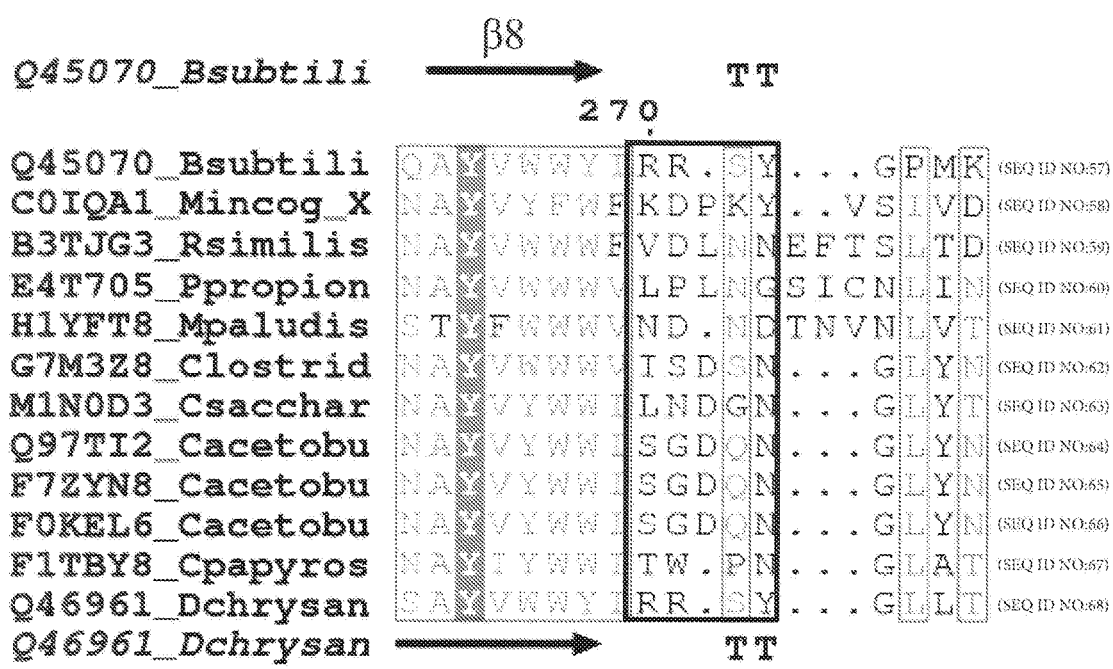
FIG. 13. β8-α8 loop regions of the disclosed GH30-8 subset of enzymes being compared to XynC from *Bacillus subtilis* (top, Q45070_Bsubtili) and XynA from *Erwinia chrysanthemi* (bottom, Q46961_Dchrysan). The sequence labeled Q45070 is SEQ ID NO:5, residues 263 to 278; the sequence labeled C0IQA1 is SEQ ID NO:32, residues 253 to 270; the sequence labeled B3TJG3 is SEQ ID NO:33, residues 249 to 268; The sequence labeled E4T705 is SEQ ID NO:3, residues 292 to 311; the sequence labeled H1YFT8 is SEQ ID NO:4, residues 269 to 287; the sequence labeled G7M3Z8 is SEQ ID NO:34, residues 254 to 270; the sequence labeled M1N0D3 is SEQ ID NO:35, residues 254 to 270; the sequence labeled Q97TI2 is SEQ ID NO:1, residues 288 to 304; the sequence labeled F7ZYN8 is SEQ ID NO:36, residues 256 to 272; the sequence labeled F0KEL6 is SEQ ID NO:37, residues 256 to 272; the sequence labeled F1TBY8 is SEQ ID NO:2, residues 292 to 307; the sequence labeled Q46961 is SEQ ID NO:31, residues 256 to 271.

In the present study, hydrolysis of X6 by CpXyn30A results in what is predicted from HPLC chromatograms as xylodecaose (X10) and X9 as well as smaller xylooligosaccharides such as X2 through X4 (FIGS. 11 & 12). These data were confirmed by TLC analysis which showed that within 20 minutes of the start of the reaction, hydrolysis of X6 resulted in a spot with no mobility (est. DP degree of polymerization >8) and small amounts of X4, X3 and X2. Formation of X10 and X9 may occur through a transglycosylation when CpXyn30A cleaves X6 such that either a X3 or X4 is positioned in the glycone side of the substrate binding cleft in the enzyme substrate complex. Because xylooligosaccharides smaller than X5 are not hydrolyzed they cannot be a source for further transglycosylation.

Based on this analysis, specific activities (Table 3) are anticipated to be lower than reported as the enzyme catalyzed transglycosylation reaction consumes two molecules of X6. It is impossible to determine what the ratio of hydrolysis:transglycosylation reactions might be without quantification of X9 and X10.

Transglycosylation does not likely contribute substantially during initial hydrolysis of polymeric xylan as the concentration of reducing termini is much lower and unlikely to significantly compete as an acceptor through the limited reaction time. Interestingly, even though the model enzyme BsXynC only hydrolyzes neutral xylooligosaccharides such as X6 very slowly, the activity that was observed appears from TLC to resolve in part by transglycosylation, similar to CpXyn30A (FIG. 4b). Similar results were previously reported for another GH30-8 Gram-positive enzyme (a highly conserved homolog from *Bacillus* sp. Strain BP-7) (Gallardo et al., 2010).

Our data on the rate of hydrolysis of X6 agrees with the previously reported level of activity of the Gram-negative GH30-8 enzymes EcXynA having 3-orders lower activity on this neutral xylooligosaccharide than on a polymeric glucuronoxylan substrate (Urbanikova et al., 2011). Transglycosylation can also be observed by TLC after the overnight digestion of GX. This indicates that BsXynC may be producing disubstituted aldouronates (FIG. 4B).

Clues as to the distinctive comparative function of these enzymes may be ascertained from their structures. Of the five hydrogen bonds and one salt bridge that have been described which establish the interaction between the β7-α7 and β8-α8 loops and the GA side chain in the BsXynC and EcXynA enzymes, only two hydrogen bonds are thought to still be possible in CpXyn30A. These positions, equivalent to Tyr234 and Trp265 in CpXyn30A may be available for hydrogen bonding with either GA or arabinofuranose substitutions linked α-1,2 on the main xylan chain. However, since activity measurements are similar on neutral xylooligosaccharides and xylans, it seems unlikely that this potential hydrogen bonding position plays a significant role in xylan hydrolysis. Instead, the β8-α8 loop contains larger, hydrophobic amino acids which would appear from inspection of a surface analysis to displace the xylose and any substitution in this position (-2 subsite). Because of this displacement, substitutions in this region most likely are beyond hydrogen bonding distance of Tyr234 and Trp265. The increased size of the β8-α8 loop may reorient the glycone bound xylan sugar out of an ideal orientation for hydrolysis.

From these data, CpXyn30A stands out as a defunct GH30-8 xylanase having no apparent specificity for O-2 linked GA substitutions and a greatly decreased specific activity on the usual glucuronoxylan substrate while simultaneously possessing a unique ability to hydrolyze WAX, SGX and the neutral xylooligosaccharide X6 at rates approximately 100-fold greater than BsXynC processing of neutral sugars. Even though CpXyn30A has a demonstrated xylanase activity, it is not known whether the enzyme represents an evolved functionality whose role has not yet been identified or a residual xylanase activity resulting from unbeneficial changes to the Xyn30A gene in *C. papyrosolvans*.

The data presented helps us understand the function of the GH30-8 β8-α8 loop in determination of the specificity of these enzymes. It seems clear that the conserved sequence of this loop found in the BsXynC/EcXynA enzymes may not only enable recognition of the α-1,2-linked GA appendage, but might also prevent binding of neutral sugars by physically obstructing access to the binding cleft.

Example 2: Expression and Purification of CaXynQ97

The codon optimized (for *E. coli*) coding sequence for CaXynQ97 including a C-terminal His-tag was synthesized by DNA 2.0 and inserted into their pJexpress 411 kanamycin selective expression vector (pCaXyn30A). Chemically competent *E. coli* BL21 (DE3) was transformed with the pCaXynQ97 expression vector and selected for on LB agar plates containing 50 ug/ml kanamycin. The following day a single colony was selected from the plate and inoculated into a 50 ml volume of LB media containing 50 ug/ml kanamycin contained in a 250 ml long-neck shake flask. This was grown overnight at 37° C. with shaking at 250 rpm. The following morning, 5 ml aliquots of this culture were used to inoculate several 37° C. preequilibarted 0.5 liter volumes of LB media containing 50 ug/ml kanamycin contained in a Fernbach flask. This was grown at 37° C. with shaking at 300 rpm until a measured OD 600 nm of approximately 0.7 and the culture was then induced by addition of IPTG to a final concentration of 1 mM. The induced culture was then grown for an additional 4-5 hours at 37° C. and shaking at 300 rpm. Following induction, the foil cap was kept in place for 1 hour, but removed for the remaining hours of induction. The cells were then collected through centrifugation at 10400×g (i.e., 8000 rpm in a GSA rotor) at 4° C. Each pellet resulted from 0.5 liter of expression culture. The pelleted cells were stored frozen at −80° C. until used for protein purification.

The His-tagged version of this enzyme was purified in a standard manner very similar to CpXyn30A (C7I) with use of a Ni-affinity IMAC chromatography column and subsequent gel filtration chromatography. After several years attempting to obtain protein crystals for crystallographic structure determination, we decided to reclone the CaXynQ97 enzyme from the pJexpress 411 vector into the pET28 protein expression (Novagen) with removal of the C-terminal His-tag. The new pET28 based expression construct (pCaXynQ97-nohis) transformed into $E.$ $coli$ BL21 (DE3) expressed very well as did the previous pJexpress construct. The preceding expression protocol and the following cell processing procedure apply to both constructs except that for the cell processing for the no-his-tag expression product was "beefed-up" with addition of lysozyme in the hope that it would make for a cleaner preparation since no affinity tag was being used. As will be explained it turned out that this purification was actually just as easy as an affinity system due to the inherent high isoelectric point of CaXyn30A.

For protein purification, four pCaXynQ97-nohis $E.$ $coli$ protein expression pellets were thawed at room temperature and then on ice. An EDTA-free Mini cOmplete protease inhibitor tablet (Roche) was added to one of these pellets. A volume of 8 ml of 25 mM Tris HCl pH 7.1 was added to each pellet and the soft pellets were resuspended using a glass rod and eventually, to obtain fluidity, with the action of a 5 ml pipet. Resuspended pellets were combined and each of the four centrifuge tubes (250 ml volume) were rinsed with 2 ml of Tris buffer. Lysozyme was added to a final concentration of 20 ug/ml and the full volume (~47.5 ml) was transferred to a 250 ml capacity glass sonication vial and allowed to cool on ice for 15 minutes. The sonic microtip was calibrated according to instructions and then submerged ~1 inch below cell suspension surface. Set to 20% power (~95 watts) and an approximate control knob setting of 3.5. Cycle twelve times of 10 seconds on, 50 seconds off in ice/water. Total process time is 12 minutes. Collect sonicate, and based on approximate volume add 1M $MgCl_2$ to a final concentration of 2 mM and lysozyme as added before. Add 250 Units of Benzonase (Novagen) and rock at room temperature for 30 minutes. Cell lysate volume is split into 2-45 ml Oakridge centrifuge tubes. Preequilibrate centrifuge to 15° C. and centrifuge cell lysates for 30 minutes at 15° C. at G-Force (i.e.; 14000 rpm (SS-34 rotor)). Collect supernatant cell free extract and filter through 0.45 um syringe tip filter.

The processing of both the His-Tag and no-His-Tag versions of CaXynQ97 used Tris based buffers as it was shown several times that this enzyme precipitates in the phosphate based buffers typically used for IMAC chromatography, as in the purification of CpXynC7I. The resulting cell free extract (CFE) of the CaXynQ97-nohis enzyme was fractionated on a 5 ml Econo-Pac CM column (Bio-Rad) equilibrated in pH 7.1 25 mM Tris HCl and a gradient to 500 mM NaCl. The fractionation was very clean and the eluted protein peaks were combined and concentrated using an Amicon Ultra 15 with 10K MWCO. This concentrated CaXynQ97 preparation was then desalted using a 5 ml Econo-Pac P-6 desalting column and then again concentrated with a another Amicon Ultra 15 10K MWCO centrifugal concentrator. It was noted that high concentrations of CaXynQ97-nohis did not seem to like the high salt, so prior to concentrating for subsequent desalting the enzyme was diluted with the Tris. The preparation was then purified on a Superdex 200PG 16/600 column (GE healthcare) equilibrated with 25 mM Tris HCl pH 7.5, 100 mM NaCl. Concentrated and buffer exchanged into 25 mM Tris HCl pH 7.1. Remaining NaCl is estimated at <5 mM. This form of CaXynQ97-nohis proved to be very soluble remaining is solution at concentrations greater than 100 mg/ml. Protein crystal screening was performed with a preparation at ~40 mg/ml.

Functional Characterization.

Wheat arabinoxylan was digested with the same number of Units of activity of the three enzymes tested. Following a pre-established time the reaction was killed by heating to 90° C. for 10 minutes. The reaction volume was then adjusted to 90% ethanol by addition of 100% ethanol and allowed to precipitate overnight at 4° C. The resulting material was centrifuged at 20000×g for 30 minutes at 4° C. and the supernatant and the pellet were isolated. The pellet was washed with cold 100% ethanol and the supernatant was rotovaped to remove all the ethanol and then brought to a known volume. The pellet was resuspended to this same volume. Total reducing end was determined with the Nelson's test and total carbohydrate was determined with the Phenol Sulfuric assay. The degree of polymerization (DP) was calculated as the quotient of these two values and used to characterize the oligomeric state and hence information regarding the xylanases used.

Comparison of XynQ97 and XynC71.

Representative examples of the disclosed GH30-8 enzymes (XynQ97 and XyncC71) differ slightly in their respective hydrolysis product profiles, but it is clear they are very similar when compared to the canonical GH30-8 enzyme family homolog XynC. They are shown to yield a series of small xylooligosaccharides and aldouronates indicating the enzymes have no obvious preference for the GA xylan chain appendage. This is further supported by the arabinoxylan limit hydrolysis by these enzymes, in comparison to XynC, which was unable to degrade this substrate in any way (FIG. 6 and FIG. 10A), the enzymes of the present invention readily processed this substrate to small xylooligosaccharides and small arbinofuranose substituted xylooligosaccharides.

Notably, based on the intensity of the remaining sample spot for the TLCs of FIG. 6 and FIG. 20 (bottom spots), the disclosed enzymes processed the arabinoxylan to smaller oligoxylosides and arabinofuranose xylooligosaccharides more efficiently than the GH10 xylanase XynA1CD indicating that the disclosed enzymes are better at cleaving xylan chains in regions of frequent side chain substitution.

XynC71, while it has a comparably low rate of hydrolysis (see Example 1) also appears to process wheat arabinoxylan just as efficiently as XynQ97, but glucuronoxylans to a slightly lesser degree (FIG. 6). Relative to the limit hydrolysis product profile of a typical GH10 xylanase and a canonical GH30-8 appendage specific xylanase on either of these two xylans types, XynQ97 and XynC71 act in a similar fashion due to the altered β7-α7 and β8-α8 loops.

Our data suggests that the GH30-8 xylanases of the present invention are able to hydrolyze highly substituted xylan substrates where other xylanases are unable to function due to steric interaction between the enzyme and xylan side chain substitutions, thereby liberating more substituted xylooligomers and yielding more oligosaccharide sugar liberated from highly substituted often insoluble xylan substrates (Table 4).

TABLE 4

Comparison of XynQ97 with Industry Leading GH10 Xylanase.

| Enzyme | Analysis | Supernatant/ Pellet | Total RE (umoles) | Total Carbohydrate (umoles) | DP |
|---|---|---|---|---|---|
| XynQ97 | 1 | Supernatant | 32.87 | 218.15 | 6.63 |
|  |  | Pellet | 0.191 | 5.14 | 27.1 |
|  | 2 | Supernatant | 27.00 | 191.69 | 7.1 |
|  |  | Pellet | 0.298 | 5.26 | 17.7 |
| Industry Leading GH10 Xylanase PbXyn10A1CD | 1 | Supernatant | 39.48 | 230.9 | 5.84 |
|  |  | Pellet | 0.232 | 9.92 | 42.84 |
|  | 1 | Supernatant | 39.19 | 184.1 | 4.69 |
|  |  | Pellet | 0.750 | 18.78 | 21.12 |
|  | 2 | Supernatant | 28.6 | 175.81 | 6.14 |
|  |  | Pellet | 1.53 | 36.01 | 23.57 |

Example 3. Methods of Using the GH30-8 Xyalanases to Reduce Biomass

The enzymes and enzyme compositions of the present invention can be used to hydrolyze biomass materials or other suitable xylan containing feedstocks.

The GH30-8 xylanases and compositions thereof provided above are useful in reducing xylans found in any source, including biomass, due to their unique structure. Specifically, without the canonical GH30-8 subfamily specific loop regions which define the GA appendage specificity of these enzymes, the GH30-8 subset of enzymes presently disclosed are considered free of such restrictions or limitations and therefore appears to function more generally as a β-1,4-endoxylanase, not having clear preference toward xylan side chain appendages. These GH30-8 xylanases of the present invention are therefore more comparable to the very common β-1,4-endoxylanases of glycoside hydrolase families 10 and 11 while simultaneously being unique from these by yielding unique hydrolysis product profiles and obtaining better liberation of oligomers from highly substituted xylans.

These "generic" GH10 and GH11 endo-β-1,4-xylanases process xylans by working around the appendages like obstacles which prevent the enzyme from accessing the xylan chain. In doing this the GH10 endoxylanase is known to produce the smallest of the GA-substituted xylooligosaccharides (aldotetrauronate). This is because the substrate binding cleft of these xylanases can accommodate 2-GA appendages separated by just two xyloses (−3 and +1 subsites).

Figure 2:
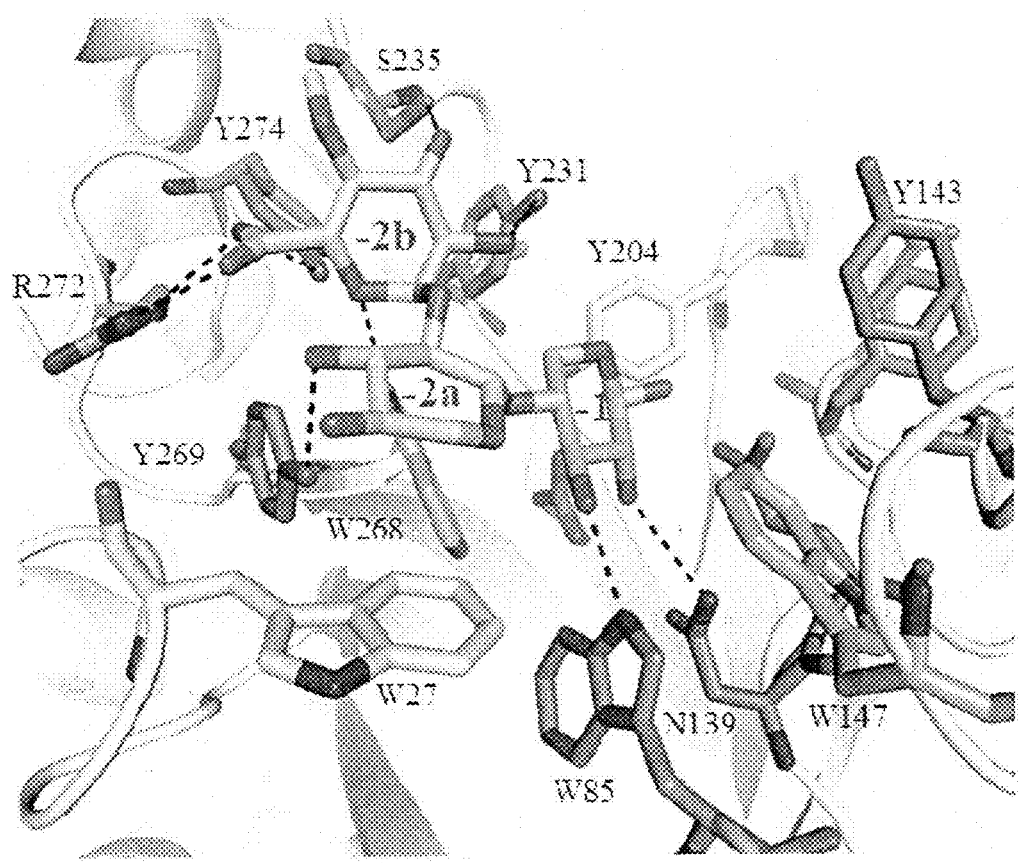
FIG. 2. Molecular contacts between aldotriuronate and the active site/substrate binding cleft of the canonical GH30-8 glucuronoxylanhydrolase, XynC from *Bacillus subtilis* 168.
Figure 3:
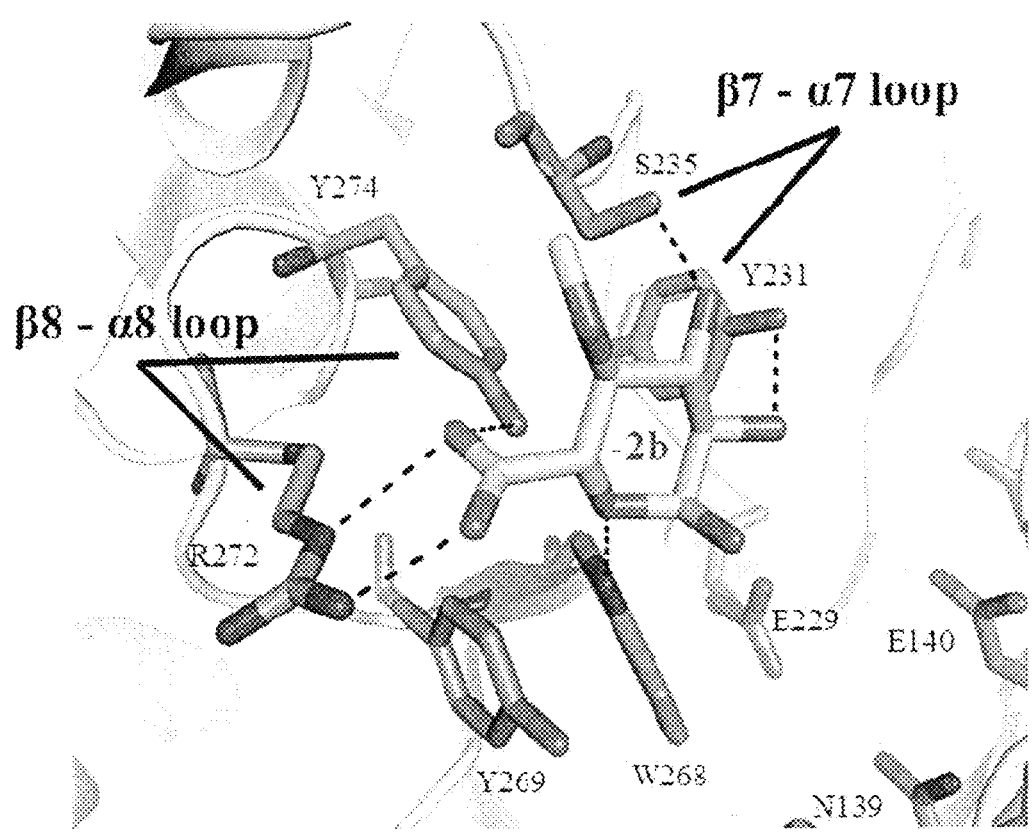
FIG. 3. A close-up of the glucoronate appendage with the typically conserved β7-α7 and β8-α8 loop regions of XynC of *Bacillus subtilis* showing the contacts which allow specificity for this appendage in the canonical GH30-8 xylanases.

Using the canonical GH30-8 xylanase as a comparison it is known that these enzymes specifically bind the GA in the −2 subsite (FIGS. 2 & 3). Further, the limit hydrolysis product analysis yields the smallest GA substituted xylooligossacharide as aldotriuronate (see FIG. 6) resulting from a digest of beechwood glucuronoxylan by XynC. This indicates that the GH30-8 xylanases of the present invention appear likely to accommodate 2 GA appendages separated by just one xylose.

This is supported by the limit hydrolysis of both beechwood xylan and wheat arabinoxylan by XynQ97 (FIG. 6). For the enzymes representing the GH30-8 and GH10 xylanase families, the limit products show the expected results from many previously reported biochemical characterizations. For GH30-8 xylanases, hydrolysis of a glucuronoxylan results in singly substituted aldouronates of varying lengths, each containing a GA substitution penultimate to the reducing terminal xylan as described above (FIG. 1). Hydrolysis of arabinoxylan by this enzyme yields no detectable hydrolysis products as this substrate does not contain any GA substitutions. Hydrolysis of these different xylans by XynA1 also yields results that are expected from previous characterizations. On a glucuronoxylan, a GH10 enzyme will hydrolyze the polymer primarily to xylobiose with smaller amounts of xylose and xylotriose along with the primary limit aldouronate product, aldotetrauronate (FIG. 21A).

Example 4. Selection of GH30-8 Xylanases

We sought to select several additional GH30-8 xylanases of the present invention and confirm their xylan hydrolysis product profiles. Based on qualitative assessment of the uniqueness of the amino acid sequence of the β7-α7 and β8-α8 loop regions as observed in FIG. 5, we selected UniProt accession numbers C0IQA1, H1YFT8 and E4T705 for further characterization. The DNA sequence of the GH30-8 with accession number C0IQA1 derived from the nematode *Meloidogyne incognita* (Mi, MiXyn30A) was synthesized for cloning into an expression construct. This was done by the company DNA2.0 (Menlo Park, Ca). The DNA coding sequence was optimized for expression in *E. coli* containing no secretion signal sequence, with addition of a C-terminal His tag for affinity purification and the synthesized fragment cloned into their pJ411 protein expression vector. For the protein coding sequence with accession number H1YFT8 which derives from bacterium *Mucilaginibacter paludis* (Mp, MpXyn30A) and accession number E4T705 from the bacterium *Paludibacter propionicigenes* (Pp, PpXyn30A), genomic DNA for these two bacteria was ordered from DSMZ microbial stock center in Germany. The genes coding for these two enzymes were PCR amplified and the products cloned into the pET28 *E. coli* expression vector creating a fusion with the vector encoded C-terminal His-tag for affinity purification of the protein expression product.

In addition to these we also obtained the complete enzyme for which Q97 was the representative catalytic domain. This protein is referred to as Q97_RCN as the additional C-terminal portion of the native amino acid sequence encodes a carbohydrate binding domain of family 13 (CBM13, Ricin-like domain, RCN). This expression construct was obtained from DNA2.0 just as the original Q97 expression construct was obtain. However, this new expression construct did not include an affinity purification tag. The Q97_RCN protein was considered important to show that the enzyme still functions the same with respect to hydrolysis product profiles. Although, untested at this point, it is expect that inclusion of the native CBM13 domain of Q97 may improve upon functional features such as hydrolysis reaction rate, better performance in disruption of insoluble xylans, and provide better commercial qualities such as an increased temperature optimum and reaction stability.

Figure 19:
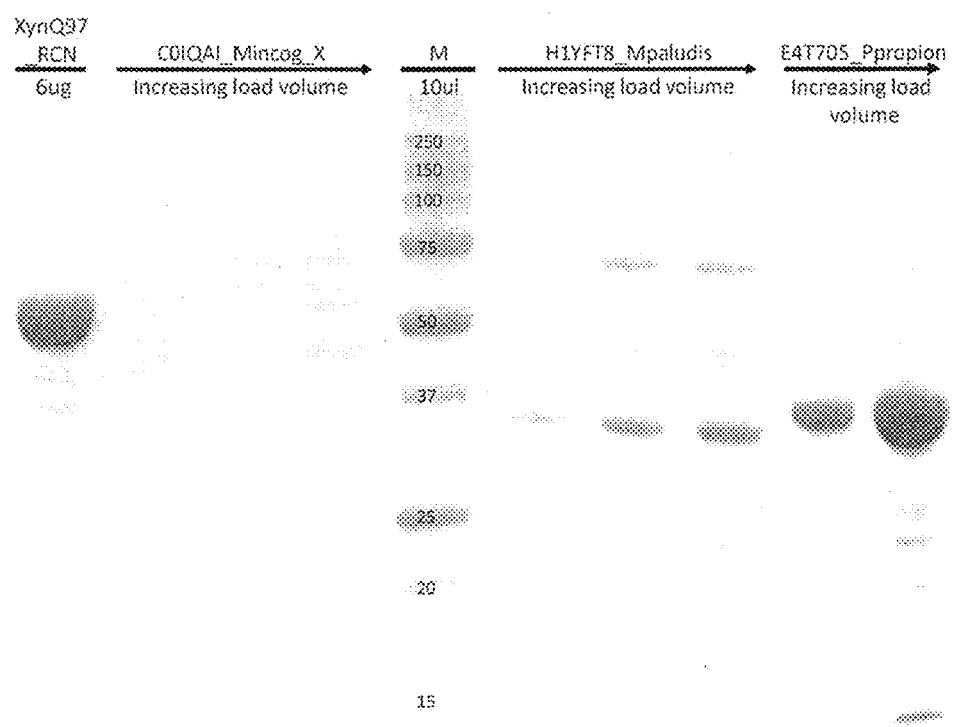
FIG. 19. SDS-PAGE analysis of additional GA-independent GH30-8 xylanases and the full CaXyn30A (Q97_RCN) xylanase containing the natively encoded C-terminal CBM13 module.

For these four new protein expression constructs, expression was quickly optimized for different growth temperatures using laboratory auto-induction procedures. It was shown that MiXyn30A did not result in a soluble protein expression product. This was confirmed by the lack of a recoverable, near-pure protein of the correct molecular weight size by nickel immobilized metal affinity chromatography (IMAC) followed by SDS-PAGE (FIG. 19). Just to verify, the "peak region" for this IMAC elution was desalted and concentrated to an estimated protein concentration of 0.3 mg/ml. This was used in a 50 ul overnight xylan digestion reaction intended for TLC analysis (FIG. 20). For this protein, no hydrolysis of xylan is observed, most likely due to not obtaining a soluble MiXyn30A protein. Most likely this protein is not soluble as it is a eukaryotic enzyme which may, in its native nematode host, be glycosylated, a feature which may enhance solubility and other biophysical features. The MpXyn30A enzyme expression was also not very good, but IMAC chromatography resulted in a relatively pure protein in the expected size range by SDS-PAGE (FIG. 19). Hydrolysis product analysis by TLC showed only a very low level of hydrolysis occurred in the overnight reaction (FIG. 20). Notably, the barely detectable larger oligosaccharides produced by this enzyme hydrolysis suggest that MpXyn30A was not an efficiently functioning xylanase and this is likely due to the specific sequence of the β7-α7 and β8-α8 loop regions. Our original thinking, that changes to these two regions in the GA-dependent (canonical) GH30-8 xylanases could nullify the function of these enzymes was valid. We took a risk with a strong possibility that no activity would be detectable and discovered a novel, broad-specificity xylanase activity. Just opposite of this finding, the PpXyn30A protein, although it also did not express well, resulted in the best yield of pure protein following the IMAC purification. This is nicely seen from the SDS-PAGE analysis (FIG. 19). Further, an overnight reaction with this protein yielded a hydrolysis product profile nearly identical to Q97 and C7I. This again bolsters our claim regarding these GA-independent GH30-8 xylanases (FIG. 20).

The Q97_RCN protein expresses the best of all the other three, catalytic domain only proteins. Although expression is good the vast majority of the expressed protein at all tested expression temperatures is in inclusion bodies. Still, purification of the soluble form yielded plenty for biochemical studies (FIG. 19). TCL analysis of a xylan hydrolysis confirmed that the modular enzyme functioned just as the isolated catalytic domain of Q97 (FIG. 20).

Other embodiments and uses of the invention will be apparent to those skilled in the art from consideration from the specification and practice of the invention disclosed herein. All references cited herein for any reason, including all journal citations and U.S./foreign patents and patent applications, are specifically and entirely incorporated herein by reference. It is understood that the invention is not confined to the specific reagents, formulations, reaction conditions, etc., herein illustrated and described, but embraces such modified forms thereof as come within the scope of the following claims.

SEQUENCE LISTING

This specification includes the sequence listing that is concurrently filed in computer readable form. This sequence listing is incorporated by reference herein.

We claim:

1. A method of hydrolyzing or digesting a lignocellulosic biomass material comprising; contacting the lignocellulosic biomass material with a glycoside hydrolase family 30 subfamily 8 (GH30-8) enzyme composition comprising an isolated polypeptide, wherein the polypeptide is a glucuronic acid (GA)-independent GH30-8 enzyme comprising the amino acid sequence (W or Y)(W or F)W(I or V or F)(not R)(not R) (SEQ ID NOs:69-80) within the β8-α8 loop of the enzyme, wherein the lignocellulosic biomass material comprises hemicellulose, cellulose, or mixtures thereof.

2. The method of claim 1, wherein the lignocellulosic biomass material comprises an agricultural crop, a byproduct of a food/feed production, a lignocellulosic waste product, a plant residue, or waste paper.

3. The method of claim 1, wherein the lignocellulosic biomass material is subjected to a pretreatment.

4. The method of claim 3, wherein the pretreatment comprises a thermal, aqueous or thermomechanical pulping.

5. The method of claim 3, wherein the pretreatment comprises an acidic pretreatment or a basic pretreatment.

6. The method of claim 1, wherein the GA-independent GH30-8 enzyme comprises an amino acid sequence at least 85% identical to an amino acid sequence selected from the group consisting of SEQ ID NO:1 residues 33-420 (Q97TI2), SEQ ID NO:2 residues 32-421 (F1TBY8), SEQ ID NO:3 residues 45-423 (E4T705), SEQ ID NO:4 residues 33-399 (H1YFT8), SEQ ID NO:32 (C0IQA1), SEQ ID NO:33 (B3TJG3), SEQ ID NO:34 (G7M3Z8), SEQ ID NO:35 (M1N0D3), SEQ ID NO:36 (F7ZYN8), and SEQ ID NO:37 (F0KEL6).

7. The method of claim 6, wherein the GA-independent GH30-8 enzyme comprises an amino acid sequence that is at least 90% identical to the selected amino acid sequence.

8. The method of claim 7, wherein the GA-independent GH30-8 enzyme comprises an amino acid sequence that at least 95% identical to the selected amino acid sequence.

9. The method of claim 1, wherein the GH30-8 enzyme composition further comprising at least one additional protein having enzymatic activity.

* * * * *